United States Patent
Ballabio et al.

(10) Patent No.: US 9,206,401 B2
(45) Date of Patent: Dec. 8, 2015

(54) THERAPEUTIC STRATEGIES TO TREAT CNS PATHOLOGY IN MUCOPOLYSACCHARIDOSES

(75) Inventors: Andrea Ballabio, Napoli (IT); Alessandro Fraldi, Napoli (IT)

(73) Assignee: FONDAZIONE TELETHON, Rome (IT)

(*) Notice: Subject to any disclaimer, the term of this patent is extended or adjusted under 35 U.S.C. 154(b) by 0 days.

(21) Appl. No.: 13/996,386

(22) PCT Filed: Dec. 22, 2010

(86) PCT No.: PCT/IB2010/056024
§ 371 (c)(1), (2), (4) Date: Jul. 24, 2013

(87) PCT Pub. No.: WO2012/085622
PCT Pub. Date: Jun. 28, 2012

(65) Prior Publication Data
US 2013/0302308 A1    Nov. 14, 2013

(51) Int. Cl.
C12N 9/16 (2006.01)
C07K 14/81 (2006.01)
C12N 9/14 (2006.01)
A61K 48/00 (2006.01)

(52) U.S. Cl.
CPC .............. *C12N 9/16* (2013.01); *C07K 14/8125* (2013.01); *C12N 9/14* (2013.01); *C12Y 301/06013* (2013.01); *C12Y 310/01001* (2013.01); *A61K 48/005* (2013.01); *C07K 2319/02* (2013.01); *C07K 2319/33* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| 5,863,782 | A |  | 1/1999 | Hopwood et al. |
|---|---|---|---|---|
| 2004/0248262 | A1 | * | 12/2004 | Koeberl et al. ............... 435/69.7 |
| 2005/0100986 | A1 | * | 5/2005 | Verma et al. ................. 435/69.1 |
| 2006/0057114 | A1 | * | 3/2006 | Whitley et al. .............. 424/93.2 |
| 2006/0122376 | A1 | * | 6/2006 | Chapman et al. ............ 530/383 |
| 2012/0107243 | A1 | * | 5/2012 | Curran et al. ................. 424/9.1 |
| 2012/0308544 | A1 | * | 12/2012 | Steinfeld ...................... 424/94.3 |

FOREIGN PATENT DOCUMENTS

| WO | 2006/007560 A2 | 1/2006 |
|---|---|---|
| WO | 2006/088503 A1 | 8/2006 |

OTHER PUBLICATIONS

Schwindt et al., "Brain-targeted therapy for mucopolysaccharidosis type II delivered by microencapsulated recombinant cells", Molecular Genetics and Metabolism, vol. 98, pp. 84-85, Oct. 2009.*
Cardone et al., "Correction of Hunter syndrome in the MPSII mouse model by AAV2/8-mediated gene delivery", Human Molecular Genetics, vol. 15, No. 7, pp. 1225-1236, 2006.*
(Continued)

*Primary Examiner* — Robert Mondesi
*Assistant Examiner* — Richard Ekstrom
(74) *Attorney, Agent, or Firm* — Lucas & Mercanti LLP

(57) ABSTRACT

The invention provides for nucleotide sequences encoding for a chimeric sulfatase, viral vectors expressing such sequences for gene therapy and pharmaceutical uses of the chimeric expressed protein. The invention is particularly applied in the therapy of mucopolysaccharidosis, preferably type IIIA.

19 Claims, 13 Drawing Sheets

(56) References Cited

OTHER PUBLICATIONS

Spencer, et al: "Targeting the Low-Density Lipoprotein Receptor on the Blood-Brain Barrier for Transport of beta-Glucoronidase Can Treat the Neurological Degeneration of MPSVII", Molecular Therapy, Academic Press, San Diego, CA, US, vol. 13, Jan. 1, 2006, p. S159.

Spencer, Brian J., et al: "Targeted delivery of proteins across the blood-brain barrier", Proceedings of the National Academy of Sciences of the United States of America, vol. 104, No. 18, May 1, 2007, pp. 7594-7599.

Ponder, Katherine Parker, et al: "Therapeutic neonatal hepatic gene therapy in mucopolysaccharidosis VII dogs", Proceedings of the National Academy of Sciences of the United States of America. vol. 99, No. 20, Oct. 1, 2002, pp. 13102-13107.

Sands, et al: "Gene therapy for lysosomal storage diseases", Molecular Therapy, Academic Press, San Diego, CA, US, vol. 13, No. 5, May 1, 2006, pp. 839-849.

Cheng, S. H., et al: "Gene therapy progress and prospects: gene therapy of lysosomal storage disorders", Gene Therapy, MacMillan Press Ltd., Basingstoke, GB, vol. 10, No. 16, Aug. 1, 2003, pp. 1275-1281.

\* cited by examiner

SEQUENCE LISTING

```
<160> NUMBER OF SEQ ID NOS: 35

<210> SEQ ID NO 1
<211> LENGTH: 72
<212> TYPE: DNA
<213> ORGANISM: Homo sapiens
<220> FEATURE:
<221> NAME/KEY: CDS
<222> LOCATION: (1)..(72)

<400> SEQUENCE: 1 atg ccg tct tct gtc tcg tgg ggc atc ctc ctg ctg gca ggc ctg tgc      48
Met Pro Ser Ser Val Ser Trp Gly Ile Leu Leu Leu Ala Gly Leu Cys
1               5                   10                  15 tgc ctg gtc cct gtc tcc ctg gct                                      72
Cys Leu Val Pro Val Ser Leu Ala
            20

<210> SEQ ID NO 2
<211> LENGTH: 24
<212> TYPE: PRT
<213> ORGANISM: Homo sapiens

<400> SEQUENCE: 2

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 3
<211> LENGTH: 75
<212> TYPE: DNA
<213> ORGANISM: Homo sapiens
<220> FEATURE:
<221> NAME/KEY: CDS
<222> LOCATION: (1)..(75)

<400> SEQUENCE: 3 atg ccg cca ccc cgg acc ggc cga ggc ctt ctc tgg ctg ggt ctg gtt      48
Met Pro Pro Pro Arg Thr Gly Arg Gly Leu Leu Trp Leu Gly Leu Val
1               5                   10                  15 ctg agc tcc gtc tgc gtc gcc ctc gga                                  75
Leu Ser Ser Val Cys Val Ala Leu Gly
            20                  25

<210> SEQ ID NO 4
<211> LENGTH: 25
<212> TYPE: PRT
<213> ORGANISM: Homo sapiens
```

<400> SEQUENCE: 4

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 5
<211> LENGTH: 75
<212> TYPE: DNA
<213> ORGANISM: Homo sapiens
<220> FEATURE:
<221> NAME/KEY: CDS
<222> LOCATION: (1)..(75)

<400> SEQUENCE: 5 atg ccc ccg ccc cgc acc ggc cgc ggc ctg ctg tgg ctg ggc ctg gtg      48
Met Pro Pro Pro Arg Thr Gly Arg Gly Leu Leu Trp Leu Gly Leu Val
1               5                   10                  15 ctg agc agc gtg tgc gtg gcc ctg ggc                                  75
Leu Ser Ser Val Cys Val Ala Leu Gly
            20                  25

<210> SEQ ID NO 6
<211> LENGTH: 25
<212> TYPE: PRT
<213> ORGANISM: Homo sapiens

<400> SEQUENCE: 6

Met Pro Pro Pro Arg Thr Gly Arg Gly Leu Leu Trp Leu Gly Leu Val
1               5                   10                  15

Leu Ser Ser Val Cys Val Ala Leu Gly
            20                  25

<210> SEQ ID NO 7
<211> LENGTH: 1509
<212> TYPE: DNA
<213> ORGANISM: Homo sapiens
<220> FEATURE:
<221> NAME/KEY: CDS
<222> LOCATION: (1)..(1509)

<400> SEQUENCE: 7 atg agc tgc ccc gtg ccc gcc tgc tgc gcg ctg ctg cta gtc ctg ggg      48
Met Ser Cys Pro Val Pro Ala Cys Cys Ala Leu Leu Leu Val Leu Gly
1               5                   10                  15 ctc tgc cgg gcg cgt ccc cgg aac gca ctg ctg ctc ctc gcg gat gac      96
Leu Cys Arg Ala Arg Pro Arg Asn Ala Leu Leu Leu Leu Ala Asp Asp
            20                  25                  30 gga ggc ttt gag agt ggc gcg tac aac aac agc gcc atc gcc acc ccg     144
Gly Gly Phe Glu Ser Gly Ala Tyr Asn Asn Ser Ala Ile Ala Thr Pro
        35                  40                  45 cac ctg gac gcc ttg gcc cgc gcc agc ctc ctc ttt cgc aat gcc ttc     192
His Leu Asp Ala Leu Ala Arg Ala Ser Leu Leu Phe Arg Asn Ala Phe
    50                  55                  60 acc tcg gtc agc agc tgc tct ccc agc cgc gcc agc ctc ctc act ggc     240
Thr Ser Val Ser Ser Cys Ser Pro Ser Arg Ala Ser Leu Leu Thr Gly
65                  70                  75                  80 ctg ccc cag cat cag aat ggg atg tac ggg ctg cac cag gac gtg cac     288
Leu Pro Gln His Gln Asn Gly Met Tyr Gly Leu His Gln Asp Val His
                85                  90                  95 cac ttc aac tcc ttc gac aag gtg cgg agc ctg ccg ctg ctc ctc agc     336
His Phe Asn Ser Phe Asp Lys Val Arg Ser Leu Pro Leu Leu Leu Ser
            100                 105                 110

```
caa gct ggt gtg cgc aca ggc atc atc ggg aag aag cac gtg ggg ccg      384
Gln Ala Gly Val Arg Thr Gly Ile Ile Gly Lys Lys His Val Gly Pro
        115                 120                 125 gag acc gtg tac ccg ttt gac ttt gcg tac acg gag gag aat ggc tcc      432
Glu Thr Val Tyr Pro Phe Asp Phe Ala Tyr Thr Glu Glu Asn Gly Ser
130                 135                 140 gtc ctc cag gtg ggg cgg aac atc act aga att aag ctg ctc gtc cgg      480
Val Leu Gln Val Gly Arg Asn Ile Thr Arg Ile Lys Leu Leu Val Arg
145                 150                 155                 160 aaa ttc ctg cag act cag gat gac cgg cct ttc ttc ctc tac gtc gcc      528
Lys Phe Leu Gln Thr Gln Asp Asp Arg Pro Phe Phe Leu Tyr Val Ala
                165                 170                 175 ttc cac gac ccc cac cgc tgt ggg cac tcc cag ccc cag tac gga acc      576
Phe His Asp Pro His Arg Cys Gly His Ser Gln Pro Gln Tyr Gly Thr
                180                 185                 190 ttc tgt gag aag ttt ggc aac gga gag agc ggc atg ggt cgt atc cca      624
Phe Cys Glu Lys Phe Gly Asn Gly Glu Ser Gly Met Gly Arg Ile Pro
                195                 200                 205 gac tgg acc ccc cag gcc tac gac cca ctg gac gtg ctg gtg cct tac      672
Asp Trp Thr Pro Gln Ala Tyr Asp Pro Leu Asp Val Leu Val Pro Tyr
210                 215                 220 ttc gtc ccc aac acc ccg gca gcc cga gcc gac ctg gcc gct cag tac      720
Phe Val Pro Asn Thr Pro Ala Ala Arg Ala Asp Leu Ala Ala Gln Tyr
225                 230                 235                 240 acc acc gtc ggc cgc atg gac caa gga gtt gga ctg gtg ctc cag gag      768
Thr Thr Val Gly Arg Met Asp Gln Gly Val Gly Leu Val Leu Gln Glu
                245                 250                 255 ctg cgt gac gcc ggt gtc ctg aac gac aca ctg gtg atc ttc acg tcc      816
Leu Arg Asp Ala Gly Val Leu Asn Asp Thr Leu Val Ile Phe Thr Ser
                260                 265                 270 gac aac ggg atc ccc ttc ccc agc ggc agg acc aac ctg tac tgg ccg      864
Asp Asn Gly Ile Pro Phe Pro Ser Gly Arg Thr Asn Leu Tyr Trp Pro
                275                 280                 285 ggc act gct gaa ccc tta ctg gtg tca tcc ccg gag cac cca aaa cgc      912
Gly Thr Ala Glu Pro Leu Leu Val Ser Ser Pro Glu His Pro Lys Arg
290                 295                 300 tgg ggc caa gtc agc gag gcc tac gtg agc ctc cta gac ctc acg ccc      960
Trp Gly Gln Val Ser Glu Ala Tyr Val Ser Leu Leu Asp Leu Thr Pro
305                 310                 315                 320 acc atc ttg gat tgg ttc tcg atc ccg tac ccc agc tac gcc atc ttt     1008
Thr Ile Leu Asp Trp Phe Ser Ile Pro Tyr Pro Ser Tyr Ala Ile Phe
                325                 330                 335 ggc tcg aag acc atc cac ctc act ggc cgg tcc ctc ctg ccg gcg ctg     1056
Gly Ser Lys Thr Ile His Leu Thr Gly Arg Ser Leu Leu Pro Ala Leu
                340                 345                 350 gag gcc gag ccc ctc tgg gcc acc gtc ttt ggc agc cag agc cac cac     1104
Glu Ala Glu Pro Leu Trp Ala Thr Val Phe Gly Ser Gln Ser His His
                355                 360                 365 gag gtc acc atg tcc tac ccc atg cgc tcc gtg cag cac cgg cac ttc     1152
Glu Val Thr Met Ser Tyr Pro Met Arg Ser Val Gln His Arg His Phe
                370                 375                 380 cgc ctc gtg cac aac ctc aac ttc aag atg ccc ttt ccc atc gac cag     1200
Arg Leu Val His Asn Leu Asn Phe Lys Met Pro Phe Pro Ile Asp Gln
385                 390                 395                 400 gac ttc tac gtc tca ccc acc ttc cag gac ctc ctg aac cgc acc aca     1248
Asp Phe Tyr Val Ser Pro Thr Phe Gln Asp Leu Leu Asn Arg Thr Thr
                405                 410                 415 gct ggt cag ccc acg ggc tgg tac aag gac ctc cgt cat tac tac tac     1296
Ala Gly Gln Pro Thr Gly Trp Tyr Lys Asp Leu Arg His Tyr Tyr Tyr
```

```
                   420                 425                 430
cgg gcg cgc tgg gag ctc tac gac cgg agc cgg gac ccc cac gag acc      1344
Arg Ala Arg Trp Glu Leu Tyr Asp Arg Ser Arg Asp Pro His Glu Thr
            435                 440                 445 cag aac ctg gcc acc gac ccg cgc ttt gct cag ctt ctg gag atg ctt      1392
Gln Asn Leu Ala Thr Asp Pro Arg Phe Ala Gln Leu Leu Glu Met Leu
450                 455                 460 cgg gac cag ctg gcc aag tgg cag tgg gag acc cac gac ccc tgg gtg      1440
Arg Asp Gln Leu Ala Lys Trp Gln Trp Glu Thr His Asp Pro Trp Val
465                 470                 475                 480 tgc gcc ccc gac ggc gtc ctg gag gag aag ctc tct ccc cag tgc cag      1488
Cys Ala Pro Asp Gly Val Leu Glu Glu Lys Leu Ser Pro Gln Cys Gln
                485                 490                 495 ccc ctc cac aat gag ctg tga                                          1509
Pro Leu His Asn Glu Leu
                500
```

<210> SEQ ID NO 8
<211> LENGTH: 502
<212> TYPE: PRT
<213> ORGANISM: Homo sapiens

<400> SEQUENCE: 8

```
Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
```

```
                    260                 265                 270
Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
        435                 440                 445

Gln Asn Leu Ala Thr Asp Pro Arg Phe Ala Gln Leu Leu Glu Met Leu
    450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 9
<211> LENGTH: 114
<212> TYPE: DNA
<213> ORGANISM: Homo sapiens
<220> FEATURE:
<221> NAME/KEY: CDS
<222> LOCATION: (1)..(114)

<400> SEQUENCE: 9 tct gtc att gat gca ctg cag tac aaa tta gag ggc acc aca aga ttg     48
Ser Val Ile Asp Ala Leu Gln Tyr Lys Leu Glu Gly Thr Thr Arg Leu
1               5                   10                  15 aca aga aaa agg gga ttg aag tta gcc aca gct ctg tct ctg agc aac     96
Thr Arg Lys Arg Gly Leu Lys Leu Ala Thr Ala Leu Ser Leu Ser Asn
            20                  25                  30 aaa ttt gtg gag ggt agt                                            114
Lys Phe Val Glu Gly Ser
        35

<210> SEQ ID NO 10
<211> LENGTH: 38
<212> TYPE: PRT
<213> ORGANISM: Homo sapiens

<400> SEQUENCE: 10

Ser Val Ile Asp Ala Leu Gln Tyr Lys Leu Glu Gly Thr Thr Arg Leu
```

```
1               5                   10                  15
Thr Arg Lys Arg Gly Leu Lys Leu Ala Thr Ala Leu Ser Leu Ser Asn
                20                  25                  30

Lys Phe Val Glu Gly Ser
        35

<210> SEQ ID NO 11
<211> LENGTH: 1611
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1611)

<400> SEQUENCE: 11 atg ccg tct tct gtc tcg tgg ggc atc ctc ctg ctg gca ggc ctg tgc      48
Met Pro Ser Ser Val Ser Trp Gly Ile Leu Leu Leu Ala Gly Leu Cys
1               5                   10                  15 tgc ctg gtc cct gtc tcc ctg gct cgt ccc cgg aac gca ctg ctc ctc      96
Cys Leu Val Pro Val Ser Leu Ala Arg Pro Arg Asn Ala Leu Leu Leu
                20                  25                  30 ctc gcg gat gac gga ggc ttt gag agt ggc gcg tac aac aac agc gcc     144
Leu Ala Asp Asp Gly Gly Phe Glu Ser Gly Ala Tyr Asn Asn Ser Ala
            35                  40                  45 atc gcc acc ccg cac ctg gac gcc ttg gcc cgc cgc agc ctc ctc ttt     192
Ile Ala Thr Pro His Leu Asp Ala Leu Ala Arg Arg Ser Leu Leu Phe
        50                  55                  60 cgc aat gcc ttc acc tcg gtc agc agc tgc tct ccc agc cgc gcc agc     240
Arg Asn Ala Phe Thr Ser Val Ser Ser Cys Ser Pro Ser Arg Ala Ser
65                  70                  75                  80 ctc ctc act ggc ctg ccc cag cat cag aat ggg atg tac ggg ctg cac     288
Leu Leu Thr Gly Leu Pro Gln His Gln Asn Gly Met Tyr Gly Leu His
                85                  90                  95 cag gac gtg cac cac ttc aac tcc ttc gac aag gtg cgg agc ctg ccg     336
Gln Asp Val His His Phe Asn Ser Phe Asp Lys Val Arg Ser Leu Pro
            100                 105                 110 ctg ctg ctc agc caa gct ggt gtg cgc aca ggc atc atc ggg aag aag     384
Leu Leu Leu Ser Gln Ala Gly Val Arg Thr Gly Ile Ile Gly Lys Lys
        115                 120                 125 cac gtg ggg ccg gag acc gtg tac ccg ttt gac ttt gcg tac acg gag     432
His Val Gly Pro Glu Thr Val Tyr Pro Phe Asp Phe Ala Tyr Thr Glu
    130                 135                 140 gag aat ggc tcc gtc ctc cag gtg ggg cgg aac atc act aga att aag     480
Glu Asn Gly Ser Val Leu Gln Val Gly Arg Asn Ile Thr Arg Ile Lys
145                 150                 155                 160 ctg ctc gtc cgg aaa ttc ctg cag act cag gat gac cgg cct ttc ttc     528
Leu Leu Val Arg Lys Phe Leu Gln Thr Gln Asp Asp Arg Pro Phe Phe
                165                 170                 175 ctc tac gtc gcc ttc cac gac ccc cac cgc tgt ggg cac tcc caa ccc     576
Leu Tyr Val Ala Phe His Asp Pro His Arg Cys Gly His Ser Gln Pro
            180                 185                 190 cag tac gga acc ttc tgt gag aag ttt ggc aac gga gag agc ggc atg     624
Gln Tyr Gly Thr Phe Cys Glu Lys Phe Gly Asn Gly Glu Ser Gly Met
        195                 200                 205 ggt cgt atc cca gac tgg acc ccc cag gcc tac gac cca ctg gac gtg     672
Gly Arg Ile Pro Asp Trp Thr Pro Gln Ala Tyr Asp Pro Leu Asp Val
    210                 215                 220 ctg gtg cct tac ttc gtc ccc aac acc ccg gca gcc cga gcc gac ctg     720
Leu Val Pro Tyr Phe Val Pro Asn Thr Pro Ala Ala Arg Ala Asp Leu
```

```
                 225                 230                 235                 240
gcc gct cag tac acc acc gtc ggc cgc atg gac caa gga gtt gga ctg         768
Ala Ala Gln Tyr Thr Thr Val Gly Arg Met Asp Gln Gly Val Gly Leu
                    245                 250                 255 gtg ctc cag gag ctg cgt gac gcc ggt gtc ctg aac gac aca ctg gtg         816
Val Leu Gln Glu Leu Arg Asp Ala Gly Val Leu Asn Asp Thr Leu Val
                260                 265                 270 atc ttc acg tcc gac aac ggg atc ccc ttc ccc agc ggc agg acc aac         864
Ile Phe Thr Ser Asp Asn Gly Ile Pro Phe Pro Ser Gly Arg Thr Asn
            275                 280                 285 ctg tac tgg ccg ggc act gct gaa ccc tta ctg gtg tca tcc ccg gag         912
Leu Tyr Trp Pro Gly Thr Ala Glu Pro Leu Leu Val Ser Ser Pro Glu
        290                 295                 300 cac cca aaa cgc tgg ggc caa gtc agc gag gcc tac gtg agc ctc cta         960
His Pro Lys Arg Trp Gly Gln Val Ser Glu Ala Tyr Val Ser Leu Leu
305                 310                 315                 320 gac ctc acg ccc acc atc ttg gat tgg ttc tcg atc ccg tac ccc agc        1008
Asp Leu Thr Pro Thr Ile Leu Asp Trp Phe Ser Ile Pro Tyr Pro Ser
                    325                 330                 335 tac gcc atc ttt ggc tcg aag acc atc cac ctc act ggc cgg tcc ctc        1056
Tyr Ala Ile Phe Gly Ser Lys Thr Ile His Leu Thr Gly Arg Ser Leu
                340                 345                 350 ctg ccg gcg ctg gag gcc gag ccc ctc tgg gcc acc gtc ttt ggc agc        1104
Leu Pro Ala Leu Glu Ala Glu Pro Leu Trp Ala Thr Val Phe Gly Ser
            355                 360                 365 cag agc cac cac gag gtc acc atg tcc tac ccc atg cgc tcc gtg cag        1152
Gln Ser His His Glu Val Thr Met Ser Tyr Pro Met Arg Ser Val Gln
        370                 375                 380 cac cgg cac ttc cgc ctc gtg cac aac ctc aac ttc aag atg ccc ttt        1200
His Arg His Phe Arg Leu Val His Asn Leu Asn Phe Lys Met Pro Phe
385                 390                 395                 400 ccc atc gac cag gac ttc tac gtc tca ccc acc ttc cag gac ctc ctg        1248
Pro Ile Asp Gln Asp Phe Tyr Val Ser Pro Thr Phe Gln Asp Leu Leu
                    405                 410                 415 aac cgc acc aca gct ggt cag ccc acg ggc tgg tac aag gac ctc cgt        1296
Asn Arg Thr Thr Ala Gly Gln Pro Thr Gly Trp Tyr Lys Asp Leu Arg
                420                 425                 430 cat tac tac tac cgg gcg cgc tgg gag ctc tac gac cgg agc cgg gac        1344
His Tyr Tyr Tyr Arg Ala Arg Trp Glu Leu Tyr Asp Arg Ser Arg Asp
            435                 440                 445 ccc cac gag acc cag aac ctg gcc acc gac ccg cgc ttt gct cag ctt        1392
Pro His Glu Thr Gln Asn Leu Ala Thr Asp Pro Arg Phe Ala Gln Leu
        450                 455                 460 ctg gag atg ctt cgg gac cag ctg gcc aag tgg cag tgg gag acc cac        1440
Leu Glu Met Leu Arg Asp Gln Leu Ala Lys Trp Gln Trp Glu Thr His
465                 470                 475                 480 gac ccc tgg gtg tgc gcc ccc gac ggc gtc ctg gag gag aag ctc tct        1488
Asp Pro Trp Val Cys Ala Pro Asp Gly Val Leu Glu Glu Lys Leu Ser
                    485                 490                 495 ccc cag tgc cag ccc ctc cac aat gag ctg tca tct aga gga tcc cgg        1536
Pro Gln Cys Gln Pro Leu His Asn Glu Leu Ser Ser Arg Gly Ser Arg
                500                 505                 510 gct gac tac aaa gac cat gac ggt gat tat aaa gat cat gac atc gac        1584
Ala Asp Tyr Lys Asp His Asp Gly Asp Tyr Lys Asp His Asp Ile Asp
            515                 520                 525 tac aag gat gac gat gac aag tag tga                                    1611
Tyr Lys Asp Asp Asp Asp Lys
        530                 535
```

```
<210> SEQ ID NO 12
<211> LENGTH: 535
<212> TYPE: PRT
<213> ORGANISM: Artificial Sequence
<220> FEATURE:
<223> OTHER INFORMATION: Synthetic Construct

<400> SEQUENCE: 12
```

| | | | | | | | | | | | | | | |
|---|---|---|---|---|---|---|---|---|---|---|---|---|---|---|
| Met | Pro | Ser | Ser | Val | Ser | Trp | Gly | Ile | Leu | Leu | Ala | Gly | Leu | Cys |
| 1 | | | | 5 | | | | | 10 | | | | | 15 |
| Cys | Leu | Val | Pro | Val | Ser | Leu | Ala | Arg | Pro | Arg | Asn | Ala | Leu | Leu |
| | | | 20 | | | | | 25 | | | | | 30 | |
| Leu | Ala | Asp | Asp | Gly | Gly | Phe | Glu | Ser | Gly | Ala | Tyr | Asn | Asn | Ser | Ala |
| | | 35 | | | | | 40 | | | | | 45 | | |
| Ile | Ala | Thr | Pro | His | Leu | Asp | Ala | Leu | Ala | Arg | Arg | Ser | Leu | Leu | Phe |
| 50 | | | | | 55 | | | | | 60 | | | | |
| Arg | Asn | Ala | Phe | Thr | Ser | Val | Ser | Ser | Cys | Ser | Pro | Ser | Arg | Ala | Ser |
| 65 | | | | | 70 | | | | | 75 | | | | | 80 |
| Leu | Leu | Thr | Gly | Leu | Pro | Gln | His | Gln | Asn | Gly | Met | Tyr | Gly | Leu | His |
| | | | | 85 | | | | | 90 | | | | | 95 | |
| Gln | Asp | Val | His | His | Phe | Asn | Ser | Phe | Asp | Lys | Val | Arg | Ser | Leu | Pro |
| | | | 100 | | | | | 105 | | | | | 110 | | |
| Leu | Leu | Leu | Ser | Gln | Ala | Gly | Val | Arg | Thr | Gly | Ile | Ile | Gly | Lys | Lys |
| | | | 115 | | | | | 120 | | | | | 125 | | |
| His | Val | Gly | Pro | Glu | Thr | Val | Tyr | Pro | Phe | Asp | Phe | Ala | Tyr | Thr | Glu |
| | 130 | | | | | 135 | | | | | 140 | | | | |
| Glu | Asn | Gly | Ser | Val | Leu | Gln | Val | Gly | Arg | Asn | Ile | Thr | Arg | Ile | Lys |
| 145 | | | | | 150 | | | | | 155 | | | | | 160 |
| Leu | Leu | Val | Arg | Lys | Phe | Leu | Gln | Thr | Gln | Asp | Asp | Arg | Pro | Phe | Phe |
| | | | | 165 | | | | | 170 | | | | | 175 | |
| Leu | Tyr | Val | Ala | Phe | His | Asp | Pro | His | Arg | Cys | Gly | His | Ser | Gln | Pro |
| | | | | 180 | | | | | 185 | | | | | 190 | |
| Gln | Tyr | Gly | Thr | Phe | Cys | Glu | Lys | Phe | Gly | Asn | Gly | Glu | Ser | Gly | Met |
| | | | 195 | | | | | 200 | | | | | 205 | | |
| Gly | Arg | Ile | Pro | Asp | Trp | Thr | Pro | Gln | Ala | Tyr | Asp | Pro | Leu | Asp | Val |
| | 210 | | | | | 215 | | | | | 220 | | | | |
| Leu | Val | Pro | Tyr | Phe | Val | Pro | Asn | Thr | Pro | Ala | Ala | Arg | Ala | Asp | Leu |
| 225 | | | | | 230 | | | | | 235 | | | | | 240 |
| Ala | Ala | Gln | Tyr | Thr | Thr | Val | Gly | Arg | Met | Asp | Gln | Gly | Val | Gly | Leu |
| | | | | 245 | | | | | 250 | | | | | 255 | |
| Val | Leu | Gln | Glu | Leu | Arg | Asp | Ala | Gly | Val | Leu | Asn | Asp | Thr | Leu | Val |
| | | | 260 | | | | | 265 | | | | | 270 | | |
| Ile | Phe | Thr | Ser | Asp | Asn | Gly | Ile | Pro | Phe | Pro | Ser | Gly | Arg | Thr | Asn |
| | | | 275 | | | | | 280 | | | | | 285 | | |
| Leu | Tyr | Trp | Pro | Gly | Thr | Ala | Glu | Pro | Leu | Leu | Val | Ser | Ser | Pro | Glu |
| | 290 | | | | | 295 | | | | | 300 | | | | |
| His | Pro | Lys | Arg | Trp | Gly | Gln | Val | Ser | Glu | Ala | Tyr | Val | Ser | Leu | Leu |
| 305 | | | | | 310 | | | | | 315 | | | | | 320 |
| Asp | Leu | Thr | Pro | Thr | Ile | Leu | Asp | Trp | Phe | Ser | Ile | Pro | Tyr | Pro | Ser |
| | | | | 325 | | | | | 330 | | | | | 335 | |
| Tyr | Ala | Ile | Phe | Gly | Ser | Lys | Thr | Ile | His | Leu | Thr | Gly | Arg | Ser | Leu |
| | | | 340 | | | | | 345 | | | | | 350 | | |
| Leu | Pro | Ala | Leu | Glu | Ala | Glu | Pro | Leu | Trp | Ala | Thr | Val | Phe | Gly | Ser |
| | | 355 | | | | | 360 | | | | | 365 | | | |
| Gln | Ser | His | His | Glu | Val | Thr | Met | Ser | Tyr | Pro | Met | Arg | Ser | Val | Gln |

```
                   370                 375                 380
His Arg His Phe Arg Leu Val His Asn Leu Asn Phe Lys Met Pro Phe
385                 390                 395                 400

Pro Ile Asp Gln Asp Phe Tyr Val Ser Pro Thr Phe Gln Asp Leu Leu
                    405                 410                 415

Asn Arg Thr Thr Ala Gly Gln Pro Thr Gly Trp Tyr Lys Asp Leu Arg
                420                 425                 430

His Tyr Tyr Tyr Arg Ala Arg Trp Glu Leu Tyr Asp Arg Ser Arg Asp
            435                 440                 445

Pro His Glu Thr Gln Asn Leu Ala Thr Asp Pro Arg Phe Ala Gln Leu
        450                 455                 460

Leu Glu Met Leu Arg Asp Gln Leu Ala Lys Trp Gln Trp Glu Thr His
465                 470                 475                 480

Asp Pro Trp Val Cys Ala Pro Asp Gly Val Leu Glu Glu Lys Leu Ser
                    485                 490                 495

Pro Gln Cys Gln Pro Leu His Asn Glu Leu Ser Ser Arg Gly Ser Arg
                500                 505                 510

Ala Asp Tyr Lys Asp His Asp Gly Asp Tyr Lys Asp His Asp Ile Asp
            515                 520                 525

Tyr Lys Asp Asp Asp Asp Lys
        530                 535

<210> SEQ ID NO 13
<211> LENGTH: 1614
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1614)

<400> SEQUENCE: 13 atg ccc ccg ccc cgc acc ggc cgc ggc ctg ctg tgg ctg ggc ctg gtg     48
Met Pro Pro Pro Arg Thr Gly Arg Gly Leu Leu Trp Leu Gly Leu Val
1               5                   10                  15 ctg agc agc gtg tgc gtg gcc ctg ggc cgt ccc cgg aac gca ctg ctg     96
Leu Ser Ser Val Cys Val Ala Leu Gly Arg Pro Arg Asn Ala Leu Leu
                20                  25                  30 ctc ctc gcg gat gac gga ggc ttt gag agt ggc gcg tac aac aac agc    144
Leu Leu Ala Asp Asp Gly Gly Phe Glu Ser Gly Ala Tyr Asn Asn Ser
            35                  40                  45 gcc atc gcc acc ccg cac ctg gac gcc ttg gcc cgc cgc agc ctc ctc    192
Ala Ile Ala Thr Pro His Leu Asp Ala Leu Ala Arg Arg Ser Leu Leu
        50                  55                  60 ttt cgc aat gcc ttc acc tcg gtc agc agc tgc tct ccc agc cgc gcc    240
Phe Arg Asn Ala Phe Thr Ser Val Ser Ser Cys Ser Pro Ser Arg Ala
65                  70                  75                  80 agc ctc ctc act ggc ctg ccc cag cat cag aat ggg atg tac ggg ctg    288
Ser Leu Leu Thr Gly Leu Pro Gln His Gln Asn Gly Met Tyr Gly Leu
                85                  90                  95 cac cag gac gtg cac cac ttc aac tcc ttc gac aag gtg cgg agc ctg    336
His Gln Asp Val His His Phe Asn Ser Phe Asp Lys Val Arg Ser Leu
                100                 105                 110 ccg ctg ctg ctc agc caa gct ggt gtg cgc aca ggc atc atc ggg aag    384
Pro Leu Leu Leu Ser Gln Ala Gly Val Arg Thr Gly Ile Ile Gly Lys
            115                 120                 125 aag cac gtg ggg ccg gag acc gtg tac ccg ttt gac ttt gcg tac acg    432
Lys His Val Gly Pro Glu Thr Val Tyr Pro Phe Asp Phe Ala Tyr Thr
```

-continued

```
                    130                 135                 140
gag gag aat ggc tcc gtc ctc cag gtg ggg cgg aac atc act aga att       480
Glu Glu Asn Gly Ser Val Leu Gln Val Gly Arg Asn Ile Thr Arg Ile
145                 150                 155                 160 aag ctg ctc gtc cgg aaa ttc ctg cag act cag gat gac cgg cct ttc       528
Lys Leu Leu Val Arg Lys Phe Leu Gln Thr Gln Asp Asp Arg Pro Phe
                165                 170                 175 ttc ctc tac gtc gcc ttc cac gac ccc cac cgc tgt ggg cac tcc caa       576
Phe Leu Tyr Val Ala Phe His Asp Pro His Arg Cys Gly His Ser Gln
            180                 185                 190 ccc cag tac gga acc ttc tgt gag aag ttt ggc aac gga gag agc ggc       624
Pro Gln Tyr Gly Thr Phe Cys Glu Lys Phe Gly Asn Gly Glu Ser Gly
        195                 200                 205 atg ggt cgt atc cca gac tgg acc ccc cag gcc tac gac cca ctg gac       672
Met Gly Arg Ile Pro Asp Trp Thr Pro Gln Ala Tyr Asp Pro Leu Asp
210                 215                 220 gtg ctg gtg cct tac ttc gtc ccc aac acc ccg gca gcc cga gcc gac       720
Val Leu Val Pro Tyr Phe Val Pro Asn Thr Pro Ala Ala Arg Ala Asp
225                 230                 235                 240 ctg gcc gct cag tac acc acc gtc ggc cgc atg gac caa gga gtt gga       768
Leu Ala Ala Gln Tyr Thr Thr Val Gly Arg Met Asp Gln Gly Val Gly
                245                 250                 255 ctg gtg ctc cag gag ctg cgt gac gcc ggt gtc ctg aac gac aca ctg       816
Leu Val Leu Gln Glu Leu Arg Asp Ala Gly Val Leu Asn Asp Thr Leu
            260                 265                 270 gtg atc ttc acg tcc gac aac ggg atc ccc ttc ccc agc ggc agg acc       864
Val Ile Phe Thr Ser Asp Asn Gly Ile Pro Phe Pro Ser Gly Arg Thr
        275                 280                 285 aac ctg tac tgg ccg ggc act gct gaa ccc tta ctg gtg tca tcc ccg       912
Asn Leu Tyr Trp Pro Gly Thr Ala Glu Pro Leu Leu Val Ser Ser Pro
    290                 295                 300 gag cac cca aaa cgc tgg ggc caa gtc agc gag gcc tac gtg agc ctc       960
Glu His Pro Lys Arg Trp Gly Gln Val Ser Glu Ala Tyr Val Ser Leu
305                 310                 315                 320 cta gac ctc acg ccc acc atc ttg gat tgg ttc tcg atc ccg tac ccc      1008
Leu Asp Leu Thr Pro Thr Ile Leu Asp Trp Phe Ser Ile Pro Tyr Pro
                325                 330                 335 agc tac gcc atc ttt ggc tcg aag acc atc cac ctc act ggc cgg tcc      1056
Ser Tyr Ala Ile Phe Gly Ser Lys Thr Ile His Leu Thr Gly Arg Ser
            340                 345                 350 ctc ctg ccg gcg ctg gag gcc gag ccc ctc tgg gcc acc gtc ttt ggc      1104
Leu Leu Pro Ala Leu Glu Ala Glu Pro Leu Trp Ala Thr Val Phe Gly
        355                 360                 365 agc cag agc cac cac gag gtg acc atg tcc tac ccc atg cgc tcc gtg      1152
Ser Gln Ser His His Glu Val Thr Met Ser Tyr Pro Met Arg Ser Val
    370                 375                 380 cag cac cgg cac ttc cgc ctc gtg cac aac ctc aac ttc aag atg ccc      1200
Gln His Arg His Phe Arg Leu Val His Asn Leu Asn Phe Lys Met Pro
385                 390                 395                 400 ttt ccc atc gac cag gac ttc tac gtc tca ccc acc ttc cag gac ctc      1248
Phe Pro Ile Asp Gln Asp Phe Tyr Val Ser Pro Thr Phe Gln Asp Leu
                405                 410                 415 ctg aac cgc acc aca gct ggt cag ccc acg ggc tgg tac aag gac ctc      1296
Leu Asn Arg Thr Thr Ala Gly Gln Pro Thr Gly Trp Tyr Lys Asp Leu
            420                 425                 430 cgt cat tac tac tac cgg gcg cgc tgg gag ctc tac gac cgg agc cgg      1344
Arg His Tyr Tyr Tyr Arg Ala Arg Trp Glu Leu Tyr Asp Arg Ser Arg
        435                 440                 445 gac ccc cac gag acc cag aac ctg gcc acc gac ccg cgc ttt gct cag      1392
```

-continued

```
Asp Pro His Glu Thr Gln Asn Leu Ala Thr Asp Pro Arg Phe Ala Gln
    450                 455                 460 ctt ctg gag atg ctt cgg gac cag ctg gcc aag tgg cag tgg gag acc      1440
Leu Leu Glu Met Leu Arg Asp Gln Leu Ala Lys Trp Gln Trp Glu Thr
465                 470                 475                 480 cac gac ccc tgg gtg tgc gcc ccc gac ggc gtc ctg gag gag aag ctc      1488
His Asp Pro Trp Val Cys Ala Pro Asp Gly Val Leu Glu Glu Lys Leu
                485                 490                 495 tct ccc cag tgc cag ccc cta cac aat gag ctc tca tct aga gga tcc      1536
Ser Pro Gln Cys Gln Pro Leu His Asn Glu Leu Ser Ser Arg Gly Ser
            500                 505                 510 cgg gct gac tac aaa gac cat gac ggt gat tat aaa gat cat gac atc      1584
Arg Ala Asp Tyr Lys Asp His Asp Gly Asp Tyr Lys Asp His Asp Ile
        515                 520                 525 gac tac aag gat gac gat gac aag tag tga                              1614
Asp Tyr Lys Asp Asp Asp Asp Lys
    530                 535

<210> SEQ ID NO 14
<211> LENGTH: 536
<212> TYPE: PRT
<213> ORGANISM: Artificial Sequence
<220> FEATURE:
<223> OTHER INFORMATION: Synthetic Construct

<400> SEQUENCE: 14

Met Pro Pro Pro Arg Thr Gly Arg Gly Leu Leu Trp Leu Gly Leu Val
1               5                   10                  15

Leu Ser Ser Val Cys Val Ala Leu Gly Arg Pro Arg Asn Ala Leu Leu
                20                  25                  30

Leu Leu Ala Asp Asp Gly Gly Phe Glu Ser Gly Ala Tyr Asn Asn Ser
            35                  40                  45

Ala Ile Ala Thr Pro His Leu Asp Ala Leu Ala Arg Arg Ser Leu Leu
        50                  55                  60

Phe Arg Asn Ala Phe Thr Ser Val Ser Ser Cys Ser Pro Ser Arg Ala
65                  70                  75                  80

Ser Leu Leu Thr Gly Leu Pro Gln His Gln Asn Gly Met Tyr Gly Leu
                85                  90                  95

His Gln Asp Val His His Phe Asn Ser Phe Asp Lys Val Arg Ser Leu
            100                 105                 110

Pro Leu Leu Leu Ser Gln Ala Gly Val Arg Thr Gly Ile Ile Gly Lys
        115                 120                 125

Lys His Val Gly Pro Glu Thr Val Tyr Pro Phe Asp Phe Ala Tyr Thr
    130                 135                 140

Glu Glu Asn Gly Ser Val Leu Gln Val Gly Arg Asn Ile Thr Arg Ile
145                 150                 155                 160

Lys Leu Leu Val Arg Lys Phe Leu Gln Thr Gln Asp Asp Arg Pro Phe
                165                 170                 175

Phe Leu Tyr Val Ala Phe His Asp Pro His Arg Cys Gly His Ser Gln
            180                 185                 190

Pro Gln Tyr Gly Thr Phe Cys Glu Lys Phe Gly Asn Gly Glu Ser Gly
        195                 200                 205

Met Gly Arg Ile Pro Asp Trp Thr Pro Gln Ala Tyr Asp Pro Leu Asp
    210                 215                 220

Val Leu Val Pro Tyr Phe Val Pro Asn Thr Pro Ala Ala Arg Ala Asp
225                 230                 235                 240

Leu Ala Ala Gln Tyr Thr Thr Val Gly Arg Met Asp Gln Gly Val Gly
```

```
                    245                 250                 255
Leu Val Leu Gln Glu Leu Arg Asp Ala Gly Val Leu Asn Asp Thr Leu
                260                 265                 270

Val Ile Phe Thr Ser Asp Asn Gly Ile Pro Phe Pro Ser Gly Arg Thr
            275                 280                 285

Asn Leu Tyr Trp Pro Gly Thr Ala Glu Pro Leu Leu Val Ser Ser Pro
        290                 295                 300

Glu His Pro Lys Arg Trp Gly Gln Val Ser Glu Ala Tyr Val Ser Leu
305                 310                 315                 320

Leu Asp Leu Thr Pro Thr Ile Leu Asp Trp Phe Ser Ile Pro Tyr Pro
                325                 330                 335

Ser Tyr Ala Ile Phe Gly Ser Lys Thr Ile His Leu Thr Gly Arg Ser
            340                 345                 350

Leu Leu Pro Ala Leu Glu Ala Glu Pro Leu Trp Ala Thr Val Phe Gly
        355                 360                 365

Ser Gln Ser His His Glu Val Thr Met Ser Tyr Pro Met Arg Ser Val
    370                 375                 380

Gln His Arg His Phe Arg Leu Val His Asn Leu Asn Phe Lys Met Pro
385                 390                 395                 400

Phe Pro Ile Asp Gln Asp Phe Tyr Val Ser Pro Thr Phe Gln Asp Leu
                405                 410                 415

Leu Asn Arg Thr Thr Ala Gly Gln Pro Thr Gly Trp Tyr Lys Asp Leu
            420                 425                 430

Arg His Tyr Tyr Tyr Arg Ala Arg Trp Glu Leu Tyr Asp Arg Ser Arg
        435                 440                 445

Asp Pro His Glu Thr Gln Asn Leu Ala Thr Asp Pro Arg Phe Ala Gln
    450                 455                 460

Leu Leu Glu Met Leu Arg Asp Gln Leu Ala Lys Trp Gln Trp Glu Thr
465                 470                 475                 480

His Asp Pro Trp Val Cys Ala Pro Asp Gly Val Leu Glu Glu Lys Leu
                485                 490                 495

Ser Pro Gln Cys Gln Pro Leu His Asn Glu Leu Ser Ser Arg Gly Ser
            500                 505                 510

Arg Ala Asp Tyr Lys Asp His Asp Gly Asp Tyr Lys Asp His Asp Ile
        515                 520                 525

Asp Tyr Lys Asp Asp Asp Lys
    530                 535

<210> SEQ ID NO 15
<211> LENGTH: 1734
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1734)

<400> SEQUENCE: 15 atg ccg tct tct gtc tcg tgg ggc atc ctc ctg ctg gca ggc ctg tgc      48
Met Pro Ser Ser Val Ser Trp Gly Ile Leu Leu Leu Ala Gly Leu Cys
1               5                   10                  15 tgc ctg gtc cct gtc tcc ctg gct cgt ccc cgg aac gca ctg ctg ctc      96
Cys Leu Val Pro Val Ser Leu Ala Arg Pro Arg Asn Ala Leu Leu Leu
            20                  25                  30 ctc gcg gat gac gga ggc ttt gag agt ggc gcg tac aac aac agc gcc     144
Leu Ala Asp Asp Gly Gly Phe Glu Ser Gly Ala Tyr Asn Asn Ser Ala
```

-continued

```
              35                  40                  45
atc gcc acc ccg cac ctg gac gcc ttg gcc cgc cgc agc ctc ctc ttt    192
Ile Ala Thr Pro His Leu Asp Ala Leu Ala Arg Arg Ser Leu Leu Phe
 50                  55                  60 cgc aat gcc ttc acc tcg gtc agc agc tgc tct ccc agc cgc gcc agc    240
Arg Asn Ala Phe Thr Ser Val Ser Ser Cys Ser Pro Ser Arg Ala Ser
 65                  70                  75                  80 ctc ctc act ggc ctg ccc cag cat cag aat ggg atg tac ggg ctg cac    288
Leu Leu Thr Gly Leu Pro Gln His Gln Asn Gly Met Tyr Gly Leu His
                 85                  90                  95 cag gac gtg cac cac ttc aac tcc ttc gac aag gtg cgg agc ctg ccg    336
Gln Asp Val His His Phe Asn Ser Phe Asp Lys Val Arg Ser Leu Pro
            100                 105                 110 ctg ctg ctc agc caa gct ggt gtg cgc aca ggc atc atc ggg aag aag    384
Leu Leu Leu Ser Gln Ala Gly Val Arg Thr Gly Ile Ile Gly Lys Lys
        115                 120                 125 cac gtg ggg ccg gag acc gtg tac ccg ttt gac ttt gcg tac acg gag    432
His Val Gly Pro Glu Thr Val Tyr Pro Phe Asp Phe Ala Tyr Thr Glu
    130                 135                 140 gag aat ggc tcc gtc ctc cag gtg ggg cgg aac atc act aga att aag    480
Glu Asn Gly Ser Val Leu Gln Val Gly Arg Asn Ile Thr Arg Ile Lys
145                 150                 155                 160 ctg ctc gtc cgg aaa ttc ctg cag act cag gat gac cgg cct ttc ttc    528
Leu Leu Val Arg Lys Phe Leu Gln Thr Gln Asp Asp Arg Pro Phe Phe
                165                 170                 175 ctc tac gtc gcc ttc cac gac ccc cac cgc tgt ggg cac tcc caa ccc    576
Leu Tyr Val Ala Phe His Asp Pro His Arg Cys Gly His Ser Gln Pro
            180                 185                 190 cag tac gga acc ttc tgt gag aag ttt ggc aac gga gag agc ggc atg    624
Gln Tyr Gly Thr Phe Cys Glu Lys Phe Gly Asn Gly Glu Ser Gly Met
        195                 200                 205 ggt cgt atc cca gac tgg acc ccc cag gcc tac gac cca ctg gac gtg    672
Gly Arg Ile Pro Asp Trp Thr Pro Gln Ala Tyr Asp Pro Leu Asp Val
    210                 215                 220 ctg gtg cct tac ttc gtc ccc aac acc ccg gca gcc cga gcc gac ctg    720
Leu Val Pro Tyr Phe Val Pro Asn Thr Pro Ala Ala Arg Ala Asp Leu
225                 230                 235                 240 gcc gct cag tac acc acc gtc ggc cgc atg gac caa gga gtt gga ctg    768
Ala Ala Gln Tyr Thr Thr Val Gly Arg Met Asp Gln Gly Val Gly Leu
                245                 250                 255 gtg ctc cag gag ctg cgt gac gcc ggt gtc ctg aac gac aca ctg gtg    816
Val Leu Gln Glu Leu Arg Asp Ala Gly Val Leu Asn Asp Thr Leu Val
            260                 265                 270 atc ttc acg tcc gac aac ggg atc ccc ttc ccc agc ggc agg acc aac    864
Ile Phe Thr Ser Asp Asn Gly Ile Pro Phe Pro Ser Gly Arg Thr Asn
        275                 280                 285 ctg tac tgg ccg ggc act gct gaa ccc tta ctg gtg tca tcc ccg gag    912
Leu Tyr Trp Pro Gly Thr Ala Glu Pro Leu Leu Val Ser Ser Pro Glu
    290                 295                 300 cac cca aaa cgc tgg ggc caa gtc agc gag gcc tac gtg agc ctc cta    960
His Pro Lys Arg Trp Gly Gln Val Ser Glu Ala Tyr Val Ser Leu Leu
305                 310                 315                 320 gac ctc acg ccc acc atc ttg gat tgg ttc tcg atc ccg tac ccc agc    1008
Asp Leu Thr Pro Thr Ile Leu Asp Trp Phe Ser Ile Pro Tyr Pro Ser
                325                 330                 335 tac gcc atc ttt ggc tcg aag acc atc cac ctc act ggc cgg tcc ctc    1056
Tyr Ala Ile Phe Gly Ser Lys Thr Ile His Leu Thr Gly Arg Ser Leu
            340                 345                 350 ctg ccg gcg ctg gag gcc gag ccc ctc tgg gcc acc gtc ttt ggc agc    1104
Leu Pro Ala Leu Glu Ala Glu Pro Leu Trp Ala Thr Val Phe Gly Ser
```

```
                                    -continued

Leu Pro Ala Leu Glu Ala Glu Pro Leu Trp Ala Thr Val Phe Gly Ser
                355                 360                 365 cag agc cac cac gag gtc acc atg tct tac ccc atg cgc tcc gtg cag       1152
Gln Ser His His Glu Val Thr Met Ser Tyr Pro Met Arg Ser Val Gln
    370                 375                 380 cac cgg cac ttc cgc ctc gtg cac aac ctc aac ttc aag atg ccc ttt       1200
His Arg His Phe Arg Leu Val His Asn Leu Asn Phe Lys Met Pro Phe
385                 390                 395                 400 ccc atc gac cag gac ttc tac gtc tca ccc acc ttc cag gac ctc ctg       1248
Pro Ile Asp Gln Asp Phe Tyr Val Ser Pro Thr Phe Gln Asp Leu Leu
                405                 410                 415 aac cgc acc aca gct ggt cag ccc acg ggc tgg tac aag gac ctc cgt       1296
Asn Arg Thr Thr Ala Gly Gln Pro Thr Gly Trp Tyr Lys Asp Leu Arg
            420                 425                 430 cat tac tac tac cgg gcg cgc tgg gag ctc tac gac cgg agc cgg gac       1344
His Tyr Tyr Tyr Arg Ala Arg Trp Glu Leu Tyr Asp Arg Ser Arg Asp
        435                 440                 445 ccc cac gag acc cag aac ctg gcc acc gac ccg cgc ttt gct cag ctt       1392
Pro His Glu Thr Gln Asn Leu Ala Thr Asp Pro Arg Phe Ala Gln Leu
    450                 455                 460 ctg gag atg ctt cgg gac cag ctg gcc aag tgg cag tgg gag acc cac       1440
Leu Glu Met Leu Arg Asp Gln Leu Ala Lys Trp Gln Trp Glu Thr His
465                 470                 475                 480 gac ccc tgg gtg tgc gcc ccc gac ggc gtc ctg gag gag aag ctc tct       1488
Asp Pro Trp Val Cys Ala Pro Asp Gly Val Leu Glu Glu Lys Leu Ser
                485                 490                 495 ccc cag tgc cag ccc ctc cac aat gag ctg tca tct aga gga tcc cgg       1536
Pro Gln Cys Gln Pro Leu His Asn Glu Leu Ser Ser Arg Gly Ser Arg
            500                 505                 510 gct gac tac aaa gac cat gac ggt gat tat aaa gat cat gac atc gac       1584
Ala Asp Tyr Lys Asp His Asp Gly Asp Tyr Lys Asp His Asp Ile Asp
        515                 520                 525 tac aag gat gac gat gac aag atc tct gtc att gat gca ctg cag tac       1632
Tyr Lys Asp Asp Asp Asp Lys Ile Ser Val Ile Asp Ala Leu Gln Tyr
    530                 535                 540 aaa tta gag ggc acc aca aga ttg aca aga aaa agg gga ttg aag tta       1680
Lys Leu Glu Gly Thr Thr Arg Leu Thr Arg Lys Arg Gly Leu Lys Leu
545                 550                 555                 560 gcc aca gct ctg tct ctg agc aac aaa ttt gtg gag ggt agt aga tct       1728
Ala Thr Ala Leu Ser Leu Ser Asn Lys Phe Val Glu Gly Ser Arg Ser
                565                 570                 575 tag tga                                                               1734

<210> SEQ ID NO 16
<211> LENGTH: 576
<212> TYPE: PRT
<213> ORGANISM: Artificial Sequence
<220> FEATURE:
<223> OTHER INFORMATION: Synthetic Construct

<400> SEQUENCE: 16

Met Pro Ser Ser Val Ser Trp Gly Ile Leu Leu Leu Ala Gly Leu Cys
1               5                   10                  15

Cys Leu Val Pro Val Ser Leu Ala Arg Pro Arg Asn Ala Leu Leu Leu
            20                  25                  30

Leu Ala Asp Asp Gly Gly Phe Glu Ser Gly Ala Tyr Asn Asn Ser Ala
        35                  40                  45

Ile Ala Thr Pro His Leu Asp Ala Leu Ala Arg Arg Ser Leu Leu Phe
    50                  55                  60
```

```
Arg Asn Ala Phe Thr Ser Val Ser Ser Cys Ser Pro Ser Arg Ala Ser
 65                  70                  75                  80

Leu Leu Thr Gly Leu Pro Gln His Gln Asn Gly Met Tyr Gly Leu His
                 85                  90                  95

Gln Asp Val His His Phe Asn Ser Phe Asp Lys Val Arg Ser Leu Pro
                100                 105                 110

Leu Leu Leu Ser Gln Ala Gly Val Arg Thr Gly Ile Ile Gly Lys Lys
            115                 120                 125

His Val Gly Pro Glu Thr Val Tyr Pro Phe Asp Phe Ala Tyr Thr Glu
        130                 135                 140

Glu Asn Gly Ser Val Leu Gln Val Gly Arg Asn Ile Thr Arg Ile Lys
145                 150                 155                 160

Leu Leu Val Arg Lys Phe Leu Gln Thr Gln Asp Asp Arg Pro Phe Phe
                165                 170                 175

Leu Tyr Val Ala Phe His Asp Pro His Arg Cys Gly His Ser Gln Pro
                180                 185                 190

Gln Tyr Gly Thr Phe Cys Glu Lys Phe Gly Asn Gly Glu Ser Gly Met
            195                 200                 205

Gly Arg Ile Pro Asp Trp Thr Pro Gln Ala Tyr Asp Pro Leu Asp Val
        210                 215                 220

Leu Val Pro Tyr Phe Val Pro Asn Thr Pro Ala Ala Arg Ala Asp Leu
225                 230                 235                 240

Ala Ala Gln Tyr Thr Thr Val Gly Arg Met Asp Gln Gly Val Gly Leu
                245                 250                 255

Val Leu Gln Glu Leu Arg Asp Ala Gly Val Leu Asn Asp Thr Leu Val
            260                 265                 270

Ile Phe Thr Ser Asp Asn Gly Ile Pro Phe Pro Ser Gly Arg Thr Asn
        275                 280                 285

Leu Tyr Trp Pro Gly Thr Ala Glu Pro Leu Leu Val Ser Ser Pro Glu
    290                 295                 300

His Pro Lys Arg Trp Gly Gln Val Ser Glu Ala Tyr Val Ser Leu Leu
305                 310                 315                 320

Asp Leu Thr Pro Thr Ile Leu Asp Trp Phe Ser Ile Pro Tyr Pro Ser
                325                 330                 335

Tyr Ala Ile Phe Gly Ser Lys Thr Ile His Leu Thr Gly Arg Ser Leu
                340                 345                 350

Leu Pro Ala Leu Glu Ala Glu Pro Leu Trp Ala Thr Val Phe Gly Ser
            355                 360                 365

Gln Ser His His Glu Val Thr Met Ser Tyr Pro Met Arg Ser Val Gln
        370                 375                 380

His Arg His Phe Arg Leu Val His Asn Leu Asn Phe Lys Met Pro Phe
385                 390                 395                 400

Pro Ile Asp Gln Asp Phe Tyr Val Ser Pro Thr Phe Gln Asp Leu Leu
                405                 410                 415

Asn Arg Thr Thr Ala Gly Gln Pro Thr Gly Trp Tyr Lys Asp Leu Arg
                420                 425                 430

His Tyr Tyr Tyr Arg Ala Arg Trp Glu Leu Tyr Asp Arg Ser Arg Asp
            435                 440                 445

Pro His Glu Thr Gln Asn Leu Ala Thr Asp Pro Arg Phe Ala Gln Leu
        450                 455                 460

Leu Glu Met Leu Arg Asp Gln Leu Ala Lys Trp Gln Trp Glu Thr His
465                 470                 475                 480

Asp Pro Trp Val Cys Ala Pro Asp Gly Val Leu Glu Glu Lys Leu Ser
```

-continued

```
                       485                 490                 495
Pro Gln Cys Gln Pro Leu His Asn Glu Leu Ser Ser Arg Gly Ser Arg
                500                 505                 510

Ala Asp Tyr Lys Asp His Asp Gly Asp Tyr Lys Asp His Asp Ile Asp
            515                 520                 525

Tyr Lys Asp Asp Asp Asp Lys Ile Ser Val Ile Asp Ala Leu Gln Tyr
        530                 535                 540

Lys Leu Glu Gly Thr Thr Arg Leu Thr Arg Lys Arg Gly Leu Lys Leu
545                 550                 555                 560

Ala Thr Ala Leu Ser Leu Ser Asn Lys Phe Val Glu Gly Ser Arg Ser
                565                 570                 575

<210> SEQ ID NO 17
<211> LENGTH: 1737
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1737)

<400> SEQUENCE: 17 atg ccc ccg ccc cgc acc ggc cgc ggc ctg ctg tgg ctg ggc ctg gtg      48
Met Pro Pro Arg Thr Gly Arg Gly Leu Leu Trp Leu Gly Leu Val
1               5                  10                  15 ctg agc agc gtg tgc gtg gcc ctg ggc cgt ccc cgg aac gca ctg ctg      96
Leu Ser Ser Val Cys Val Ala Leu Gly Arg Pro Arg Asn Ala Leu Leu
                20                  25                  30 ctc ctc gcg gat gac gga ggc ttt gag agt ggc gcg tac aac aac agc     144
Leu Leu Ala Asp Asp Gly Gly Phe Glu Ser Gly Ala Tyr Asn Asn Ser
            35                  40                  45 gcc atc gcc acc ccg cac ctg gac gcc ttg gcc cgc cgc agc ctc ctc     192
Ala Ile Ala Thr Pro His Leu Asp Ala Leu Ala Arg Arg Ser Leu Leu
        50                  55                  60 ttt cgc aat gcc ttc acc tcg gtc agc agc tgc tct ccc agc cgc gcc     240
Phe Arg Asn Ala Phe Thr Ser Val Ser Ser Cys Ser Pro Ser Arg Ala
65                  70                  75                  80 agc ctc ctc act ggc ctg ccc cag cat cag aat ggg atg tac ggg ctg     288
Ser Leu Leu Thr Gly Leu Pro Gln His Gln Asn Gly Met Tyr Gly Leu
                85                  90                  95 cac cag gac gtg cac cac ttc aac tcc ttc gac aag gtg cgg agc ctg     336
His Gln Asp Val His His Phe Asn Ser Phe Asp Lys Val Arg Ser Leu
                100                 105                 110 ccg ctg ctg ctc agc caa gct ggt gtg cgc aca ggc atc atc ggg aag     384
Pro Leu Leu Leu Ser Gln Ala Gly Val Arg Thr Gly Ile Ile Gly Lys
            115                 120                 125 aag cac gtg ggg ccg gag acc gtg tac ccg ttt gac ttt gcg tac acg     432
Lys His Val Gly Pro Glu Thr Val Tyr Pro Phe Asp Phe Ala Tyr Thr
        130                 135                 140 gag gag aat ggc tcc gtc ctc cag gtg ggg cgg aac atc act aga att     480
Glu Glu Asn Gly Ser Val Leu Gln Val Gly Arg Asn Ile Thr Arg Ile
145                 150                 155                 160 aag ctg ctc gtc cgg aaa ttc ctg cag act cag gat gac cgg cct ttc     528
Lys Leu Leu Val Arg Lys Phe Leu Gln Thr Gln Asp Asp Arg Pro Phe
                165                 170                 175 ttc ctc tac gtc gcc ttc cac gac ccc cac cgc tgt ggg cac tcc caa     576
Phe Leu Tyr Val Ala Phe His Asp Pro His Arg Cys Gly His Ser Gln
                180                 185                 190 ccc cag tac gga acc ttc tgt gag aag ttt ggc aac gga gag agc ggc     624
```

```
                Pro Gln Tyr Gly Thr Phe Cys Glu Lys Phe Gly Asn Gly Glu Ser Gly
                        195                 200                 205 atg ggt cgt atc cca gac tgg acc ccc cag gcc tac gac cca ctg gac       672
Met Gly Arg Ile Pro Asp Trp Thr Pro Gln Ala Tyr Asp Pro Leu Asp
    210                 215                 220 gtg ctg gtg cct tac ttc gtc ccc aac acc ccg gca gcc cga gcc gac       720
Val Leu Val Pro Tyr Phe Val Pro Asn Thr Pro Ala Ala Arg Ala Asp
225                 230                 235                 240 ctg gcc gct cag tac acc acc gtc ggc cgc atg gac caa gga gtt gga       768
Leu Ala Ala Gln Tyr Thr Thr Val Gly Arg Met Asp Gln Gly Val Gly
                245                 250                 255 ctg gtg ctc cag gag ctg cgt gac gcc ggt gtc ctg aac gac aca ctg       816
Leu Val Leu Gln Glu Leu Arg Asp Ala Gly Val Leu Asn Asp Thr Leu
        260                 265                 270 gtg atc ttc acg tcc gac aac ggg atc ccc ttc ccc agc ggc agg acc       864
Val Ile Phe Thr Ser Asp Asn Gly Ile Pro Phe Pro Ser Gly Arg Thr
            275                 280                 285 aac ctg tac tgg ccg ggc act gct gaa ccc tta ctg gtg tca tcc ccg       912
Asn Leu Tyr Trp Pro Gly Thr Ala Glu Pro Leu Leu Val Ser Ser Pro
    290                 295                 300 gag cac cca aaa cgc tgg ggc caa gtc agc gag gcc tac gtg agc ctc       960
Glu His Pro Lys Arg Trp Gly Gln Val Ser Glu Ala Tyr Val Ser Leu
305                 310                 315                 320 cta gac ctc acg ccc acc atc ttg gat tgg ttc tcg atc ccg tac ccc      1008
Leu Asp Leu Thr Pro Thr Ile Leu Asp Trp Phe Ser Ile Pro Tyr Pro
                325                 330                 335 agc tac gcc atc ttt ggc tcg aag acc atc cac ctc act ggc cgg tcc      1056
Ser Tyr Ala Ile Phe Gly Ser Lys Thr Ile His Leu Thr Gly Arg Ser
            340                 345                 350 ctc ctg ccg gcg ctg gag gcc gag ccc ctc tgg gcc acc gtc ttt ggc      1104
Leu Leu Pro Ala Leu Glu Ala Glu Pro Leu Trp Ala Thr Val Phe Gly
        355                 360                 365 agc cag agc cac cac gag gtc acc atg tcc tac ccc atg cgc tcc gtg      1152
Ser Gln Ser His His Glu Val Thr Met Ser Tyr Pro Met Arg Ser Val
    370                 375                 380 cag cac cgg cac ttc cgc ctc gtg cac aac ctc aac ttc aag atg ccc      1200
Gln His Arg His Phe Arg Leu Val His Asn Leu Asn Phe Lys Met Pro
385                 390                 395                 400 ttt ccc atc gac cag gac ttc tac gtc tca ccc acc ttc cag gac ctc      1248
Phe Pro Ile Asp Gln Asp Phe Tyr Val Ser Pro Thr Phe Gln Asp Leu
                405                 410                 415 ctg aac cgc acc aca gct ggt cag ccc acg ggc tgg tac aag gac ctc      1296
Leu Asn Arg Thr Thr Ala Gly Gln Pro Thr Gly Trp Tyr Lys Asp Leu
            420                 425                 430 cgt cat tac tac tac cgg gcg cgc tgg gag ctc tac gac cgg agc cgg      1344
Arg His Tyr Tyr Tyr Arg Ala Arg Trp Glu Leu Tyr Asp Arg Ser Arg
        435                 440                 445 gac ccc cac gag acc cag aac ctg gcc acc gac ccg cgc ttt gct cag      1392
Asp Pro His Glu Thr Gln Asn Leu Ala Thr Asp Pro Arg Phe Ala Gln
    450                 455                 460 ctt ctg gag atg ctt cgg gac cag ctg gcc aag tgg cag tgg gag acc      1440
Leu Leu Glu Met Leu Arg Asp Gln Leu Ala Lys Trp Gln Trp Glu Thr
465                 470                 475                 480 cac gac ccc tgg gtg tgc gcc ccc gac ggc gtc ctg gag gag aag ctc      1488
His Asp Pro Trp Val Cys Ala Pro Asp Gly Val Leu Glu Glu Lys Leu
                485                 490                 495 tct ccc cag tgc cag ccc cta cac aat gag ctc tca tct aga gga tcc      1536
Ser Pro Gln Cys Gln Pro Leu His Asn Glu Leu Ser Ser Arg Gly Ser
            500                 505                 510
```

-continued

| | | |
|---|---|---|
| cgg gct gac tac aaa gac cat gac ggt gat tat aaa gat cat gac atc<br>Arg Ala Asp Tyr Lys Asp His Asp Gly Asp Tyr Lys Asp His Asp Ile<br>    515                           520                        525 | | 1584 |
| gac tac aag gat gac gat gac aag atc tct gtc att gat gca ctg cag<br>Asp Tyr Lys Asp Asp Asp Asp Lys Ile Ser Val Ile Asp Ala Leu Gln<br>530                           535                        540 | | 1632 |
| tac aaa tta gag ggc acc aca aga ttg aca aga aaa agg gga ttg aag<br>Tyr Lys Leu Glu Gly Thr Thr Arg Leu Thr Arg Lys Arg Gly Leu Lys<br>545                        550                        555                        560 | | 1680 |
| tta gcc aca gct ctg tct ctg agc aac aaa ttt gtg gag ggt agt aga<br>Leu Ala Thr Ala Leu Ser Leu Ser Asn Lys Phe Val Glu Gly Ser Arg<br>                         565                        570                        575 | | 1728 |
| tct tag tga<br>Ser | | 1737 |

<210> SEQ ID NO 18
<211> LENGTH: 577
<212> TYPE: PRT
<213> ORGANISM: Artificial Sequence
<220> FEATURE:
<223> OTHER INFORMATION: Synthetic Construct

<400> SEQUENCE: 18

Met Pro Pro Pro Arg Thr Gly Arg Gly Leu Leu Trp Leu Gly Leu Val
1               5                   10                  15

Leu Ser Ser Val Cys Val Ala Leu Gly Arg Pro Arg Asn Ala Leu Leu
            20                  25                  30

Leu Leu Ala Asp Asp Gly Gly Phe Glu Ser Gly Ala Tyr Asn Asn Ser
        35                  40                  45

Ala Ile Ala Thr Pro His Leu Asp Ala Leu Ala Arg Arg Ser Leu Leu
    50                  55                  60

Phe Arg Asn Ala Phe Thr Ser Val Ser Ser Cys Ser Pro Ser Arg Ala
65                  70                  75                  80

Ser Leu Leu Thr Gly Leu Pro Gln His Gln Asn Gly Met Tyr Gly Leu
                85                  90                  95

His Gln Asp Val His His Phe Asn Ser Phe Asp Lys Val Arg Ser Leu
            100                 105                 110

Pro Leu Leu Leu Ser Gln Ala Gly Val Arg Thr Gly Ile Ile Gly Lys
        115                 120                 125

Lys His Val Gly Pro Glu Thr Val Tyr Pro Phe Asp Phe Ala Tyr Thr
    130                 135                 140

Glu Glu Asn Gly Ser Val Leu Gln Val Gly Arg Asn Ile Thr Arg Ile
145                 150                 155                 160

Lys Leu Leu Val Arg Lys Phe Leu Gln Thr Gln Asp Asp Arg Pro Phe
                165                 170                 175

Phe Leu Tyr Val Ala Phe His Asp Pro His Arg Cys Gly His Ser Gln
            180                 185                 190

Pro Gln Tyr Gly Thr Phe Cys Glu Lys Phe Gly Asn Gly Glu Ser Gly
        195                 200                 205

Met Gly Arg Ile Pro Asp Trp Thr Pro Gln Ala Tyr Asp Pro Leu Asp
    210                 215                 220

Val Leu Val Pro Tyr Phe Val Pro Asn Thr Pro Ala Ala Arg Ala Asp
225                 230                 235                 240

Leu Ala Ala Gln Tyr Thr Thr Val Gly Arg Met Asp Gln Gly Val Gly
                245                 250                 255

Leu Val Leu Gln Glu Leu Arg Asp Ala Gly Val Leu Asn Asp Thr Leu
            260                 265                 270

Val Ile Phe Thr Ser Asp Asn Gly Ile Pro Phe Pro Ser Gly Arg Thr
    275                 280                 285

Asn Leu Tyr Trp Pro Gly Thr Ala Glu Pro Leu Leu Val Ser Ser Pro
290                 295                 300

Glu His Pro Lys Arg Trp Gly Gln Val Ser Glu Ala Tyr Val Ser Leu
305                 310                 315                 320

Leu Asp Leu Thr Pro Thr Ile Leu Asp Trp Phe Ser Ile Pro Tyr Pro
                325                 330                 335

Ser Tyr Ala Ile Phe Gly Ser Lys Thr Ile His Leu Thr Gly Arg Ser
            340                 345                 350

Leu Leu Pro Ala Leu Glu Ala Glu Pro Leu Trp Ala Thr Val Phe Gly
        355                 360                 365

Ser Gln Ser His His Glu Val Thr Met Ser Tyr Pro Met Arg Ser Val
    370                 375                 380

Gln His Arg His Phe Arg Leu Val His Asn Leu Asn Phe Lys Met Pro
385                 390                 395                 400

Phe Pro Ile Asp Gln Asp Phe Tyr Val Ser Pro Thr Phe Gln Asp Leu
                405                 410                 415

Leu Asn Arg Thr Thr Ala Gly Gln Pro Thr Gly Trp Tyr Lys Asp Leu
            420                 425                 430

Arg His Tyr Tyr Tyr Arg Ala Arg Trp Glu Leu Tyr Asp Arg Ser Arg
        435                 440                 445

Asp Pro His Glu Thr Gln Asn Leu Ala Thr Asp Pro Arg Phe Ala Gln
    450                 455                 460

Leu Leu Glu Met Leu Arg Asp Gln Leu Ala Lys Trp Gln Trp Glu Thr
465                 470                 475                 480

His Asp Pro Trp Val Cys Ala Pro Asp Gly Val Leu Glu Glu Lys Leu
                485                 490                 495

Ser Pro Gln Cys Gln Pro Leu His Asn Glu Leu Ser Ser Arg Gly Ser
            500                 505                 510

Arg Ala Asp Tyr Lys Asp His Asp Gly Asp Tyr Lys Asp His Asp Ile
        515                 520                 525

Asp Tyr Lys Asp Asp Asp Lys Ile Ser Val Ile Asp Ala Leu Gln
    530                 535                 540

Tyr Lys Leu Glu Gly Thr Thr Arg Leu Thr Arg Lys Arg Gly Leu Lys
545                 550                 555                 560

Leu Ala Thr Ala Leu Ser Leu Ser Asn Lys Phe Val Glu Gly Ser Arg
                565                 570                 575

Ser

<210> SEQ ID NO 19
<211> LENGTH: 1521
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1521)

<400> SEQUENCE: 19 atg ccg tct tct gtc tcg tgg ggc atc ctc ctg ctg gca ggc ctg tgc     48
Met Pro Ser Ser Val Ser Trp Gly Ile Leu Leu Leu Ala Gly Leu Cys
1               5                   10                  15 tgc ctg gtc cct gtc tcc ctg gct cgt ccc cgg aac gca ctg ctg ctc     96
Cys Leu Val Pro Val Ser Leu Ala Arg Pro Arg Asn Ala Leu Leu Leu

```
                  20                    25                     30
ctc gcg gat gac gga ggc ttt gag agt ggc gcg tac aac aac agc gcc     144
Leu Ala Asp Asp Gly Gly Phe Glu Ser Gly Ala Tyr Asn Asn Ser Ala
         35                   40                    45 atc gcc acc ccg cac ctg gac gcc ttg gcc cgc cgc agc ctc ctc ttt     192
Ile Ala Thr Pro His Leu Asp Ala Leu Ala Arg Arg Ser Leu Leu Phe
 50                   55                    60 cgc aat gcc ttc acc tcg gtc agc agc tgc tct ccc agc cgc gcc agc     240
Arg Asn Ala Phe Thr Ser Val Ser Ser Cys Ser Pro Ser Arg Ala Ser
 65                   70                    75                    80 ctc ctc act ggc ctg ccc cag cat cag aat ggg atg tac ggg ctg cac     288
Leu Leu Thr Gly Leu Pro Gln His Gln Asn Gly Met Tyr Gly Leu His
                 85                    90                    95 cag gac gtg cac cac ttc aac tcc ttc gac aag gtg cgg agc ctg ccg     336
Gln Asp Val His His Phe Asn Ser Phe Asp Lys Val Arg Ser Leu Pro
                100                   105                   110 ctg ctc ctc agc caa gct ggt gtg cgc aca ggc atc atc ggg aag aag     384
Leu Leu Leu Ser Gln Ala Gly Val Arg Thr Gly Ile Ile Gly Lys Lys
                115                   120                   125 cac gtg ggg ccg gag acc gtg tac ccg ttt gac ttt gcg tac acg gag     432
His Val Gly Pro Glu Thr Val Tyr Pro Phe Asp Phe Ala Tyr Thr Glu
        130                   135                   140 gag aat ggc tcc gtc ctc cag gtg ggg cgg aac atc act aga att aag     480
Glu Asn Gly Ser Val Leu Gln Val Gly Arg Asn Ile Thr Arg Ile Lys
145                   150                   155                   160 ctg ctc gtc cgg aaa ttc ctg cag act cag gat gac cgg cct ttc ttc     528
Leu Leu Val Arg Lys Phe Leu Gln Thr Gln Asp Asp Arg Pro Phe Phe
                165                   170                   175 ctc tac gtc gcc ttc cac gac ccc cac cgc tgt ggg cac tcc caa ccc     576
Leu Tyr Val Ala Phe His Asp Pro His Arg Cys Gly His Ser Gln Pro
                180                   185                   190 cag tac gga acc ttc tgt gag aag ttt ggc aac gga gag agc ggc atg     624
Gln Tyr Gly Thr Phe Cys Glu Lys Phe Gly Asn Gly Glu Ser Gly Met
                195                   200                   205 ggt cgt atc cca gac tgg acc ccc cag gcc tac gac cca ctg gac gtg     672
Gly Arg Ile Pro Asp Trp Thr Pro Gln Ala Tyr Asp Pro Leu Asp Val
        210                   215                   220 ctg gtg cct tac ttc gtc ccc aac acc ccg gca gcc cga gcc gac ctg     720
Leu Val Pro Tyr Phe Val Pro Asn Thr Pro Ala Ala Arg Ala Asp Leu
225                   230                   235                   240 gcc gct cag tac acc acc gtc ggc cgc atg gac caa gga gtt gga ctg     768
Ala Ala Gln Tyr Thr Thr Val Gly Arg Met Asp Gln Gly Val Gly Leu
                245                   250                   255 gtg ctc cag gag ctg cgt gac gcc ggt gtc ctg aac gac aca ctg gtg     816
Val Leu Gln Glu Leu Arg Asp Ala Gly Val Leu Asn Asp Thr Leu Val
                260                   265                   270 atc ttc acg tcc gac aac ggg atc ccc ttc ccc agc ggc agg acc aac     864
Ile Phe Thr Ser Asp Asn Gly Ile Pro Phe Pro Ser Gly Arg Thr Asn
                275                   280                   285 ctg tac tgg ccg ggc act gct gaa ccc tta ctg gtg tca tcc ccg gag     912
Leu Tyr Trp Pro Gly Thr Ala Glu Pro Leu Leu Val Ser Ser Pro Glu
        290                   295                   300 cac cca aaa cgc tgg ggc caa gtc agc gag gcc tac gtg agc ctc cta     960
His Pro Lys Arg Trp Gly Gln Val Ser Glu Ala Tyr Val Ser Leu Leu
305                   310                   315                   320 gac ctc acg ccc acc atc ttg gat tgg ttc tcg atc ccg tac ccc agc     1008
Asp Leu Thr Pro Thr Ile Leu Asp Trp Phe Ser Ile Pro Tyr Pro Ser
                325                   330                   335 tac gcc atc ttt ggc tcg aag acc atc cac ctc act ggc cgg tcc ctc     1056
```

```
Tyr Ala Ile Phe Gly Ser Lys Thr Ile His Leu Thr Gly Arg Ser Leu
                    340                 345                 350 ctg ccg gcg ctg gag gcc gag ccc ctc tgg gcc acc gtc ttt ggc agc    1104
Leu Pro Ala Leu Glu Ala Glu Pro Leu Trp Ala Thr Val Phe Gly Ser
            355                 360                 365 cag agc cac cac gag gtc acc atg tcc tac ccc atg cgc tcc gtg cag    1152
Gln Ser His His Glu Val Thr Met Ser Tyr Pro Met Arg Ser Val Gln
370                 375                 380 cac cgg cac ttc cgc ctc gtg cac aac ctc aac ttc aag atg ccc ttt    1200
His Arg His Phe Arg Leu Val His Asn Leu Asn Phe Lys Met Pro Phe
385                 390                 395                 400 ccc atc gac cag gac ttc tac gtc tca ccc acc ttc cag gac ctc ctg    1248
Pro Ile Asp Gln Asp Phe Tyr Val Ser Pro Thr Phe Gln Asp Leu Leu
                405                 410                 415 aac cgc acc aca gct ggt cag ccc acg ggc tgg tac aag gac ctc cgt    1296
Asn Arg Thr Thr Ala Gly Gln Pro Thr Gly Trp Tyr Lys Asp Leu Arg
            420                 425                 430 cat tac tac tac cgg gcg cgc tgg gag ctc tac gac cgg agc cgg gac    1344
His Tyr Tyr Tyr Arg Ala Arg Trp Glu Leu Tyr Asp Arg Ser Arg Asp
                435                 440                 445 ccc cac gag acc cag aac ctg gcc acc gac ccg cgc ttt gct cag ctt    1392
Pro His Glu Thr Gln Asn Leu Ala Thr Asp Pro Arg Phe Ala Gln Leu
450                 455                 460 ctg gag atg ctt cgg gac cag ctg gcc aag tgg cag tgg gag acc cac    1440
Leu Glu Met Leu Arg Asp Gln Leu Ala Lys Trp Gln Trp Glu Thr His
465                 470                 475                 480 gac ccc tgg gtg tgc gcc ccc gac ggc gtc ctg gag gag aag ctc tct    1488
Asp Pro Trp Val Cys Ala Pro Asp Gly Val Leu Glu Glu Lys Leu Ser
                485                 490                 495 ccc cag tgc cag ccc ctc cac aat gag ctg tga                        1521
Pro Gln Cys Gln Pro Leu His Asn Glu Leu
                500                 505

<210> SEQ ID NO 20
<211> LENGTH: 506
<212> TYPE: PRT
<213> ORGANISM: Artificial Sequence
<220> FEATURE:
<223> OTHER INFORMATION: Synthetic Construct

<400> SEQUENCE: 20

Met Pro Ser Ser Val Ser Trp Gly Ile Leu Leu Leu Ala Gly Leu Cys
1               5                   10                  15

Cys Leu Val Pro Val Ser Leu Ala Arg Pro Arg Asn Ala Leu Leu Leu
            20                  25                  30

Leu Ala Asp Asp Gly Gly Phe Glu Ser Gly Ala Tyr Asn Asn Ser Ala
        35                  40                  45

Ile Ala Thr Pro His Leu Asp Ala Leu Ala Arg Arg Ser Leu Leu Phe
    50                  55                  60

Arg Asn Ala Phe Thr Ser Val Ser Ser Cys Ser Pro Ser Arg Ala Ser
65                  70                  75                  80

Leu Leu Thr Gly Leu Pro Gln His Gln Asn Gly Met Tyr Gly Leu His
                85                  90                  95

Gln Asp Val His His Phe Asn Ser Phe Asp Lys Val Arg Ser Leu Pro
            100                 105                 110

Leu Leu Leu Ser Gln Ala Gly Val Arg Thr Gly Ile Ile Gly Lys Lys
        115                 120                 125

His Val Gly Pro Glu Thr Val Tyr Pro Phe Asp Phe Ala Tyr Thr Glu
    130                 135                 140
```

Glu Asn Gly Ser Val Leu Gln Val Gly Arg Asn Ile Thr Arg Ile Lys
145                 150                 155                 160

Leu Leu Val Arg Lys Phe Leu Gln Thr Gln Asp Arg Pro Phe Phe
            165                 170                 175

Leu Tyr Val Ala Phe His Asp Pro His Arg Cys Gly His Ser Gln Pro
            180                 185                 190

Gln Tyr Gly Thr Phe Cys Glu Lys Phe Gly Asn Gly Glu Ser Gly Met
        195                 200                 205

Gly Arg Ile Pro Asp Trp Thr Pro Gln Ala Tyr Asp Pro Leu Asp Val
        210                 215                 220

Leu Val Pro Tyr Phe Val Pro Asn Thr Pro Ala Ala Arg Ala Asp Leu
225                 230                 235                 240

Ala Ala Gln Tyr Thr Thr Val Gly Arg Met Asp Gln Gly Val Gly Leu
            245                 250                 255

Val Leu Gln Glu Leu Arg Asp Ala Gly Val Leu Asn Asp Thr Leu Val
            260                 265                 270

Ile Phe Thr Ser Asp Asn Gly Ile Pro Phe Pro Ser Gly Arg Thr Asn
        275                 280                 285

Leu Tyr Trp Pro Gly Thr Ala Glu Pro Leu Leu Val Ser Ser Pro Glu
        290                 295                 300

His Pro Lys Arg Trp Gly Gln Val Ser Glu Ala Tyr Val Ser Leu Leu
305                 310                 315                 320

Asp Leu Thr Pro Thr Ile Leu Asp Trp Phe Ser Ile Pro Tyr Pro Ser
            325                 330                 335

Tyr Ala Ile Phe Gly Ser Lys Thr Ile His Leu Thr Gly Arg Ser Leu
            340                 345                 350

Leu Pro Ala Leu Glu Ala Glu Pro Leu Trp Ala Thr Val Phe Gly Ser
        355                 360                 365

Gln Ser His His Glu Val Thr Met Ser Tyr Pro Met Arg Ser Val Gln
        370                 375                 380

His Arg His Phe Arg Leu Val His Asn Leu Asn Phe Lys Met Pro Phe
385                 390                 395                 400

Pro Ile Asp Gln Asp Phe Tyr Val Ser Pro Thr Phe Gln Asp Leu Leu
            405                 410                 415

Asn Arg Thr Thr Ala Gly Gln Pro Thr Gly Trp Tyr Lys Asp Leu Arg
            420                 425                 430

His Tyr Tyr Tyr Arg Ala Arg Trp Glu Leu Tyr Asp Arg Ser Arg Asp
        435                 440                 445

Pro His Glu Thr Gln Asn Leu Ala Thr Asp Pro Arg Phe Ala Gln Leu
        450                 455                 460

Leu Glu Met Leu Arg Asp Gln Leu Ala Lys Trp Gln Trp Glu Thr His
465                 470                 475                 480

Asp Pro Trp Val Cys Ala Pro Asp Gly Val Leu Glu Glu Lys Leu Ser
            485                 490                 495

Pro Gln Cys Gln Pro Leu His Asn Glu Leu
            500                 505

<210> SEQ ID NO 21
<211> LENGTH: 1524
<212> TYPE: DNA
<213> ORGANISM: Artificial Sequence
<220> FEATURE:
<223> OTHER INFORMATION: chimeric sequence
<220> FEATURE:
<221> NAME/KEY: CDS

<222> LOCATION: (1)..(1524)

<400> SEQUENCE: 21

```
atg ccc ccg ccc cgc acc ggc cgc ggc ctg ctg tgg ctg ggc ctg gtg      48
Met Pro Pro Pro Arg Thr Gly Arg Gly Leu Leu Trp Leu Gly Leu Val
1               5                   10                  15 ctg agc agc gtg tgc gtg gcc ctg ggc cgt ccc cgg aac gca ctg ctg      96
Leu Ser Ser Val Cys Val Ala Leu Gly Arg Pro Arg Asn Ala Leu Leu
            20                  25                  30 ctc ctc gcg gat gac gga ggc ttt gag agt ggc gcg tac aac aac agc     144
Leu Leu Ala Asp Asp Gly Gly Phe Glu Ser Gly Ala Tyr Asn Asn Ser
        35                  40                  45 gcc atc gcc acc ccg cac ctg gac gcc ttg gcc cgc cgc agc ctc ctc     192
Ala Ile Ala Thr Pro His Leu Asp Ala Leu Ala Arg Arg Ser Leu Leu
    50                  55                  60 ttt cgc aat gcc ttc acc tcg gtc agc agc tgc tct ccc agc cgc gcc     240
Phe Arg Asn Ala Phe Thr Ser Val Ser Ser Cys Ser Pro Ser Arg Ala
65                  70                  75                  80 agc ctc ctc act ggc ctg ccc cag cat cag aat ggg atg tac ggg ctg     288
Ser Leu Leu Thr Gly Leu Pro Gln His Gln Asn Gly Met Tyr Gly Leu
                85                  90                  95 cac cag gac gtg cac cac ttc aac tcc ttc gac aag gtg cgg agc ctg     336
His Gln Asp Val His His Phe Asn Ser Phe Asp Lys Val Arg Ser Leu
            100                 105                 110 ccg ctg ctg ctc agc caa gct ggt gtg cgc aca ggc atc atc ggg aag     384
Pro Leu Leu Leu Ser Gln Ala Gly Val Arg Thr Gly Ile Ile Gly Lys
        115                 120                 125 aag cac gtg ggg ccg gag acc gtg tac ccg ttt gac ttt gcg tac acg     432
Lys His Val Gly Pro Glu Thr Val Tyr Pro Phe Asp Phe Ala Tyr Thr
    130                 135                 140 gag gag aat ggc tcc gtc ctc cag gtg ggg cgg aac atc act aga att     480
Glu Glu Asn Gly Ser Val Leu Gln Val Gly Arg Asn Ile Thr Arg Ile
145                 150                 155                 160 aag ctg ctc gtc cgg aaa ttc ctg cag act cag gat gac cgg cct ttc     528
Lys Leu Leu Val Arg Lys Phe Leu Gln Thr Gln Asp Asp Arg Pro Phe
                165                 170                 175 ttc ctc tac gtc gcc ttc cac gac ccc cac cgc tgt ggg cac tcc caa     576
Phe Leu Tyr Val Ala Phe His Asp Pro His Arg Cys Gly His Ser Gln
            180                 185                 190 ccc cag tac gga acc ttc tgt gag aag ttt ggc aac gga gag agc ggc     624
Pro Gln Tyr Gly Thr Phe Cys Glu Lys Phe Gly Asn Gly Glu Ser Gly
        195                 200                 205 atg ggt cgt atc cca gac tgg acc ccc cag gcc tac gac cca ctg gac     672
Met Gly Arg Ile Pro Asp Trp Thr Pro Gln Ala Tyr Asp Pro Leu Asp
    210                 215                 220 gtg ctg gtg cct tac ttc gtc ccc aac acc ccg gca gcc cga gcc gac     720
Val Leu Val Pro Tyr Phe Val Pro Asn Thr Pro Ala Ala Arg Ala Asp
225                 230                 235                 240 ctg gcc gct cag tac acc acc gtc ggc cgc atg gac caa gga gtt gga     768
Leu Ala Ala Gln Tyr Thr Thr Val Gly Arg Met Asp Gln Gly Val Gly
                245                 250                 255 ctg gtg ctc cag gag ctg cgt gac gcc ggt gtc ctg aac gac aca ctg     816
Leu Val Leu Gln Glu Leu Arg Asp Ala Gly Val Leu Asn Asp Thr Leu
            260                 265                 270 gtg atc ttc acg tcc gac aac ggg atc ccc ttc ccc agc ggc agg acc     864
Val Ile Phe Thr Ser Asp Asn Gly Ile Pro Phe Pro Ser Gly Arg Thr
        275                 280                 285 aac ctg tac tgg ccg ggc act gct gaa ccc tta ctg gtg tca tcc ccg     912
Asn Leu Tyr Trp Pro Gly Thr Ala Glu Pro Leu Leu Val Ser Ser Pro
    290                 295                 300
```

```
gag cac cca aaa cgc tgg ggc caa gtc agc gag gcc tac gtg agc ctc      960
Glu His Pro Lys Arg Trp Gly Gln Val Ser Glu Ala Tyr Val Ser Leu
305             310                 315                 320 cta gac ctc acg ccc acc atc ttg gat tgg ttc tcg atc ccg tac ccc     1008
Leu Asp Leu Thr Pro Thr Ile Leu Asp Trp Phe Ser Ile Pro Tyr Pro
                325                 330                 335 agc tac gcc atc ttt ggc tcg aag acc atc cac ctc act ggc cgg tcc     1056
Ser Tyr Ala Ile Phe Gly Ser Lys Thr Ile His Leu Thr Gly Arg Ser
            340                 345                 350 ctc ctg ccg gcg ctg gag gcc gag ccc ctc tgg gcc acc gtc ttt ggc     1104
Leu Leu Pro Ala Leu Glu Ala Glu Pro Leu Trp Ala Thr Val Phe Gly
        355                 360                 365 agc cag agc cac cac gag gtc acc atg tcc tac ccc atg cgc tcc gtg     1152
Ser Gln Ser His His Glu Val Thr Met Ser Tyr Pro Met Arg Ser Val
    370                 375                 380 cag cac cgg cac ttc cgc ctc gtg cac aac ctc aac ttc aag atg ccc     1200
Gln His Arg His Phe Arg Leu Val His Asn Leu Asn Phe Lys Met Pro
385                 390                 395                 400 ttt ccc atc gac cag gac ttc tac gtc tca ccc acc ttc cag gac ctc     1248
Phe Pro Ile Asp Gln Asp Phe Tyr Val Ser Pro Thr Phe Gln Asp Leu
                405                 410                 415 ctg aac cgc acc aca gct ggt cag ccc acg ggc tgg tac aag gac ctc     1296
Leu Asn Arg Thr Thr Ala Gly Gln Pro Thr Gly Trp Tyr Lys Asp Leu
            420                 425                 430 cgt cat tac tac tac cgg gcg cgc tgg gag ctc tac gac cgg agc cgg     1344
Arg His Tyr Tyr Tyr Arg Ala Arg Trp Glu Leu Tyr Asp Arg Ser Arg
        435                 440                 445 gac ccc cac gag acc cag aac ctg gcc acc gac ccg cgc ttt gct cag     1392
Asp Pro His Glu Thr Gln Asn Leu Ala Thr Asp Pro Arg Phe Ala Gln
    450                 455                 460 ctt ctg gag atg ctt cgg gac cag ctg gcc aag tgg cag tgg gag acc     1440
Leu Leu Glu Met Leu Arg Asp Gln Leu Ala Lys Trp Gln Trp Glu Thr
465                 470                 475                 480 cac gac ccc tgg gtg tgc gcc ccc gac ggc gtc ctg gag gag aag ctc     1488
His Asp Pro Trp Val Cys Ala Pro Asp Gly Val Leu Glu Glu Lys Leu
                485                 490                 495 tct ccc cag tgc cag ccc cta cac aat gag ctc tga                     1524
Ser Pro Gln Cys Gln Pro Leu His Asn Glu Leu
            500                 505
```

<210> SEQ ID NO 22
<211> LENGTH: 507
<212> TYPE: PRT
<213> ORGANISM: Artificial Sequence
<220> FEATURE:
<223> OTHER INFORMATION: Synthetic Construct

<400> SEQUENCE: 22

```
Met Pro Pro Arg Thr Gly Arg Gly Leu Leu Trp Leu Gly Leu Val
1               5                   10                  15

Leu Ser Ser Val Cys Val Ala Leu Gly Arg Pro Arg Asn Ala Leu Leu
                20                  25                  30

Leu Leu Ala Asp Asp Gly Gly Phe Glu Ser Gly Ala Tyr Asn Asn Ser
            35                  40                  45

Ala Ile Ala Thr Pro His Leu Asp Ala Leu Ala Arg Arg Ser Leu Leu
        50                  55                  60

Phe Arg Asn Ala Phe Thr Ser Val Ser Ser Cys Ser Pro Ser Arg Ala
65                  70                  75                  80

Ser Leu Leu Thr Gly Leu Pro Gln His Gln Asn Gly Met Tyr Gly Leu
```

```
                        85                  90                  95
His Gln Asp Val His His Phe Asn Ser Phe Asp Lys Val Arg Ser Leu
                100                 105                 110
Pro Leu Leu Leu Ser Gln Ala Gly Val Arg Thr Gly Ile Ile Gly Lys
            115                 120                 125
Lys His Val Gly Pro Glu Thr Val Tyr Pro Phe Asp Phe Ala Tyr Thr
        130                 135                 140
Glu Glu Asn Gly Ser Val Leu Gln Val Gly Arg Asn Ile Thr Arg Ile
145                 150                 155                 160
Lys Leu Leu Val Arg Lys Phe Leu Gln Thr Gln Asp Asp Arg Pro Phe
                165                 170                 175
Phe Leu Tyr Val Ala Phe His Asp Pro His Arg Cys Gly His Ser Gln
                180                 185                 190
Pro Gln Tyr Gly Thr Phe Cys Glu Lys Phe Gly Asn Gly Glu Ser Gly
            195                 200                 205
Met Gly Arg Ile Pro Asp Trp Thr Pro Gln Ala Tyr Asp Pro Leu Asp
        210                 215                 220
Val Leu Val Pro Tyr Phe Val Pro Asn Thr Pro Ala Ala Arg Ala Asp
225                 230                 235                 240
Leu Ala Ala Gln Tyr Thr Thr Val Gly Arg Met Asp Gln Gly Val Gly
                245                 250                 255
Leu Val Leu Gln Glu Leu Arg Asp Ala Gly Val Leu Asn Asp Thr Leu
                260                 265                 270
Val Ile Phe Thr Ser Asp Asn Gly Ile Pro Phe Pro Ser Gly Arg Thr
            275                 280                 285
Asn Leu Tyr Trp Pro Gly Thr Ala Glu Pro Leu Leu Val Ser Ser Pro
        290                 295                 300
Glu His Pro Lys Arg Trp Gly Gln Val Ser Glu Ala Tyr Val Ser Leu
305                 310                 315                 320
Leu Asp Leu Thr Pro Thr Ile Leu Asp Trp Phe Ser Ile Pro Tyr Pro
                325                 330                 335
Ser Tyr Ala Ile Phe Gly Ser Lys Thr Ile His Leu Thr Gly Arg Ser
                340                 345                 350
Leu Leu Pro Ala Leu Glu Ala Glu Pro Leu Trp Ala Thr Val Phe Gly
            355                 360                 365
Ser Gln Ser His His Glu Val Thr Met Ser Tyr Pro Met Arg Ser Val
        370                 375                 380
Gln His Arg His Phe Arg Leu Val His Asn Leu Asn Phe Lys Met Pro
385                 390                 395                 400
Phe Pro Ile Asp Gln Asp Phe Tyr Val Ser Pro Thr Phe Gln Asp Leu
                405                 410                 415
Leu Asn Arg Thr Thr Ala Gly Gln Pro Thr Gly Trp Tyr Lys Asp Leu
                420                 425                 430
Arg His Tyr Tyr Tyr Arg Ala Arg Trp Glu Leu Tyr Asp Arg Ser Arg
            435                 440                 445
Asp Pro His Glu Thr Gln Asn Leu Ala Thr Asp Pro Arg Phe Ala Gln
        450                 455                 460
Leu Leu Glu Met Leu Arg Asp Gln Leu Ala Lys Trp Gln Trp Glu Thr
465                 470                 475                 480
His Asp Pro Trp Val Cys Ala Pro Asp Gly Val Leu Glu Glu Lys Leu
                485                 490                 495
Ser Pro Gln Cys Gln Pro Leu His Asn Glu Leu
                500                 505
```

<210> SEQ ID NO 23
<211> LENGTH: 1653
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1653)

<400> SEQUENCE: 23

```
atg ccg tct tct gtc tcg tgg ggc atc ctc ctg ctg gca ggc ctg tgc      48
Met Pro Ser Ser Val Ser Trp Gly Ile Leu Leu Leu Ala Gly Leu Cys
1               5                   10                  15 tgc ctg gtc cct gtc tcc ctg gct cgt ccc cgg aac gca ctg ctg ctc      96
Cys Leu Val Pro Val Ser Leu Ala Arg Pro Arg Asn Ala Leu Leu Leu
                20                  25                  30 ctc gcg gat gac gga ggc ttt gag agt ggc gcg tac aac aac agc gcc     144
Leu Ala Asp Asp Gly Gly Phe Glu Ser Gly Ala Tyr Asn Asn Ser Ala
            35                  40                  45 atc gcc acc ccg cac ctg gac gcc ttg gcc cgc cgc agc ctc ctc ttt     192
Ile Ala Thr Pro His Leu Asp Ala Leu Ala Arg Arg Ser Leu Leu Phe
        50                  55                  60 cgc aat gcc ttc acc tcg gtc agc agc tgc tct ccc agc cgc gcc agc     240
Arg Asn Ala Phe Thr Ser Val Ser Ser Cys Ser Pro Ser Arg Ala Ser
65                  70                  75                  80 ctc ctc act ggc ctg ccc cag cat cag aat ggg atg tac ggg ctg cac     288
Leu Leu Thr Gly Leu Pro Gln His Gln Asn Gly Met Tyr Gly Leu His
                85                  90                  95 cag gac gtg cac cac ttc aac tcc ttc gac aag gtg cgg agc ctg ccg     336
Gln Asp Val His His Phe Asn Ser Phe Asp Lys Val Arg Ser Leu Pro
                100                 105                 110 ctg ctc ctc agc caa gct ggt gtg cgc aca ggc atc atc ggg aag aag     384
Leu Leu Leu Ser Gln Ala Gly Val Arg Thr Gly Ile Ile Gly Lys Lys
            115                 120                 125 cac gtg ggg ccg gag acc gtg tac ccg ttt gac ttt gcg tac acg gag     432
His Val Gly Pro Glu Thr Val Tyr Pro Phe Asp Phe Ala Tyr Thr Glu
        130                 135                 140 gag aat ggc tcc gtc ctc cag gtg ggg cgg aac atc act aga att aag     480
Glu Asn Gly Ser Val Leu Gln Val Gly Arg Asn Ile Thr Arg Ile Lys
145                 150                 155                 160 ctg ctc gtc cgg aaa ttc ctg cag act cag gat gac cgg cct ttc ttc     528
Leu Leu Val Arg Lys Phe Leu Gln Thr Gln Asp Asp Arg Pro Phe Phe
                165                 170                 175 ctc tac gtc gcc ttc cac gac ccc cac cgc tgt ggg cac tcc caa ccc     576
Leu Tyr Val Ala Phe His Asp Pro His Arg Cys Gly His Ser Gln Pro
                180                 185                 190 cag tac gga acc ttc tgt gag aag ttt ggc aac gga gag agc ggc atg     624
Gln Tyr Gly Thr Phe Cys Glu Lys Phe Gly Asn Gly Glu Ser Gly Met
            195                 200                 205 ggt cgt atc cca gac tgg acc ccc cag gcc tac gac cca ctg gac gtg     672
Gly Arg Ile Pro Asp Trp Thr Pro Gln Ala Tyr Asp Pro Leu Asp Val
        210                 215                 220 ctg gtg cct tac ttc gtc ccc aac acc ccg gca gcc cga gcc gac ctg     720
Leu Val Pro Tyr Phe Val Pro Asn Thr Pro Ala Ala Arg Ala Asp Leu
225                 230                 235                 240 gcc gct cag tac acc acc gtc ggc cgc atg gac caa gga gtt gga ctg     768
Ala Ala Gln Tyr Thr Thr Val Gly Arg Met Asp Gln Gly Val Gly Leu
                245                 250                 255 gtg ctc cag gag ctg cgt gac gcc ggt gtc ctg aac gac aca ctg gtg     816
```

```
                Val Leu Gln Glu Leu Arg Asp Ala Gly Val Leu Asn Asp Thr Leu Val
                            260                 265                 270 atc ttc acg tcc gac aac ggg atc ccc ttc ccc agc ggc agg acc aac        864
Ile Phe Thr Ser Asp Asn Gly Ile Pro Phe Pro Ser Gly Arg Thr Asn
            275                 280                 285 ctg tac tgg ccg ggc act gct gaa ccc tta ctg gtg tca tcc ccg gag        912
Leu Tyr Trp Pro Gly Thr Ala Glu Pro Leu Leu Val Ser Ser Pro Glu
290                 295                 300 cac cca aaa cgc tgg ggc caa gtc agc gag gcc tac gtg agc ctc cta        960
His Pro Lys Arg Trp Gly Gln Val Ser Glu Ala Tyr Val Ser Leu Leu
305                 310                 315                 320 gac ctc acg ccc acc atc ttg gat tgg ttc tcg atc ccg tac ccc agc       1008
Asp Leu Thr Pro Thr Ile Leu Asp Trp Phe Ser Ile Pro Tyr Pro Ser
                325                 330                 335 tac gcc atc ttt ggc tcg aag acc atc cac ctc act ggc cgg tcc ctc       1056
Tyr Ala Ile Phe Gly Ser Lys Thr Ile His Leu Thr Gly Arg Ser Leu
            340                 345                 350 ctg ccg gcg ctg gag gcc gag ccc ctc tgg gcc acc gtc ttt ggc agc       1104
Leu Pro Ala Leu Glu Ala Glu Pro Leu Trp Ala Thr Val Phe Gly Ser
        355                 360                 365 cag agc cac cac gag gtc acc atg tct tac ccc atg cgc tcc gtg cag       1152
Gln Ser His His Glu Val Thr Met Ser Tyr Pro Met Arg Ser Val Gln
370                 375                 380 cac cgg cac ttc cgc ctc gtg cac aac ctc aac ttc aag atg ccc ttt       1200
His Arg His Phe Arg Leu Val His Asn Leu Asn Phe Lys Met Pro Phe
385                 390                 395                 400 ccc atc gac cag gac ttc tac gtc tca ccc acc ttc cag gac ctc ctg       1248
Pro Ile Asp Gln Asp Phe Tyr Val Ser Pro Thr Phe Gln Asp Leu Leu
                405                 410                 415 aac cgc acc aca gct ggt cag ccc acg ggc tgg tac aag gac ctc cgt       1296
Asn Arg Thr Thr Ala Gly Gln Pro Thr Gly Trp Tyr Lys Asp Leu Arg
            420                 425                 430 cat tac tac tac cgg gcg cgc tgg gag ctc tac gac cgg agc cgg gac       1344
His Tyr Tyr Tyr Arg Ala Arg Trp Glu Leu Tyr Asp Arg Ser Arg Asp
        435                 440                 445 ccc cac gag acc cag aac ctg gcc acc gac ccg cgc ttt gct cag ctt       1392
Pro His Glu Thr Gln Asn Leu Ala Thr Asp Pro Arg Phe Ala Gln Leu
450                 455                 460 ctg gag atg ctt cgg gac cag ctg gcc aag tgg cag tgg gag acc cac       1440
Leu Glu Met Leu Arg Asp Gln Leu Ala Lys Trp Gln Trp Glu Thr His
465                 470                 475                 480 gac ccc tgg gtg tgc gcc ccc gac ggc gtc ctg gag gag aag ctc tct       1488
Asp Pro Trp Val Cys Ala Pro Asp Gly Val Leu Glu Glu Lys Leu Ser
                485                 490                 495 ccc cag tgc cag ccc ctc cac aat gag ctg tca tct aga tct gtc att       1536
Pro Gln Cys Gln Pro Leu His Asn Glu Leu Ser Ser Arg Ser Val Ile
            500                 505                 510 gat gca ctg cag tac aaa tta gag ggc acc aca aga ttg aca aga aaa       1584
Asp Ala Leu Gln Tyr Lys Leu Glu Gly Thr Thr Arg Leu Thr Arg Lys
        515                 520                 525 agg gga ttg aag tta gcc aca gct ctg tct ctg agc aac aaa ttt gtg       1632
Arg Gly Leu Lys Leu Ala Thr Ala Leu Ser Leu Ser Asn Lys Phe Val
530                 535                 540 gag ggt agt aga tct tag tga                                           1653
Glu Gly Ser Arg Ser
545

<210> SEQ ID NO 24
<211> LENGTH: 549
<212> TYPE: PRT
```

<213> ORGANISM: Artificial Sequence
<220> FEATURE:
<223> OTHER INFORMATION: Synthetic Construct

<400> SEQUENCE: 24

```
Met Pro Ser Ser Val Ser Trp Gly Ile Leu Leu Leu Ala Gly Leu Cys
1               5                   10                  15

Cys Leu Val Pro Val Ser Leu Ala Arg Pro Arg Asn Ala Leu Leu Leu
            20                  25                  30

Leu Ala Asp Asp Gly Gly Phe Glu Ser Gly Ala Tyr Asn Asn Ser Ala
        35                  40                  45

Ile Ala Thr Pro His Leu Asp Ala Leu Ala Arg Arg Ser Leu Leu Phe
    50                  55                  60

Arg Asn Ala Phe Thr Ser Val Ser Ser Cys Ser Pro Ser Arg Ala Ser
65                  70                  75                  80

Leu Leu Thr Gly Leu Pro Gln His Gln Asn Gly Met Tyr Gly Leu His
                85                  90                  95

Gln Asp Val His His Phe Asn Ser Phe Asp Lys Val Arg Ser Leu Pro
            100                 105                 110

Leu Leu Leu Ser Gln Ala Gly Val Arg Thr Gly Ile Ile Gly Lys Lys
        115                 120                 125

His Val Gly Pro Glu Thr Val Tyr Pro Phe Asp Phe Ala Tyr Thr Glu
    130                 135                 140

Glu Asn Gly Ser Val Leu Gln Val Gly Arg Asn Ile Thr Arg Ile Lys
145                 150                 155                 160

Leu Leu Val Arg Lys Phe Leu Gln Thr Gln Asp Asp Arg Pro Phe Phe
                165                 170                 175

Leu Tyr Val Ala Phe His Asp Pro His Arg Cys Gly His Ser Gln Pro
            180                 185                 190

Gln Tyr Gly Thr Phe Cys Glu Lys Phe Gly Asn Gly Glu Ser Gly Met
        195                 200                 205

Gly Arg Ile Pro Asp Trp Thr Pro Gln Ala Tyr Asp Pro Leu Asp Val
    210                 215                 220

Leu Val Pro Tyr Phe Val Pro Asn Thr Pro Ala Ala Arg Ala Asp Leu
225                 230                 235                 240

Ala Ala Gln Tyr Thr Thr Val Gly Arg Met Asp Gln Gly Val Gly Leu
                245                 250                 255

Val Leu Gln Glu Leu Arg Asp Ala Gly Val Leu Asn Asp Thr Leu Val
            260                 265                 270

Ile Phe Thr Ser Asp Asn Gly Ile Pro Phe Pro Ser Gly Arg Thr Asn
        275                 280                 285

Leu Tyr Trp Pro Gly Thr Ala Glu Pro Leu Leu Val Ser Ser Pro Glu
    290                 295                 300

His Pro Lys Arg Trp Gly Gln Val Ser Glu Ala Tyr Val Ser Leu Leu
305                 310                 315                 320

Asp Leu Thr Pro Thr Ile Leu Asp Trp Phe Ser Ile Pro Tyr Pro Ser
                325                 330                 335

Tyr Ala Ile Phe Gly Ser Lys Thr Ile His Leu Thr Gly Arg Ser Leu
            340                 345                 350

Leu Pro Ala Leu Glu Ala Glu Pro Leu Trp Ala Thr Val Phe Gly Ser
        355                 360                 365

Gln Ser His His Glu Val Thr Met Ser Tyr Pro Met Arg Ser Val Gln
    370                 375                 380

His Arg His Phe Arg Leu Val His Asn Leu Asn Phe Lys Met Pro Phe
```

```
                385                 390                 395                 400
Pro Ile Asp Gln Asp Phe Tyr Val Ser Pro Thr Phe Gln Asp Leu Leu
                    405                 410                 415

Asn Arg Thr Thr Ala Gly Gln Pro Thr Gly Trp Tyr Lys Asp Leu Arg
                420                 425                 430

His Tyr Tyr Arg Ala Arg Trp Glu Leu Tyr Asp Arg Ser Arg Asp
            435                 440                 445

Pro His Glu Thr Gln Asn Leu Ala Thr Asp Pro Arg Phe Ala Gln Leu
        450                 455                 460

Leu Glu Met Leu Arg Asp Gln Leu Ala Lys Trp Gln Trp Glu Thr His
465                 470                 475                 480

Asp Pro Trp Val Cys Ala Pro Asp Gly Val Leu Glu Glu Lys Leu Ser
                485                 490                 495

Pro Gln Cys Gln Pro Leu His Asn Glu Leu Ser Ser Arg Ser Val Ile
            500                 505                 510

Asp Ala Leu Gln Tyr Lys Leu Glu Gly Thr Thr Arg Leu Thr Arg Lys
        515                 520                 525

Arg Gly Leu Lys Leu Ala Thr Ala Leu Ser Leu Ser Asn Lys Phe Val
    530                 535                 540

Glu Gly Ser Arg Ser
545

<210> SEQ ID NO 25
<211> LENGTH: 1656
<212> TYPE: DNA
<213> ORGANISM: Artificial Sequence
<220> FEATURE:
<223> OTHER INFORMATION: chimeric sequence
<220> FEATURE:
<221> NAME/KEY: CDS
<222> LOCATION: (1)..(1656)

<400> SEQUENCE: 25 atg ccc ccg ccc cgc acc ggc cgc ggc ctg ctg tgg ctg ggc ctg gtg      48
Met Pro Pro Pro Arg Thr Gly Arg Gly Leu Leu Trp Leu Gly Leu Val
1               5                   10                  15 ctg agc agc gtg tgc gtg gcc ctg ggc cgt ccc cgg aac gca ctg ctg      96
Leu Ser Ser Val Cys Val Ala Leu Gly Arg Pro Arg Asn Ala Leu Leu
            20                  25                  30 ctc ctc gcg gat gac gga ggc ttt gag agt ggc gcg tac aac aac agc     144
Leu Leu Ala Asp Asp Gly Gly Phe Glu Ser Gly Ala Tyr Asn Asn Ser
        35                  40                  45 gcc atc gcc acc ccg cac ctg gac gcc ttg gcc cgc cgc agc ctc ctc     192
Ala Ile Ala Thr Pro His Leu Asp Ala Leu Ala Arg Arg Ser Leu Leu
    50                  55                  60 ttt cgc aat gcc ttc acc tcg gtc agc agc tgc tct ccc agc cgc gcc     240
Phe Arg Asn Ala Phe Thr Ser Val Ser Ser Cys Ser Pro Ser Arg Ala
65                  70                  75                  80 agc ctc ctc act ggc ctg ccc cag cat cag aat ggg atg tac ggg ctg     288
Ser Leu Leu Thr Gly Leu Pro Gln His Gln Asn Gly Met Tyr Gly Leu
                85                  90                  95 cac cag gac gtg cac cac ttc aac tcc ttc gac aag gtg cgg agc ctg     336
His Gln Asp Val His His Phe Asn Ser Phe Asp Lys Val Arg Ser Leu
            100                 105                 110 ccg ctg ctg ctc agc caa gct ggt gtg cgc aca ggc atc atc ggg aag     384
Pro Leu Leu Leu Ser Gln Ala Gly Val Arg Thr Gly Ile Ile Gly Lys
        115                 120                 125 aag cac gtg ggg ccg gag acc gtg tac ccg ttt gac ttt gcg tac acg     432
Lys His Val Gly Pro Glu Thr Val Tyr Pro Phe Asp Phe Ala Tyr Thr
```

```
                130             135             140
gag gag aat ggc tcc gtc ctc cag gtg ggg cgg aac atc act aga att      480
Glu Glu Asn Gly Ser Val Leu Gln Val Gly Arg Asn Ile Thr Arg Ile
145                 150                 155                 160 aag ctg ctc gtc cgg aaa ttc ctg cag act cag gat gac cgg cct ttc      528
Lys Leu Leu Val Arg Lys Phe Leu Gln Thr Gln Asp Asp Arg Pro Phe
                165                 170                 175 ttc ctc tac gtc gcc ttc cac gac ccc cac cgc tgt ggg cac tcc caa      576
Phe Leu Tyr Val Ala Phe His Asp Pro His Arg Cys Gly His Ser Gln
            180                 185                 190 ccc cag tac gga acc ttc tgt gag aag ttt ggc aac gga gag agc ggc      624
Pro Gln Tyr Gly Thr Phe Cys Glu Lys Phe Gly Asn Gly Glu Ser Gly
        195                 200                 205 atg ggt cgt atc cca gac tgg acc ccc cag gcc tac gac cca ctg gac      672
Met Gly Arg Ile Pro Asp Trp Thr Pro Gln Ala Tyr Asp Pro Leu Asp
210                 215                 220 gtg ctg gtg cct tac ttc gtc ccc aac acc ccg gca gcc cga gcc gac      720
Val Leu Val Pro Tyr Phe Val Pro Asn Thr Pro Ala Ala Arg Ala Asp
225                 230                 235                 240 ctg gcc gct cag tac acc acc gtc ggc cgc atg gac caa gga gtt gga      768
Leu Ala Ala Gln Tyr Thr Thr Val Gly Arg Met Asp Gln Gly Val Gly
                245                 250                 255 ctg gtg ctc cag gag ctg cgt gac gcc ggt gtc ctg aac gac aca ctg      816
Leu Val Leu Gln Glu Leu Arg Asp Ala Gly Val Leu Asn Asp Thr Leu
            260                 265                 270 gtg atc ttc acg tcc gac aac ggg atc ccc ttc ccc agc ggc agg acc      864
Val Ile Phe Thr Ser Asp Asn Gly Ile Pro Phe Pro Ser Gly Arg Thr
        275                 280                 285 aac ctg tac tgg ccg ggc act gct gaa ccc tta ctg gtg tca tcc ccg      912
Asn Leu Tyr Trp Pro Gly Thr Ala Glu Pro Leu Leu Val Ser Ser Pro
290                 295                 300 gag cac cca aaa cgc tgg ggc caa gtc agc gag gcc tac gtg agc ctc      960
Glu His Pro Lys Arg Trp Gly Gln Val Ser Glu Ala Tyr Val Ser Leu
305                 310                 315                 320 cta gac ctc acg ccc acc atc ttg gat tgg ttc tcg atc ccg tac ccc     1008
Leu Asp Leu Thr Pro Thr Ile Leu Asp Trp Phe Ser Ile Pro Tyr Pro
                325                 330                 335 agc tac gcc atc ttt ggc tcg aag acc atc cac ctc act ggc cgg tcc     1056
Ser Tyr Ala Ile Phe Gly Ser Lys Thr Ile His Leu Thr Gly Arg Ser
            340                 345                 350 ctc ctg ccg gcg ctg gag gcc gag ccc ctc tgg gcc acc gtc ttt ggc     1104
Leu Leu Pro Ala Leu Glu Ala Glu Pro Leu Trp Ala Thr Val Phe Gly
        355                 360                 365 agc cag agc cac cac gag gtc acc atg tct tac ccc atg cgc tcc gtg     1152
Ser Gln Ser His His Glu Val Thr Met Ser Tyr Pro Met Arg Ser Val
370                 375                 380 cag cac cgg cac ttc cgc ctc gtg cac aac ctc aac ttc aag atg ccc     1200
Gln His Arg His Phe Arg Leu Val His Asn Leu Asn Phe Lys Met Pro
385                 390                 395                 400 ttt ccc atc gac cag gac ttc tac gtc tca ccc acc ttc cag gac ctc     1248
Phe Pro Ile Asp Gln Asp Phe Tyr Val Ser Pro Thr Phe Gln Asp Leu
                405                 410                 415 ctg aac cgc acc aca gct ggt cag ccc acg ggc tgg tac aag gac ctc     1296
Leu Asn Arg Thr Thr Ala Gly Gln Pro Thr Gly Trp Tyr Lys Asp Leu
            420                 425                 430 cgt cat tac tac tac cgg gcg cgc tgg gag ctc tac gac cgg agc cgg     1344
Arg His Tyr Tyr Tyr Arg Ala Arg Trp Glu Leu Tyr Asp Arg Ser Arg
        435                 440                 445 gac ccc cac gag acc cag aac ctg gcc acc gac ccg cgc ttt gct cag     1392
```

```
Asp Pro His Glu Thr Gln Asn Leu Ala Thr Asp Pro Arg Phe Ala Gln
    450                 455                 460 ctt ctg gag atg ctt cgg gac cag ctg gcc aag tgg cag tgg gag acc      1440
Leu Leu Glu Met Leu Arg Asp Gln Leu Ala Lys Trp Gln Trp Glu Thr
465                 470                 475                 480 cac gac ccc tgg gtg tgc gcc ccc gac ggc gtc ctg gag gag aag ctc      1488
His Asp Pro Trp Val Cys Ala Pro Asp Gly Val Leu Glu Glu Lys Leu
                485                 490                 495 tct ccc cag tgc cag ccc ctc cac aat gag ctg tca tct aga tct gtc      1536
Ser Pro Gln Cys Gln Pro Leu His Asn Glu Leu Ser Ser Arg Ser Val
            500                 505                 510 att gat gca ctg cag tac aaa tta gag ggc acc aca aga ttg aca aga      1584
Ile Asp Ala Leu Gln Tyr Lys Leu Glu Gly Thr Thr Arg Leu Thr Arg
        515                 520                 525 aaa agg gga ttg aag tta gcc aca gct ctg tct ctg agc aac aaa ttt      1632
Lys Arg Gly Leu Lys Leu Ala Thr Ala Leu Ser Leu Ser Asn Lys Phe
530                 535                 540 gtg gag ggt agt aga tct tag tga                                      1656
Val Glu Gly Ser Arg Ser
545                 550

<210> SEQ ID NO 26
<211> LENGTH: 550
<212> TYPE: PRT
<213> ORGANISM: Artificial Sequence
<220> FEATURE:
<223> OTHER INFORMATION: Synthetic Construct

<400> SEQUENCE: 26

Met Pro Pro Pro Arg Thr Gly Arg Gly Leu Leu Trp Leu Gly Leu Val
1               5                   10                  15

Leu Ser Ser Val Cys Val Ala Leu Gly Arg Pro Arg Asn Ala Leu Leu
                20                  25                  30

Leu Leu Ala Asp Asp Gly Gly Phe Glu Ser Gly Ala Tyr Asn Asn Ser
            35                  40                  45

Ala Ile Ala Thr Pro His Leu Asp Ala Leu Ala Arg Arg Ser Leu Leu
        50                  55                  60

Phe Arg Asn Ala Phe Thr Ser Val Ser Ser Cys Ser Pro Ser Arg Ala
65                  70                  75                  80

Ser Leu Leu Thr Gly Leu Pro Gln His Gln Asn Gly Met Tyr Gly Leu
                85                  90                  95

His Gln Asp Val His His Phe Asn Ser Phe Asp Lys Val Arg Ser Leu
            100                 105                 110

Pro Leu Leu Leu Ser Gln Ala Gly Val Arg Thr Gly Ile Ile Gly Lys
        115                 120                 125

Lys His Val Gly Pro Glu Thr Val Tyr Pro Phe Asp Phe Ala Tyr Thr
130                 135                 140

Glu Glu Asn Gly Ser Val Leu Gln Val Gly Arg Asn Ile Thr Arg Ile
145                 150                 155                 160

Lys Leu Leu Val Arg Lys Phe Leu Gln Thr Gln Asp Asp Arg Pro Phe
                165                 170                 175

Phe Leu Tyr Val Ala Phe His Asp Pro His Arg Cys Gly His Ser Gln
            180                 185                 190

Pro Gln Tyr Gly Thr Phe Cys Glu Lys Phe Gly Asn Gly Glu Ser Gly
        195                 200                 205

Met Gly Arg Ile Pro Asp Trp Thr Pro Gln Ala Tyr Asp Pro Leu Asp
210                 215                 220
```

```
Val Leu Val Pro Tyr Phe Val Pro Asn Thr Pro Ala Ala Arg Ala Asp
225                 230                 235                 240

Leu Ala Ala Gln Tyr Thr Thr Val Gly Arg Met Asp Gln Gly Val Gly
            245                 250                 255

Leu Val Leu Gln Glu Leu Arg Asp Ala Gly Val Leu Asn Asp Thr Leu
        260                 265                 270

Val Ile Phe Thr Ser Asp Asn Gly Ile Pro Phe Pro Ser Gly Arg Thr
    275                 280                 285

Asn Leu Tyr Trp Pro Gly Thr Ala Glu Pro Leu Leu Val Ser Ser Pro
290                 295                 300

Glu His Pro Lys Arg Trp Gly Gln Val Ser Glu Ala Tyr Val Ser Leu
305                 310                 315                 320

Leu Asp Leu Thr Pro Thr Ile Leu Asp Trp Phe Ser Ile Pro Tyr Pro
                325                 330                 335

Ser Tyr Ala Ile Phe Gly Ser Lys Thr Ile His Leu Thr Gly Arg Ser
            340                 345                 350

Leu Leu Pro Ala Leu Glu Ala Glu Pro Leu Trp Ala Thr Val Phe Gly
        355                 360                 365

Ser Gln Ser His His Glu Val Thr Met Ser Tyr Pro Met Arg Ser Val
370                 375                 380

Gln His Arg His Phe Arg Leu Val His Asn Leu Asn Phe Lys Met Pro
385                 390                 395                 400

Phe Pro Ile Asp Gln Asp Phe Tyr Val Ser Pro Thr Phe Gln Asp Leu
                405                 410                 415

Leu Asn Arg Thr Thr Ala Gly Gln Pro Thr Gly Trp Tyr Lys Asp Leu
            420                 425                 430

Arg His Tyr Tyr Tyr Arg Ala Arg Trp Glu Leu Tyr Asp Arg Ser Arg
        435                 440                 445

Asp Pro His Glu Thr Gln Asn Leu Ala Thr Asp Pro Arg Phe Ala Gln
450                 455                 460

Leu Leu Glu Met Leu Arg Asp Gln Leu Ala Lys Trp Gln Trp Glu Thr
465                 470                 475                 480

His Asp Pro Trp Val Cys Ala Pro Asp Gly Val Leu Glu Glu Lys Leu
                485                 490                 495

Ser Pro Gln Cys Gln Pro Leu His Asn Glu Leu Ser Ser Arg Ser Val
            500                 505                 510

Ile Asp Ala Leu Gln Tyr Lys Leu Glu Gly Thr Thr Arg Leu Thr Arg
        515                 520                 525

Lys Arg Gly Leu Lys Leu Ala Thr Ala Leu Ser Leu Ser Asn Lys Phe
530                 535                 540

Val Glu Gly Ser Arg Ser
545                 550

<210> SEQ ID NO 27
<211> LENGTH: 709
<212> TYPE: DNA
<213> ORGANISM: Homo sapiens
<220> FEATURE:
<221> NAME/KEY: promoter
<222> LOCATION: (1)..(709)

<400> SEQUENCE: 27
gctagcaggt taattttaa aaagcagtca aaagtccaag tggcccttgg cagcatttac    60
tctctctgtt tgctctggtt aataatctca ggagcacaaa cattccagat ccaggttaat   120
ttttaaaaag cagtcaaaag tccaagtggc ccttggcagc atttactctc tctgtttgct   180
```

```
ctggttaata atctcaggag cacaaacatt ccagatccgg cgcgccaggg ctggaagcta      240
cctttgacat catttcctct gcgaatgcat gtataatttc tacagaacct attagaaagg      300
atcacccagc tctgctttt gtacaacttt cccttaaaaa actgccaatt ccactgctgt       360
ttggcccaat agtgagaact ttttcctgct gcctcttggt gcttttgcct atggcccta       420 ttctgcctgc tgaagacact cttgccagca tggacttaaa cccctccagc tctgacaatc      480
ctctttctct tttgttttac atgaagggtc tggcagccaa agcaatcact caaagttcaa      540
accttatcat ttttgcttt gttcctcttg gccttggttt tgtacatcag ctttgaaaat       600
accatcccag ggttaatgct ggggttaatt tataactaag agtgctctag ttttgcaata      660
caggacatgc tataaaaatg gaaagatgtt gctttctgag agactgcag                  709
```

```
<210> SEQ ID NO 28
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(26)

<400> SEQUENCE: 28
cgtccccgga acgcactgct gctcct                                            26

<210> SEQ ID NO 29
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(36)

<400> SEQUENCE: 29
gcggcctcta gatgacagct cattgtggag gggctg                                 36

<210> SEQ ID NO 30
<211> LENGTH: 78
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(78)

<400> SEQUENCE: 30
ggccgcatgc cgtcttctgt ctcgtggggc atcctcctgc tggcaggcct gtgctgcctg      60
gtccctgtct ccctggct                                                     78

<210> SEQ ID NO 31
<211> LENGTH: 74
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(74)

<400> SEQUENCE: 31
```

```
agccagggag acagggacca ggcagcacag gcctgccagc aggaggatgc cccacgagac    60
agaagacggc atgc                                                      74

<210> SEQ ID NO 32
<211> LENGTH: 81
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(81)

<400> SEQUENCE: 32
ggccgcatgc ccccgccccg caccggccgc ggcctgctgt ggctgggcct ggtgctgagc    60
agcgtgtgcg tggccctggg c                                              81

<210> SEQ ID NO 33
<211> LENGTH: 77
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(77)

<400> SEQUENCE: 33
gcccagggcc acgcacacgc tgctcagcac caggcccagc cacagcaggc cgcggccggt    60
gcggggcggg ggcatgc                                                   77

<210> SEQ ID NO 34
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(27)

<400> SEQUENCE: 34
agatctctgt cattgatgca ctgcagt                                        27

<210> SEQ ID NO 35
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(29)

<400> SEQUENCE: 35
agatctacta ccctccacaa atttgttgc                                      29
```

THERAPEUTIC STRATEGIES TO TREAT CNS PATHOLOGY IN MUCOPOLYSACCHARIDOSES

CROSS-REFERENCE TO RELATED APPLICATION

This application is a 371 of PCT/IB2010/056024, filed Dec. 22, 2010, the contents of which are incorporated herein by reference.

FIELD OF THE INVENTION

The invention relates to a therapeutic approach, either viral vector-mediated gene therapy or by administration of modified sulfatases, in particular the sulfamidase enzyme, to cross the blood-brain barrier and treat the CNS pathology in Mucopolysaccharidoses (MPS), in particular MPS type IIIA.

BACKGROUND OF THE INVENTION

Mucopolysaccharidosis type IIIA (MPS-IIIA) is an inherited disease caused by the deficiency of sulfamidase (SGSH), an enzyme involved in the stepwise degradation of large macromolecules called heparan sulfates. As a consequence, undegraded substrates accumulate in the cells and tissues of the affected patients causing cell damage. The central nervous system (CNS) is the predominant target of damage and in fact, MPS-IIIA patients show severe mental retardation and neuropathological decline that ultimately leads to death (often<20 years). Clinical symptoms include hyperactivity, aggressive behaviour and sleep disturbance (1).

A naturally occurring mouse model of MPS-IIIA has been identified with pathophysiology and symptoms that resemble the human condition (2-4). These mice represent an ideal model to study the physiopathology of this disorder and to test new therapeutic protocols.

The treatment of brain lesions represents the principal goal of any therapeutic approach for MPS-IIIA. A route to reach the brain consists in the direct injection of a therapeutic molecule directly into the brain. A number of different enzyme replacement therapy (ERT) protocols have been tested. In these protocols, a recombinant sulfamidase enzyme was administered through the direct injection into the brain of MPSIIIA mice. These strategies are able to delay the appearance of neurodegenerative changes when sulfamidase is administered in the younger mice (5, 6). In addiction, a Gene Therapy protocol based on the intracerebral injection of the SGSH gene via AAV vectors was successfully developed by the authors of the invention (7). Although these direct brain-targeting approaches have been shown to be clinically effective they represent highly invasive approaches for human therapeutic applicability.

Since every neuron in the brain is perfused by its own blood vessel, an effective alternative low-invasive route to reach the brain is the intravenous administration of the therapeutic molecule (8). However, this very dense network of microvasculature, which forms the Blood-Brain Barrier (BBB), is not permeable to all the molecules and might impede effective delivery of therapeutic agents (9). Indeed, intravenous administration of lysosomal enzymes has produced a therapeutic effect on the somatic pathology of many LSDs but it has no or little effect on the CNS pathology due to the impermeability of the BBB to large molecules (10). In MPS-IIIA, it has been demonstrated that intravenous injection of sulfamidase does not alter the pathology or behavioural process occurring in the MPS-IIIA mouse brain when the enzyme is supplied after the BBB has been formed (11).

Importantly, a recent study by Urayama et al. demonstrated that sulfamidase is transported across the BBB in neonatal mice throughout the mannose 6-phosphate receptor-mediated transport but the influx into adult brain was negligible (12).

It is clear that in such context the real challenge for the therapy of MPS-IIIA and in general for all LSDs involving the CNS is to develop CNS systemic treatment strategies that can overcome the major obstacle represented by BBB. An effective strategy to cross the BBB is the targeting of proteins to the CNS via receptor-mediated transcytosis (13). Well-characterized BBB receptors include: low density lipoprotein receptor (LDLR), the transferrin receptor (TfR), and the insulin-like growth factor receptor (IGF-R). The LDLR family represents a group of cell surface receptors that binds apolipoprotein (Apo) complexes (lipid carriers) for the internalizing into the lysosomes (14-16). On the surface of the BBB, LDLR binding to Apo results in the transcytosis to the luminal side of the BBB, where the apolipoprotein is released to be uptaken by neurons and astrocytes. A recent study has demonstrated that fusing the LDLR-binding domain of Apo to a lysosome enzyme results in an efficient delivery of the chimeric enzyme to the CNS (17).

WO2004108071 refers to a chimeric CNS targeting polypeptide comprising a BBB-receptor binding domain, such as the Apolipoprotein B binding domain, for therapeutic use in lysosomal storage diseases.

WO2004064750 refers to nucleic acids encoding a chimeric lysosomal polypeptide (specifically the lysosomal acid glucosidase GAA implicated in the lysosomal storage disorder Glycogen storage disease type II) comprising a secretory signal sequence (i.e. Vi-antitrypsin and alpha-1-antitrypsin) and the related AAV vectors.

WO2005002515 refers to a compound comprising a megalin-binding moiety conjugated to an agent of interest for receptor mediated drug delivery, particularly by transcytosis, across the blood-brain barrier. Moreover the document refers to a method of treating a lysosomal storage disease based on the administration of a composition comprising a megalin-binding moiety. Apolipoprotein B and Mucopolysaccharidosis IIIA are mentioned.

WO2009131698 refers to a therapy based on a chimeric NaGlu enzyme characterized by an Apolipoprotein B binding domain and directed specifically to Mucopolysaccharidosis IIIB.

Cardone et al. (Hum Mol Gen, 2006 15(7):1225) describes the correction of Hunter syndrome (the lysosomal storage disease Mucopolysaccharidosis Type II) in the MPSII mouse model by liver-directed AAV2/8-TBG-mediated gene delivery.

WO2007092563 refers to a method and compositions for tolerizing a mammal's brain to exogenously administered acid sphingomyelinase polypeptide by first delivering an effective amount of a transgene encoding the polypeptide to the mammal's hepatic tissue and then administering an effective amount of the transgene to the mammal's central nervous system (CNS). The therapeutic approach is directed to Niemann-Pick disease, a lysosomal storage disease. Liver-specific promoters and AAV type 8 are mentioned.

WO2009075815 refers to methods of treating Pompe disease (a lysosomal storage disease) which involves the administration of an AAV vector in the context of enzyme replacement therapy. Liver-specific promoter (thyroid hormone-binding globulin promoter) and AAV type 8 are mentioned.

None of the above prior art cited documents disclose or even suggest the modified sufamidase enzyme of the instant invention and that it may have a therapeutic effect for the treatment of MPS type IIIA.

SUMMARY OF THE INVENTION

As disclosed in the background art, brain pathology is the most common feature in lysosomal storage disorders. Therefore, the treatment of brain lesions represents the principal goal of any effective therapy for these disorders.

The major obstacle to efficiently treat the brain by systemic delivery of a therapeutic agent is the blood brain barrier (BBB).

Authors developed a new non-invasive therapeutic approach to treat the brain pathology in the mucopolysaccharidosis type IIIA (MPS-IIIA), a lysosomal storage disorder with a severe central nervous system involvement. This strategy is based on the construction of a chimeric sulfamidase (the sulfatase enzyme which is deficient in MPS-IIIA), optimized with two amino-acid sequences (one to the N-terminus and the other to the C-terminus of the protein) which confer to the modified sulfamidase the capability to be highly secreted and efficiently targeted to the brain by crossing the blood brain barrier (BBB). The modified enzyme is expressed by adeno-associated virus (AAV) serotype 8 which specifically target the liver and make it like a factory organ of the therapeutic enzyme.

The modified sulfamidase may be effectively used for both gene therapy and for enzyme replacement therapy (ERT).

The modification approach may be used for other lysosomal enzymes which are deficient in other mucopolisaccharidoses with severe CNS involvement.

Therefore it is an object of the instant invention a nucleotide sequence encoding for a chimeric sulfatase, said chimeric sulfatase essentially consisting in the N-terminal-C-terminal sequence order of: a) a signal peptide derived by either the human α-antitrypsin (hAAT) amino acid sequence or the human Iduronate-2-sulfatase (IDS) amino acid sequence; b) a human sulfatase derived amino acid sequence deprived of its signal peptide; c) the ApoB LDLR-binding domain.

In a preferred embodiment the encoded signal peptide has a sequence belonging to the following group: MPSS-VSWGILLLAGLCCLVPVSLA (SEQ ID No. 2) or MPP-PRTGRGLLWLGLVLSSVCVALG (SEQ ID No. 4 or 6).

In a preferred embodiment the nucleotide the human sulfatase is the human sulfamidase, more preferably the encoded human sulfamidase derived amino acid sequence has essentially the sequence:

```
                                            (SEQ ID No. 8)
MSCPVPACCALLLVLGLCRARPRNALLLLADDGGFESGAYNNSAIATPHL

DALARRSLLFRNAFTSVSSCSPSRASLLTGLPQHQNGMYGLHQDVHHFNS

FDKVRSLPLLLSQAGVRTGIIGKKHVGPETVYPFDFAYTEENGSVLQVGR

NITRIKLLVRKFLQTQDDRPFFLYVAFHDPHRCGHSQPQYGTFCEKFGNG

ESGMGRIPDWTPQAYDPLDVLVPYFVPNTPAARADLAAQYTTVGRMDQGV

GLVLQELRDAGVLNDTLVIFTSDNGIPFPSGRTNLYWPGTAEPLLVSSPE

HPKRWGQVSEAYVSLLDLTPTILDWFSIPYPSYAIFGSKTIHLTGRSLLP

ALEAEPLWATVFGSQSHHEVTMSYPMRSVQHRHFRLVHNLNFKMPFPIDQ
```

-continued
```
DFYVSPTFQDLLNRTTAGQPTGWYKDLRHYYYRARWELYDRSRDPHETQN

LATDPRFAQLLEMLRDQLAKWQWETHDPWVCAPDGVLEEKLSPQCQPLHN

EL.
```

Such sequence is encoded by SEQ ID No. 7 nt sequence:

```
5'-
ATGAGCTGCCCCGTGCCCGCCTGCTGCGCGCTGCTGCTAGTCCTGGGGCT

CTGCCGGGCGCGTCCCCGGAACGCACTGCTGCTCCTCGCGGATGACGGAG

GCTTTGAGAGTGGCGCGTACAACAACAGCGCCATCGCCACCCCGCACCTG

GACGCCTTGGCCCGCCGCAGCCTCCTCTTTCGCAATGCCTTCACCTCGGT

CAGCAGCTGCTCTCCCAGCCGCGCCAGCCTCCTCACTGGCCTGCCCCAGC

ATCAGAATGGGATGTACGGGCTGCACCAGGACGTGCACCACTTCAACTCC

TTCGACAAGGTGCGGAGCCTGCCGCTGCTGCTCAGCCAAGCTGGTGTGCG

CACAGGCATCATCGGGAAGAAGCACGTGGGGCCGGAGACCGTGTACCCGT

TTGACTTTGCGTACACGGAGGAGAATGGCTCCGTCCTCCAGGTGGGGCGG

AACATCACTAGAATTAAGCTGCTCGTCCGGAAATTCCTGCAGACTCAGGA

TGACCGGCCTTTCTTCCTCTACGTCGCCTTCCACGACCCCCACCGCTGTG

GGCACTCCCAGCCCCAGTACGGAACCTTCTGTGAGAAGTTTGGCAACGGA

GAGAGCGGCATGGGTCGTATCCCAGACTGGACCCCCCAGGCCTACGACCC

ACTGGACGTGCTGGTGCCTTACTTCGTCCCCAACACCCCGGCAGCCCGAG

CCGACCTGGCCGCTCAGTACACCACCGTCGGCCGCATGGACCAAGGAGTT

GGACTGGTGCTCCAGGAGCTGCGTGACGCCGGTGTCCTGAACGACACACT

GGTGATCTTCACGTCCGACAACGGGATCCCCTTCCCCAGCGGCAGGACCA

ACCTGTACTGGCCGGGCACTGCTGAACCCTTACTGGTGTCATCCCCGGAG

CACCCAAAACGCTGGGGCCAAGTCAGCGAGGCCTACGTGAGCCTCCTAGA

CCTCACGCCCACCATCTTGGATTGGTTCTCGATCCCGTACCCCAGCTACG

CCATCTTTGGCTCGAAGACCATCCACCTCACTGGCCGGTCCCTCCTGCCG

GCGCTGGAGGCCGAGCCCCTCTGGGCCACCGTCTTTGGCAGCCAGAGCCA

CCACGAGGTCACCATGTCCTACCCCATGCGCTCCGTGCAGCACCGGCACT

TCCGCCTCGTGCACAACCTCAACTTCAAGATGCCCTTTCCCATCGACCAG

GACTTCTACGTCTCACCCACCTTCCAGGACCTCCTGAACCGCACCACAGC

TGGTCAGCCCACGGGCTGGTACAAGGACCTCCGTCATTACTACTACCGGG

CGCGCTGGGAGCTCTACGACCGGAGCCGGGACCCCCACGAGACCCAGAAC

CTGGCCACCGACCCGCGCTTTGCTCAGCTTCTGGAGATGCTTCGGGACCA

GCTGGCCAAGTGGCAGTGGGAGACCCACGACCCCTGGGTGTGCGCCCCCG

ACGGCGTCCTGGAGGAGAAGCTCTCTCCCCAGTGCCAGCCCCTCCACAAT

GAGCTGTGA-3'.
```

In a preferred embodiment the encoded ApoB LDLR-binding domain has essentially the sequence:

```
                                        (SEQ ID No. 10)
SVIDALQYKLEGTTRLTRKRGLKLATALSLSNKFVEGS.
```

In a preferred embodiment the nucleotide sequence has essentially the sequence belonging to the following group:

```
SEQUENCES WITH FLAG (expert shall easily substi-
tute the flag sequence with any other suitable
spacer sequence):
a) Assembly hAATsp-SGSH-3xflag cassette (1611).
                                      (SEQ ID No. 11)
5'-
ATGCCGTCTTCTGTCTCGTGGGGCATCCTCCTGCTGGCAGGCCTGTGCTG

CCTGGTCCCTGTCTCCCTGGCTCGTCCCCGGAACGCACTGCTGCTCCTCG

CGGATGACGGAGGCTTTGAGAGTGGCGCGTACAACAACAGCGCCATCGCC

ACCCCGCACCTGGACGCCTTGGCCCGCCGCAGCCTCCTCTTTCGCAATGC

CTTCACCTCGGTCAGCAGCTGCTCTCCCAGCCGCGCCAGCCTCCTCACTG

GCCTGCCCCAGCATCAGAATGGGATGTACGGGCTGCACCAGGACGTGCAC

CACTTCAACTCCTTCGACAAGGTGCGGAGCCTGCCGCTGCTGCTCAGCCA

AGCTGGTGTGCGCACAGGCATCATCGGGAAGAAGCACGTGGGGCCGGAGA

CCGTGTACCCGTTTGACTTTGCGTACACGGAGGAGAATGGCTCCGTCCTC

CAGGTGGGGCGGAACATCACTAGAATTAAGCTGCTCGTCCGGAAATTCCT

GCAGACTCAGGATGACCGGCCTTTCTTCCTCTACGTCGCCTTCCACGACC

CCACCGCTGTGGGCACTCCCAACCCCAGTACGGAACCTTCTGTGAGAAG

TTTGGCAACGGAGAGAGCGGCATGGGTCGTATCCCAGACTGGACCCCCCA

GGCCTACGACCCACTGGACGTGCTGGTGCCTTACTTCGTCCCCAACACCC

CGGCAGCCCGAGCCGACCTGGCCGCTCAGTACACCACCGTCGGCCGCATG

GACCAAGGAGTTGGACTGGTGCTCCAGGAGCTGCGTGACGCCGGTGTCCT

GAACGACACACTGGTGATCTTCACGTCCGACAACGGGATCCCCTTCCCCA

GCGGCAGGACCAACCTGTACTGGCCGGGCACTGCTGAACCCTTACTGGTG

TCATCCCCGGAGCACCCAAAACGCTGGGGCCAAGTCAGCGAGGCCTACGT

GAGCCTCCTAGACCTCACGCCCACCATCTTGGATTGGTTCTCGATCCCGT

ACCCCAGCTACGCCATCTTTGGCTCGAAGACCATCCACCTCACTGGCCGG

TCCCTCCTGCCGGCGCTGGAGGCCGAGCCCCTCTGGGCCACCGTCTTTGG

CAGCCAGAGCCACCACGAGGTCACCATGTCCTACCCCATGCGCTCCGTGC

AGCACCGGCACTTCCGCCTCGTGCACAACCTCAACTTCAAGATGCCCTTT

CCCATCGACCAGGACTTCTACGTCTCACCCACCTTCCAGGACCTCCTGAA

CCGCACCACAGCTGGTCAGCCCACGGGCTGGTACAAGGACCTCCGTCATT

ACTACTACCGGGCGCGCTGGGAGCTCTACGACCGGAGCCGGGACCCCCAC

GAGACCCAGAACCTGGCCACCGACCCGCGCTTTGCTCAGCTTCTGGAGAT

GCTTCGGGACCAGCTGGCCAAGTGGCAGTGGGAGACCCACGACCCCTGGG

TGTGCGCCCCCGACGGCGTCCTGGAGGAGAAGCTCTCTCCCCAGTGCCAG

CCCCTCCACAATGAGCTGTCATCTAGAGGATCCCGGGCTGACTACAAAGA

CCATGACGGTGATTATAAAGATCATGACATCGACTACAAGGATGACGATG

ACAAGTAGTGA-3'
```

```
b) Assembly hIDSsp-SGSH-3xflag cassette (1614 bp).
                                      (SEQ ID No. 13)
5'-
ATGCCCCCGCCCCGCACCGGCCGCGGCCTGCTGTGGCTGGGCCTGGTGCT

GAGCAGCGTGTGCGTGGCCCTGGGCCGTCCCCGGAACGCACTGCTGCTCC

TCGCGGATGACGGAGGCTTTGAGAGTGGCGCGTACAACAACAGCGCCATC

GCCACCCCGCACCTGGACGCCTTGGCCCGCCGCAGCCTCCTCTTTCGCAA

TGCCTTCACCTCGGTCAGCAGCTGCTCTCCCAGCCGCGCCAGCCTCCTCA

CTGGCCTGCCCCAGCATCAGAATGGGATGTACGGGCTGCACCAGGACGTG

CACCACTTCAACTCCTTCGACAAGGTGCGGAGCCTGCCGCTGCTGCTCAG

CCAAGCTGGTGTGCGCACAGGCATCATCGGGAAGAAGCACGTGGGGCCGG

AGACCGTGTACCCGTTTGACTTTGCGTACACGGAGGAGAATGGCTCCGTC

CTCCAGGTGGGGCGGAACATCACTAGAATTAAGCTGCTCGTCCGGAAATT

CCTGCAGACTCAGGATGACCGGCCTTTCTTCCTCTACGTCGCCTTCCACG

ACCCCCACCGCTGTGGGCACTCCCAACCCCAGTACGGAACCTTCTGTGAG

AAGTTTGGCAACGGAGAGAGCGGCATGGGTCGTATCCCAGACTGGACCCC

CCAGGCCTACGACCCACTGGACGTGCTGGTGCCTTACTTCGTCCCCAACA

CCCCCGGCAGCCCGAGCCGACCTGGCCGCTCAGTACACCACCGTCGGCCGC

ATGGACCAAGGAGTTGGACTGGTGCTCCAGGAGCTGCGTGACGCCGGTGT

CCTGAACGACACACTGGTGATCTTCACGTCCGACAACGGGATCCCCTTCC

CCAGCGGCAGGACCAACCTGTACTGGCCGGGCACTGCTGAACCCTTACTG

GTGTCATCCCCGGAGCACCCAAAACGCTGGGGCCAAGTCAGCGAGGCCTA

CGTGAGCCTCCTAGACCTCACGCCCACCATCTTGGATTGGTTCTCGATCC

CGTACCCCAGCTACGCCATCTTTGGCTCGAAGACCATCCACCTCACTGGC

CGGTCCCTCCTGCCGGCGCTGGAGGCCGAGCCCCTCTGGGCCACCGTCTT

TGGCAGCCAGAGCCACCACGAGGTCACCATGTCCTACCCCATGCGCTCCG

TGCAGCACCGGCACTTCCGCCTCGTGCACAACCTCAACTTCAAGATGCCC

TTTCCCATCGACCAGGACTTCTACGTCTCACCCACCTTCCAGGACCTCCT

GAACCGCACCACAGCTGGTCAGCCCACGGGCTGGTACAAGGACCTCCGTC

ATTACTACTACCGGGCGCGCTGGGAGCTCTACGACCGGAGCCGGGACCCC

CACGAGACCCAGAACCTGGCCACCGACCCGCGCTTTGCTCAGCTTCTGGA

GATGCTTCGGGACCAGCTGGCCAAGTGGCAGTGGGAGACCCACGACCCCT

GGGTGTGCGCCCCCGACGGCGTCCTGGAGGAGAAGCTCTCTCCCCAGTGC

CAGCCCCTACACAATGAGCTCTCATCTAGAGGATCCCGGGCTGACTACAA

AGACCATGACGGTGATTATAAAGATCATGACATCGACTACAAGGATGACG

ATGACAAGTAGTGA-3' c) Assembly hAATsp-SGSH-3xflag-ApoB cassette (1734
bp).
                                      (SEQ ID No. 15)
5'-
ATGCCGTCTTCTGTCTCGTGGGGCATCCTCCTGCTGGCAGGCCTGTGCTG

CCTGGTCCCTGTCTCCCTGGCTCGTCCCCGGAACGCACTGCTGCTCCTCG

CGGATGACGGAGGCTTTGAGAGTGGCGCGTACAACAACAGCGCCATCGCC
```

-continued

```
ACCCCGCACCTGGACGCCTTGGCCCGCCGCAGCCTCCTCTTTCGCAATGC

CTTCACCTCGGTCAGCAGCTGCTCTCCCAGCCGCGCCAGCCTCCTCACTG

GCCTGCCCCAGCATCAGAATGGGATGTACGGGCTGCACCAGGACGTGCAC

CACTTCAACTCCTTCGACAAGGTGCGGAGCCTGCCGCTGCTGCTCAGCCA

AGCTGGTGTGCGCACAGGCATCATCGGGAAGAAGCACGTGGGGCCGGAGA

CCGTGTACCCGTTTGACTTTGCGTACACGGAGGAGAATGGCTCCGTCCTC

CAGGTGGGGCGGAACATCACTAGAATTAAGCTGCTCGTCCGGAAATTCCT

GCAGACTCAGGATGACCGGCCTTTCTTCCTCTACGTCGCCTTCCACGACC

CCACCGCTGTGGGCACTCCCAACCCCAGTACGGAACCTTCTGTGAGAAG

TTTGGCAACGGAGAGAGCGGCATGGGTCGTATCCCAGACTGGACCCCCCA

GGCCTACGACCCACTGGACGTGCTGGTGCCTTACTTCGTCCCCAACACCC

CGGCAGCCCGAGCCGACCTGGCCGCTCAGTACACCACCGTCGGCCGCATG

GACCAAGGAGTTGGACTGGTGCTCCAGGAGCTGCGTGACGCCGGTGTCCT

GAACGACACACTGGTGATCTTCACGTCCGACAACGGGATCCCCTTCCCA

GCGGCAGGACCAACCTGTACTGGCCGGGCACTGCTGAACCCTTACTGGTG

TCATCCCCGGAGCACCCAAAACGCTGGGGCCAAGTCAGCGAGGCCTACGT

GAGCCTCCTAGACCTCACGCCCACCATCTTGGATTGGTTCTCGATCCCGT

ACCCCAGCTACGCCATCTTTGGCTCGAAGACCATCCACCTCACTGGCCGG

TCCCTCCTGCCGGCGCTGGAGGCCGAGCCCCTCTGGGCCACCGTCTTTGG

CAGCCAGAGCCACCACGAGGTCACCATGTCTTACCCCATGCGCTCCGTGC

AGCACCGGCACTTCCGCCTCGTGCACAACCTCAACTTCAAGATGCCCTTT

CCCATCGACCAGGACTTCTACGTCTCACCCACCTTCCAGGACCTCCTGAA

CCGCACCACAGCTGGTCAGCCCACGGGCTGGTACAAGGACCTCCGTCATT

ACTACTACCGGGCGCGCTGGGAGCTCTACGACCGGAGCCGGGACCCCCAC

GAGACCCAGAACCTGGCCACCGACCCGCGCTTTGCTCAGCTTCTGGAGAT

GCTTCGGGACCAGCTGGCCAAGTGGCAGTGGGAGACCCACGACCCCTGGG

TGTGCGCCCCCGACGGCGTCCTGGAGGAGAAGCTCTCTCCCCAGTGCCAG

CCCCTCCACAATGAGCTGTCATCTAGAGGATCCCGGGCTGACTACAAAGA

CCATGACGGTGATTATAAAGATCATGACATCGACTACAAGGATGACGATG

ACAAGATCTCTGTCATTGATGCACTGCAGTACAAATTAGAGGGCACCACA

AGATTGACAAGAAAAAGGGGATTGAAGTTAGCCACAGCTCTGTCTCTGAG

CAACAAATTTGTGGAGGGTAGTAGATCTTAGTGA-3'
``` d) Assembly hIDSsp-SGSH-3xflag-ApoB cassette (1737 bp).

(SEQ ID No. 17)

```
5'-

ATGCCCCCGCCCCGCACCGGCCGCGGCCTGCTGTGGCTGGGCCTGGTGCT

GAGCAGCGTGTGCGTGGCCCTGGGCCGTCCCCGGAACGCACTGCTGCTCC

TCGCGGATGACGGAGGCTTTGAGAGTGGCGCGTACAACAACAGCGCCATC

GCCACCCCGCACCTGGACGCCTTGGCCCGCCGCAGCCTCCTCTTTCGCAA

TGCCTTCACCTCGGTCAGCAGCTGCTCTCCCAGCCGCGCCAGCCTCCTCA

CTGGCCTGCCCCAGCATCAGAATGGGATGTACGGGCTGCACCAGGACGTG
```

-continued

```
CACCACTTCAACTCCTTCGACAAGGTGCGGAGCCTGCCGCTGCTGCTCAG

CCAAGCTGGTGTGCGCACAGGCATCATCGGGAAGAAGCACGTGGGGCCGG

AGACCGTGTACCCGTTTGACTTTGCGTACACGGAGGAGAATGGCTCCGTC

CTCCAGGTGGGGCGGAACATCACTAGAATTAAGCTGCTCGTCCGGAAATT

CCTGCAGACTCAGGATGACCGGCCTTTCTTCCTCTACGTCGCCTTCCACG

ACCCCCACCGCTGTGGGCACTCCCAACCCCAGTACGGAACCTTCTGTGAG

AAGTTTGGCAACGGAGAGAGCGGCATGGGTCGTATCCCAGACTGGACCCC

CCAGGCCTACGACCCACTGGACGTGCTGGTGCCTTACTTCGTCCCCAACA

CCCCCGGCAGCCCGAGCCGACCTGGCCGCTCAGTACACCACCGTCGGCCGC

ATGGACCAAGGAGTTGGACTGGTGCTCCAGGAGCTGCGTGACGCCGGTGT

CCTGAACGACACACTGGTGATCTTCACGTCCGACAACGGGATCCCCTTCC

CCAGCGGCAGGACCAACCTGTACTGGCCGGGCACTGCTGAACCCTTACTG

GTGTCATCCCCGGAGCACCCAAAACGCTGGGGCCAAGTCAGCGAGGCCTA

CGTGAGCCTCCTAGACCTCACGCCCACCATCTTGGATTGGTTCTCGATCC

CGTACCCCAGCTACGCCATCTTTGGCTCGAAGACCATCCACCTCACTGGC

CGGTCCCTCCTGCCGGCGCTGGAGGCCGAGCCCCTCTGGGCCACCGTCTT

TGGCAGCCAGAGCCACCACGAGGTCACCATGTCCTACCCCATGCGCTCCG

TGCAGCACCGGCACTTCCGCCTCGTGCACAACCTCAACTTCAAGATGCCC

TTTCCCATCGACCAGGACTTCTACGTCTCACCCACCTTCCAGGACCTCCT

GAACCGCACCACAGCTGGTCAGCCCACGGGCTGGTACAAGGACCTCCGTC

ATTACTACTACCGGGCGCGCTGGGAGCTCTACGACCGGAGCCGGGACCCC

CACGAGACCCAGAACCTGGCCACCGACCCGCGCTTTGCTCAGCTTCTGGA

GATGCTTCGGGACCAGCTGGCCAAGTGGCAGTGGGAGACCCACGACCCCT

GGGTGTGCGCCCCCGACGGCGTCCTGGAGGAGAAGCTCTCTCCCCAGTGC

CAGCCCCTACACAATGAGCTCTCATCTAGAGGATCCCGGGCTGACTACAA

AGACCATGACGGTGATTATAAAGATCATGACATCGACTACAAGGATGACG

ATGACAAGATCTCTGTCATTGATGCACTGCAGTACAAATTAGAGGGCACC

ACAAGATTGACAAGAAAAAGGGGATTGAAGTTAGCCACAGCTCTGTCTCT

GAGCAACAAATTTGTGGAGGGTAGTAGATCTTAGTGA-3'
```

SEQUENCES WITHOUT FLAG:

e) Assembly hAATsp-SGSH cassette.

(SEQ ID No. 19)

```
5'-

ATGCCGTCTTCTGTCTCGTGGGGCATCCTCCTGCTGGCAGGCCTGTGCTG

CCTGGTCCCTGTCTCCCTGGCTCGTCCCCGGAACGCACTGCTGCTCCTCG

CGGATGACGGAGGCTTTGAGAGTGGCGCGTACAACAACAGCGCCATCGCC

ACCCCGCACCTGGACGCCTTGGCCCGCCGCAGCCTCCTCTTTCGCAATGC

CTTCACCTCGGTCAGCAGCTGCTCTCCCAGCCGCGCCAGCCTCCTCACTG

GCCTGCCCCAGCATCAGAATGGGATGTACGGGCTGCACCAGGACGTGCAC

CACTTCAACTCCTTCGACAAGGTGCGGAGCCTGCCGCTGCTGCTCAGCCA

AGCTGGTGTGCGCACAGGCATCATCGGGAAGAAGCACGTGGGGCCGGAGA

CCGTGTACCCGTTTGACTTTGCGTACACGGAGGAGAATGGCTCCGTCCTC
```

-continued

CAGGTGGGGCGGAACATCACTAGAATTAAGCTGCTCGTCCGGAAATTCCT
GCAGACTCAGGATGACCGGCCTTTCTTCCTCTACGTCGCCTTCCACGACC
CCCACCGCTGTGGGCACTCCCAACCCCAGTACGGAACCTTCTGTGAGAAG
TTTGGCAACGGAGAGAGCGGCATGGGTCGTATCCCAGACTGGACCCCCCA
GGCCTACGACCCACTGGACGTGCTGGTGCCTTACTTCGTCCCCAACACCC
CGGCAGCCCGAGCCGACCTGGCCGCTCAGTACACCACCGTCGGCCGCATG
GACCAAGGAGTTGGACTGGTGCTCCAGGAGCTGCGTGACGCCGGTGTCCT
GAACGACACACTGGTGATCTTCACGTCCGACAACGGGATCCCCTTCCCCA
GCGGCAGGACCAACCTGTACTGGCCGGGCACTGCTGAACCCTTACTGGTG
TCATCCCCGGAGCACCCAAAACGCTGGGGCCAAGTCAGCGAGGCCTACGT
GAGCCTCCTAGACCTCACGCCCACCATCTTGGATTGGTTCTCGATCCCGT
ACCCCAGCTACGCCATCTTTGGCTCGAAGACCATCCACCTCACTGGCCGG
TCCCTCCTGCCGGCGCTGGAGGCCGAGCCCCTCTGGGCCACCGTCTTTGG
CAGCCAGAGCCACCACGAGGTCACCATGTCCTACCCCATGCGCTCCGTGC
AGCACCGGCACTTCCGCCTCGTGCACAACCTCAACTTCAAGATGCCCTTT
CCCATCGACCAGGACTTCTACGTCTCACCCACCTTCCAGGACCTCCTGAA
CCGCACCACAGCTGGTCAGCCCACGGGCTGGTACAAGGACCTCCGTCATT
ACTACTACCGGGCGCGCTGGGAGCTCTACGACCGGAGCCGGGACCCCCAC
GAGACCCAGAACCTGGCCACCGACCCGCGCTTTGCTCAGCTTCTGGAGAT
GCTTCGGGACCAGCTGGCCAAGTGGCAGTGGGAGACCCACGACCCCTGGG
TGTGCGCCCCGACGGCGTCCTGGAGGAGAAGCTCTCTCCCCAGTGCCAG
CCCCTCCACAATGAGCTGTGA-3' f) Assembly hIDSsp-SGSH cassette.

(SEQ ID No. 21)
5'-
ATGCCCCGCCCCGCACCGGCCGCGGCCTGCTGTGGCTGGGCCTGGTGCT
GAGCAGCGTGTGCGTGGCCCTGGGCCGTCCCCGGAACGCACTGCTGCTCC
TCGCGGATGACGGAGGCTTTGAGAGTGGCGCGTACAACAACAGCGCCATC
GCCACCCCGCACCTGGACGCCTTGGCCCGCCGCAGCCTCCTCTTTCGCAA
TGCCTTCACCTCGGTCAGCAGCTGCTCTCCCAGCCGCGCCAGCCTCCTCA
CTGGCCTGCCCCAGCATCAGAATGGGATGTACGGGCTGCACCAGGACGTG
CACCACTTCAACTCCTTCGACAAGGTGCGGAGCCTGCCGCTGCTGCTCAG
CCAAGCTGGTGTGCGCACAGGCATCATCGGGAAGAAGCACGTGGGGCCGG
AGACCGTGTACCCGTTTGACTTTGCGTACACGGAGGAGAATGGCTCCGTC
CTCCAGGTGGGGCGGAACATCACTAGAATTAAGCTGCTCGTCCGGAAATT
CCTGCAGACTCAGGATGACCGGCCTTTCTTCCTCTACGTCGCCTTCCACG
ACCCCCACCGCTGTGGGCACTCCCAACCCCAGTACGGAACCTTCTGTGAG
AAGTTTGGCAACGGAGAGAGCGGCATGGGTCGTATCCCAGACTGGACCCC
CCAGGCCTACGACCCACTGGACGTGCTGGTGCCTTACTTCGTCCCCAACA
CCCCGGCAGCCCGAGCCGACCTGGCCGCTCAGTACACCACCGTCGGCCGC
ATGGACCAAGGAGTTGGACTGGTGCTCCAGGAGCTGCGTGACGCCGGTGT
CCTGAACGACACACTGGTGATCTTCACGTCCGACAACGGGATCCCCTTCC

-continued

CCAGCGGCAGGACCAACCTGTACTGGCCGGGCACTGCTGAACCCTTACTG
GTGTCATCCCCGGAGCACCCAAAACGCTGGGGCCAAGTCAGCGAGGCCTA
CGTGAGCCTCCTAGACCTCACGCCCACCATCTTGGATTGGTTCTCGATCC
CGTACCCCAGCTACGCCATCTTTGGCTCGAAGACCATCCACCTCACTGGC
CGGTCCCTCCTGCCGGCGCTGGAGGCCGAGCCCCTCTGGGCCACCGTCTT
TGGCAGCCAGAGCCACCACGAGGTCACCATGTCCTACCCCATGCGCTCCG
TGCAGCACCGGCACTTCCGCCTCGTGCACAACCTCAACTTCAAGATGCCC
TTTCCCATCGACCAGGACTTCTACGTCTCACCCACCTTCCAGGACCTCCT
GAACCGCACCACAGCTGGTCAGCCCACGGGCTGGTACAAGGACCTCCGTC
ATTACTACTACCGGGCGCGCTGGGAGCTCTACGACCGGAGCCGGGACCCC
CACGAGACCCAGAACCTGGCCACCGACCCGCGCTTTGCTCAGCTTCTGGA
GATGCTTCGGGACCAGCTGGCCAAGTGGCAGTGGGAGACCCACGACCCCT
GGGTGTGCGCCCCGACGGCGTCCTGGAGGAGAAGCTCTCTCCCCAGTGC
CAGCCCCTACACAATGAGCTCTGA-3' g) Assembly hAATsp-SGSH-ApoB cassette.

(SEQ ID No. 23)
5'-
ATGCCGTCTTCTGTCTCGTGGGGCATCCTCCTGCTGGCAGGCCTGTGCTG
CCTGGTCCCTGTCTCCCTGGCTCGTCCCCGGAACGCACTGCTGCTCCTCG
CGGATGACGGAGGCTTTGAGAGTGGCGCGTACAACAACAGCGCCATCGCC
ACCCCGCACCTGGACGCCTTGGCCCGCCGCAGCCTCCTCTTTCGCAATGC
CTTCACCTCGGTCAGCAGCTGCTCTCCCAGCCGCGCCAGCCTCCTCACTG
GCCTGCCCCAGCATCAGAATGGGATGTACGGGCTGCACCAGGACGTGCAC
CACTTCAACTCCTTCGACAAGGTGCGGAGCCTGCCGCTGCTGCTCAGCCA
AGCTGGTGTGCGCACAGGCATCATCGGGAAGAAGCACGTGGGGCCGGAGA
CCGTGTACCCGTTTGACTTTGCGTACACGGAGGAGAATGGCTCCGTCCTC
CAGGTGGGGCGGAACATCACTAGAATTAAGCTGCTCGTCCGGAAATTCCT
GCAGACTCAGGATGACCGGCCTTTCTTCCTCTACGTCGCCTTCCACGACC
CCCACCGCTGTGGGCACTCCCAACCCCAGTACGGAACCTTCTGTGAGAAG
TTTGGCAACGGAGAGAGCGGCATGGGTCGTATCCCAGACTGGACCCCCCA
GGCCTACGACCCACTGGACGTGCTGGTGCCTTACTTCGTCCCCAACACCC
CGGCAGCCCGAGCCGACCTGGCCGCTCAGTACACCACCGTCGGCCGCATG
GACCAAGGAGTTGGACTGGTGCTCCAGGAGCTGCGTGACGCCGGTGTCCT
GAACGACACACTGGTGATCTTCACGTCCGACAACGGGATCCCCTTCCCCA
GCGGCAGGACCAACCTGTACTGGCCGGGCACTGCTGAACCCTTACTGGTG
TCATCCCCGGAGCACCCAAAACGCTGGGGCCAAGTCAGCGAGGCCTACGT
GAGCCTCCTAGACCTCACGCCCACCATCTTGGATTGGTTCTCGATCCCGT
ACCCCAGCTACGCCATCTTTGGCTCGAAGACCATCCACCTCACTGGCCGG
TCCCTCCTGCCGGCGCTGGAGGCCGAGCCCCTCTGGGCCACCGTCTTTGG
CAGCCAGAGCCACCACGAGGTCACCATGTCTTACCCCATGCGCTCCGTGC
AGCACCGGCACTTCCGCCTCGTGCACAACCTCAACTTCAAGATGCCCTTT
CCCATCGACCAGGACTTCTACGTCTCACCCACCTTCCAGGACCTCCTGAA

-continued
CCGCACCACAGCTGGTCAGCCCACGGGCTGGTACAAGGACCTCCGTCATT

ACTACTACCGGGCGCGCTGGGAGCTCTACGACCGGAGCCGGGACCCCAC

GAGACCCAGAACCTGGCCACCGACCCGCGCTTTGCTCAGCTTCTGGAGAT

GCTTCGGGACCAGCTGGCCAAGTGGCAGTGGGAGACCCACGACCCCTGGG

TGTGCGCCCCGACGGCGTCCTGGAGGAGAAGCTCTCTCCCCAGTGCCAG

CCCCTCCACAATGAGCTGTCATCTAGATCTGTCATTGATGCACTGCAGTA

CAAATTAGAGGGCACCACAAGATTGACAAGAAAAAGGGGATTGAAGTTAG

CCACAGCTCTGTCTCTGAGCAACAAATTTGTGGAGGGTAGTAGATCTTAG

TGA-3' h) Assembly hIDSsp-SGSH-ApoB cassette.
(SEQ ID No. 25)
5'-
ATGCCCCCGCCCCGCACCGGCCGCGGCCTGCTGTGGCTGGGCCTGGTGCT

GAGCAGCGTGTGCGTGGCCCTGGGCCGTCCCCGGAACGCACTGCTGCTCC

TCGCGGATGACGGAGGCTTTGAGAGTGGCGCGTACAACAACAGCGCCATC

GCCACCCCGCACCTGGACGCCTTGGCCCGCCGCAGCCTCCTCTTTCGCAA

TGCCTTCACCTCGGTCAGCAGCTGCTCTCCCAGCCGCGCCAGCCTCCTCA

CTGGCCTGCCCCAGCATCAGAATGGGATGTACGGGCTGCACCAGGACGTG

CACCACTTCAACTCCTTCGACAAGGTGCGGAGCCTGCCGCTGCTGCTCAG

CCAAGCTGGTGTGCGCACAGGCATCATCGGGAAGAAGCACGTGGGGCCGG

AGACCGTGTACCCGTTTGACTTTGCGTACACGGAGGAGAATGGCTCCGTC

CTCCAGGTGGGGCGGAACATCACTAGAATTAAGCTGCTCGTCCGGAAATT

CCTGCAGACTCAGGATGACCGGCCTTTCTTCCTCTACGTCGCCTTCCACG

ACCCCCACCGCTGTGGGCACTCCCAACCCCAGTACGGAACCTTCTGTGAG

AAGTTTGGCAACGGAGAGAGCGGCATGGGTCGTATCCCAGACTGGACCCC

CCAGGCCTACGACCCACTGGACGTGCTGGTGCCTTACTTCGTCCCCAACA

CCCCGGCAGCCCGAGCCGACCTGGCCGCTCAGTACACCACCGTCGGCCGC

ATGGACCAAGGAGTTGGACTGGTGCTCCAGGAGCTGCGTGACGCCGGTGT

CCTGAACGACACACTGGTGATCTTCACGTCCGACAACGGGATCCCCTTCC

CCAGCGGCAGGACCAACCTGTACTGGCCGGGCACTGCTGAACCCTTACTG

GTGTCATCCCCGGAGCACCCAAAACGCTGGGGCCAAGTCAGCGAGGCCTA

CGTGAGCCTCCTAGACCTCACGCCCACCATCTTGGATTGGTTCTCGATCC

CGTACCCCAGCTACGCCATCTTTGGCTCGAAGACCATCCACCTCACTGGC

CGGTCCCTCCTGCCGGCGCTGGAGGCCGAGCCCCTCTGGGCCACCGTCTT

TGGCAGCCAGAGCCACCACGAGGTCACCATGTCTTACCCCATGCGCTCCG

TGCAGCACCGGCACTTCCGCCTCGTGCACAACCTCAACTTCAAGATGCCC

TTTCCCATCGACCAGGACTTCTACGTCTCACCCACCTTCCAGGACCTCCT

GAACCGCACCACAGCTGGTCAGCCCACGGGCTGGTACAAGGACCTCCGTC

ATTACTACTACCGGGCGCGCTGGGAGCTCTACGACCGGAGCCGGGACCCC

CACGAGACCCAGAACCTGGCCACCGACCCGCGCTTTGCTCAGCTTCTGGA

GATGCTTCGGGACCAGCTGGCCAAGTGGCAGTGGGAGACCCACGACCCCT

GGGTGTGCGCCCCGACGGCGTCCTGGAGGAGAAGCTCTCTCCCCAGTGC

-continued
CAGCCCCTCCACAATGAGCTGTCATCTAGATCTGTCATTGATGCACTGCA

GTACAAATTAGAGGGCACCACAAGATTGACAAGAAAAAGGGGATTGAAGT

TAGCCACAGCTCTGTCTCTGAGCAACAAATTTGTGGAGGGTAGTAGATCT

TAGTGA-3'.

It is a further object of the invention a recombinant plasmid suitable for gene therapy of MPS comprising the nucleotide sequence as above disclosed under the control of a liver specific promoter, preferably the liver specific promoter is the human thyroid hormone-globulin (TBG) promoter, more preferably the human thyroid hormone-globulin (TBG) promoter has essentially the sequence:

(SEQ ID No. 27)
5'-GCTAGCAGGTTAATTTTTAAAAAGCAGTCAAAAGTCCAAGTGGCCCT

TGGCAGCATTTACTCTCTCTGTTTGCTCTGGTTAATAATCTCAGGAGCAC

AAACATTCCAGATCCAGGTTAATTTTTAAAAAGCAGTCAAAAGTCCAAGT

GGCCCTTGGCAGCATTTACTCTCTCTGTTTGCTCTGGTTAATAATCTCAG

GAGCACAAACATTCCAGATCCGGCGCGCCAGGGCTGGAAGCTACCTTTGA

CATCATTTCCTCTGCGAATGCATGTATAATTTCTACAGAACCTATTAGAA

AGGATCACCCAGCCTCTGCTTTTGTACAACTTTCCCTTAAAAAACTGCCA

ATTCCACTGCTGTTTGGCCCAATAGTGAGAACTTTTTCCTGCTGCCTCTT

GGTGCTTTTGCCTATGGCCCCTATTCTGCCTGCTGAAGACACTCTTGCCA

GCATGGACTTAAACCCCTCCAGCTCTGACAATCCTCTTTCTCTTTTGTTT

TACATGAAGGGTCTGGCAGCCAAAGCAATCACTCAAAGTTCAAACCTTAT

CATTTTTTGCTTTGTTCCTCTTGGCCTTGGTTTTGTACATCAGCTTTGAA

AATACCATCCCAGGGTTAATGCTGGGGTTAATTTATAACTAAGAGTGCTC

TAGTTTTGCAATACAGGACATGCTATAAAAATGGAAAGATGTTGCTTTCT

GAGAGACTGCAG-3'.

The expert in the field will realize that the recombinant plasmid of the invention has to be assembled in a viral vector for gene therapy of lysosomal disorders, and select the most suitable one. Such viral vectors may belong to the group of: lentiviral vectors, helper-dependent adenoviral vectors or AAV vectors. As example lentiviral vectors for gene therapy of lysosomal storage disorders is described in Naldini, L., Blomer, U., Gage, F. H., Trono, D., and Verma, I. M. (1996a). In vivo gene delivery and stable transduction of nondividing cells by a lentiviral vector. *Science* 272(5259), 263-7; Consiglio A, Quattrini A, Martino S, Bensadoun J C, Dolcetta D, Trojani A, Benaglia G, Marchesini S, Cestari V, Oliverio A, Bordignon C, Naldini. In vivo gene therapy of metachromatic leukodystrophy by lentiviral vectors: correction of neuropathology and protection against learning impairments in affected mice L. *Nat Med.* 2001 March; 7(3):310-6; Follenzi A, Naldini L. HIV-based vectors. Preparation and use. Methods Mol Med. 2002;69:259-74. As a further example helper-dependent adenoviral vectors are described in Brunetti-Pierri N, Ng P. Progress towards liver and lung-directed gene therapy with helper-dependent adenoviral vectors. Curr Gene Ther. 2009 October; 9(5):329-40.

In a preferred embodiment the recombinant plasmid derives from the plasmid vector AAV2.1 and is suitable for AAV viral vectors, preferably AAV serotype 8.

Then it is a further object of the invention a viral vector for gene therapy of lysosomal disorders comprising any of the recombinant nucleic acid vectors as above disclosed. Preferably the lysosomal disorder is MPS, more preferably MPS type IIIA.

It is a further object of the invention a pharmaceutical composition comprising the viral vector as above disclosed, preferably for systemic administration.

It is a further object of the invention a chimeric sulfatase essentially consisting in the N-terminal-C-terminal sequence order of a) a signal peptide derived by either the human a-antitrypsin (hAAT) amino acid sequence or the human Iduronate-2-sulfatase (IDS) amino acid sequence; b) an human sulfatase derived amino acid sequence deprived of its signal peptide; c) the ApoB LDLR-binding domain.

In a preferred embodiment the chimeric sulfatase has a signal peptide having a sequence belonging to the following group: (SEQ ID No. 2) or (SEQ ID No. 4).

In a preferred embodiment the chimeric sulfatase has a human sulfamidase derived sequence, preferably (SEQ ID No. 8).

In a preferred embodiment the chimeric sulfatase comprises an encoded ApoB LDLR-binding domain having essentially the sequence of (SEQ ID No. 10).

In a preferred embodiment the chimeric sulfatase has essentially the sequence belonging to the following group:

```
SEQUENCE WITH FLAG (expert shall easily substi-
tute the flag sequence with any other suitable
spacer sequence):
a) hAATsp-SGSH-3xflag aminoacid sequence (* =
stop).
                                      (SEQ ID No. 12)
MPSSVSWGILLLAGLCCLVPVSLARPRNALLLLADDGGFESGAYNNSAIA

TPHLDALARRSLLFRNAFTSVSSCSPSRASLLTGLPQHQNGMYGLHQDVH

HFNSFDKVRSLPLLLSQAGVRTGIIGKKHVGPETVYPFDFAYTEENGSVL

QVGRNITRIKLLVRKFLQTQDDRPFFLYVAFHDPHRCGHSQPQYGTFCEK

FGNGESGMGRIPDWTPQAYDPLDVLVPYFVPNTPAARADLAAQYTTVGRM

DQGVGLVLQELRDAGVLNDTLVIFTSDNGIPFPSGRTNLYWPGTAEPLLV

SSPEHPKRWGQVSEAYVSLLDLTPTILDWFSIPYPSYAIFGSKTIHLTGR

SLLPALEAEPLWATVFGSQSHHEVTMSYPMRSVQHRHFRLVHNLNFKMPF

PIDQDFYVSPTFQDLLNRTTAGQPTGWYKDLRHYYYRARWELYDRSRDPH

ETQNLATDPRFAQLLEMLRDQLAKWQWETHDPWVCAPDGVLEEKLSPQCQ

PLHNELSSRGSRADYKDHDGDYKDHDIDYKDDDDK** b) hIDSsp-SGSH-3xflag aminoacid sequence (* =
stop)
                                      (SEQ ID No. 14)
MPPPRTGRGLLWLGLVLSSVCVALGRPRNALLLLADDGGFESGAYNNSAI

ATPHLDALARRSLLFRNAFTSVSSCSPSRASLLTGLPQHQNGMYGLHQDV

HHFNSFDKVRSLPLLLSQAGVRTGIIGKKHVGPETVYPFDFAYTEENGSV

LQVGRNITRIKLLVRKFLQTQDDRPFFLYVAFHDPHRCGHSQPQYGTFCE

KFGNGESGMGRIPDWTPQAYDPLDVLVPYFVPNTPAARADLAAQYTTVGR

MDQGVGLVLQELRDAGVLNDTLVIFTSDNGIPFPSGRTNLYWPGTAEPLL

VSSPEHPKRWGQVSEAYVSLLDLTPTILDWFSIPYPSYAIFGSKTIHLTG

RSLLPALEAEPLWATVFGSQSHHEVTMSYPMRSVQHRHFRLVHNLNFKMP

-continued
FPIDQDFYVSPTFQDLLNRTTAGQPTGWYKDLRHYYYRARWELYDRSRDP

HETQNLATDPRFAQLLEMLRDQLAKWQWETHDPWVCAPDGVLEEKLSPQC

QPLHNELSSRGSRADYKDHDGDYKDHDIDYKDDDDK** c) hAATsp-SGSH-3xflag-ApoB aminoacid sequence
(* = stop)
                                      (SEQ ID No. 16)
MPSSVSWGILLLAGLCCLVPVSLARPRNALLLLADDGGFESGAYNNSAIA

TPHLDALARRSLLFRNAFTSVSSCSPSRASLLTGLPQHQNGMYGLHQDVH

HFNSFDKVRSLPLLLSQAGVRTGIIGKKHVGPETVYPFDFAYTEENGSVL

QVGRNITRIKLLVRKFLQTQDDRPFFLYVAFHDPHRCGHSQPQYGTFCEK

FGNGESGMGRIPDWTPQAYDPLDVLVPYFVPNTPAARADLAAQYTTVGRM

DQGVGLVLQELRDAGVLNDTLVIFTSDNGIPFPSGRTNLYWPGTAEPLLV

SSPEHPKRWGQVSEAYVSLLDLTPTILDWFSIPYPSYAIFGSKTIHLTGR

SLLPALEAEPLWATVFGSQSHHEVTMSYPMRSVQHRHFRLVHNLNFKMPF

PIDQDFYVSPTFQDLLNRTTAGQPTGWYKDLRHYYYRARWELYDRSRDPH

ETQNLATDPRFAQLLEMLRDQLAKWQWETHDPWVCAPDGVLEEKLSPQCQ

PLHNELSSRGSRADYKDHDGDYKDHDIDYKDDDDKISVIDALQYKLEGTT

RLTRKRGLKLATALSLSNKFVEGSRS** d) hIDSsp-SGSH-3xflag-ApoB aminoacid sequence
(* = stop)
                                      (SEQ ID No. 18)
MPPPRTGRGLLWLGLVLSSVCVALGRPRNALLLLADDGGFESGAYNNSAI

ATPHLDALARRSLLFRNAFTSVSSCSPSRASLLTGLPQHQNGMYGLHQDV

HHFNSFDKVRSLPLLLSQAGVRTGIIGKKHVGPETVYPFDFAYTEENGSV

LQVGRNITRIKLLVRKFLQTQDDRPFFLYVAFHDPHRCGHSQPQYGTFCE

KFGNGESGMGRIPDWTPQAYDPLDVLVPYFVPNTPAARADLAAQYTTVGR

MDQGVGLVLQELRDAGVLNDTLVIFTSDNGIPFPSGRTNLYWPGTAEPLL

VSSPEHPKRWGQVSEAYVSLLDLTPTILDWFSIPYPSYAIFGSKTIHLTG

RSLLPALEAEPLWATVFGSQSHHEVTMSYPMRSVQHRHFRLVHNLNFKMP

FPIDQDFYVSPTFQDLLNRTTAGQPTGWYKDLRHYYYRARWELYDRSRDP

HETQNLATDPRFAQLLEMLRDQLAKWQWETHDPWVCAPDGVLEEKLSPQC

QPLHNELSSRGSRADYKDHDGDYKDHDIDYKDDDDKISVIDALQYKLEGT

TRLTRKRGLKLATALSLSNKFVEGSRS**,

SEQUENCES WITHOUT FLAG:
e) hAATsp-SGSH aminoacid sequence (* = stop)
                                      (SEQ ID No. 20)
MPSSVSWGILLLAGLCCLVPVSLARPRNALLLLADDGGFESGAYNNSAIA

TPHLDALARRSLLFRNAFTSVSSCSPSRASLLTGLPQHQNGMYGLHQDVH

HFNSFDKVRSLPLLLSQAGVRTGIIGKKHVGPETVYPFDFAYTEENGSVL

QVGRNITRIKLLVRKFLQTQDDRPFFLYVAFHDPHRCGHSQPQYGTFCEK

FGNGESGMGRIPDWTPQAYDPLDVLVPYFVPNTPAARADLAAQYTTVGRM

DQGVGLVLQELRDAGVLNDTLVIFTSDNGIPFPSGRTNLYWPGTAEPLLV

SSPEHPKRWGQVSEAYVSLLDLTPTILDWFSIPYPSYAIFGSKTIHLTGR

SLLPALEAEPLWATVFGSQSHHEVTMSYPMRSVQHRHFRLVHNLNFKMPF

PIDQDFYVSPTFQDLLNRTTAGQPTGWYKDLRHYYYRARWELYDRSRDPH
```

-continued

ETQNLATDPRFAQLLEMLRDQLAKWQWETHDPWVCAPDGVLEEKLSPQCQ

PLHNEL* f) hIDSsp-SGSH aminoacid sequence (* = stop)
(SEQ ID No. 22)
MPPPRTGRGLLWLGLVLSSVCVALGRPRNALLLLADDGGFESGAYNNSAI

ATPHLDALARRSLLFRNAFTSVSSCSPSRASLLTGLPQHQNGMYGLHQDV

HHFNSFDKVRSLPLLLSQAGVRTGIIGKKHVGPETVYPFDFAYTEENGSV

LQVGRNITRIKLLVRKFLQTQDDRPFFLYVAFHDPHRCGHSQPQYGTFCE

KFGNGESGMGRIPDWTPQAYDPLDVLVPYFVPNTPAARADLAAQYTTVGR

MDQGVGLVLQELRDAGVLNDTLVIFTSDNGIPFPSGRTNLYWPGTAEPLL

VSSPEHPKRWGQVSEAYVSLLDLTPTILDWFSIPYPSYAIFGSKTIHLTG

RSLLPALEAEPLWATVFGSQSHHEVTMSYPMRSVQRHFRLVHNLNFKMP

FPIDQDFYVSPTFQDLLNRTTAGQPTGWYKDLRHYYYRARWELYDRSRDP

HETQNLATDPRFAQLLEMLRDQLAKWQWETHDPWVCAPDGVLEEKLSPQC

QPLHNEL* g) hAATsp-SGSH-ApoB aminoacid sequence (* = stop)
(SEQ ID No. 24)
MPSSVSWGILLLAGLCCLVPVSLARPRNALLLLADDGGFESGAYNNSAIA

TPHLDALARRSLLFRNAFTSVSSCSPSRASLLTGLPQHQNGMYGLHQDVH

HFNSFDKVRSLPLLLSQAGVRTGIIGKKHVGPETVYPFDFAYTEENGSVL

QVGRNITRIKLLVRKFLQTQDDRPFFLYVAFHDPHRCGHSQPQYGTFCEK

FGNGESGMGRIPDWTPQAYDPLDVLVPYFVPNTPAARADLAAQYTTVGRM

DQGVGLVLQELRDAGVLNDTLVIFTSDNGIPFPSGRTNLYWPGTAEPLLV

SSPEHPKRWGQVSEAYVSLLDLTPTILDWFSIPYPSYAIFGSKTIHLTGR

SLLPALEAEPLWATVFGSQSHHEVTMSYPMRSVQRHFRLVHNLNFKMPF

PIDQDFYVSPTFQDLLNRTTAGQPTGWYKDLRHYYYRARWELYDRSRDPH

ETQNLATDPRFAQLLEMLRDQLAKWQWETHDPWVCAPDGVLEEKLSPQCQ

PLHNELSSRSVIDALQYKLEGTTRLTRKRGLKLATALSLSNKFVEGSRS*

* h) hIDSsp-SGSH-ApoB aminoacid sequence (* = stop)
(SEQ ID No. 26)
MPPPRTGRGLLWLGLVLSSVCVALGRPRNALLLLADDGGFESGAYNNSAI

ATPHLDALARRSLLFRNAFTSVSSCSPSRASLLTGLPQHQNGMYGLHQDV

HHFNSFDKVRSLPLLLSQAGVRTGIIGKKHVGPETVYPFDFAYTEENGSV

LQVGRNITRIKLLVRKFLQTQDDRPFFLYVAFHDPHRCGHSQPQYGTFCE

KFGNGESGMGRIPDWTPQAYDPLDVLVPYFVPNTPAARADLAAQYTTVGR

MDQGVGLVLQELRDAGVLNDTLVIFTSDNGIPFPSGRTNLYWPGTAEPLL

VSSPEHPKRWGQVSEAYVSLLDLTPTILDWFSIPYPSYAIFGSKTIHLTG

RSLLPALEAEPLWATVFGSQSHHEVTMSYPMRSVQRHFRLVHNLNFKMP

FPIDQDFYVSPTFQDLLNRTTAGQPTGWYKDLRHYYYRARWELYDRSRDP

HETQNLATDPRFAQLLEMLRDQLAKWQWETHDPWVCAPDGVLEEKLSPQC

QPLHNELSSRSVIDALQYKLEGTTRLTRKRGLKLATALSLSNKFVEGSRS

**

It is another object of the invention the chimeric sulfatase as above disclosed for medical use, preferably for the treatment of MPS, more preferably MPS type IIIA.

It is another object of the invention a pharmaceutical composition comprising the chimeric sulfatase as above disclosed and suitable diluents and/or eccipients and/or carriers.

It is another object of the invention a method for treatment of a MPS pathology comprising the step of administering to a subject a suitable amount of the pharmaceutical composition comprising the viral vector for gene therapy as above disclosed. Preferably the MPS pathology is MPS type IIIA.

It is another object of the invention a method for treatment of a MPS pathology comprising the step of administering to a subject a suitable amount of the pharmaceutical composition comprising the chimeric sulfatase as above disclosed. Preferably the MPS pathology is MPS type IIIA.

Major advantage of the invention is that the chimeric molecule of the invention as produced and secreted by the liver is able to cross the BBB and thus potentially target to all brain districts.

Regarding the gene therapy approach, with respect to prior art Fraldi et al. HMG 2007 that describes AAV2/5 mediated gene therapy for MPS-IIIA, the instant invention is less invasive because AAV8 vectors are administered systemically and not directly into the brain.

As to the enzyme replacement therapy approach with respect to the prior art Hemsley, K. M. and J. J. Hopwood, Behav Brain Res, 2005; Savas, P. S et al., Mol Genet Metab, 2004 and Hemsley, K. M., et al., Mol Genet Metab, 2007, the instant invention overcomes the necessity to repeat the injection of the enzyme and it is designed to cross the BBB. It is worth to point out that for ERT approaches the BBB and the high cost of the enzyme production are very important limitations.

FIG. 4. Non-modified SGSH: Preliminary in vivo study 2 (adult treatment). SGSH activity in the serum and liver of adult injected mice. The sulfamidase activity was measured in the serum (A) and liver (B) of MPSIIIA mice injected with AAV2/8-TBG-SGSH and control mice (MPS-IIIA and heterozygous mice injected with AAV2/8-TBG-GFP). (A) In the liver of MPSIIIA mice injected with AAV2/8-TBG-SGSH a strong increase in the SGSH activity was observed compared to the low enzyme activity detected in the animals injected with GFP vector. In addition, this activity remained stable for 5 weeks after injection (the last time point analyzed). (B) Consistently, the analysis of SGSH activity in the serum of MPS-IIIA mice treated with AAV2/8-TBG-SGSH was very high and stable during throughout the analyzed post-injection time.

Figure 5:
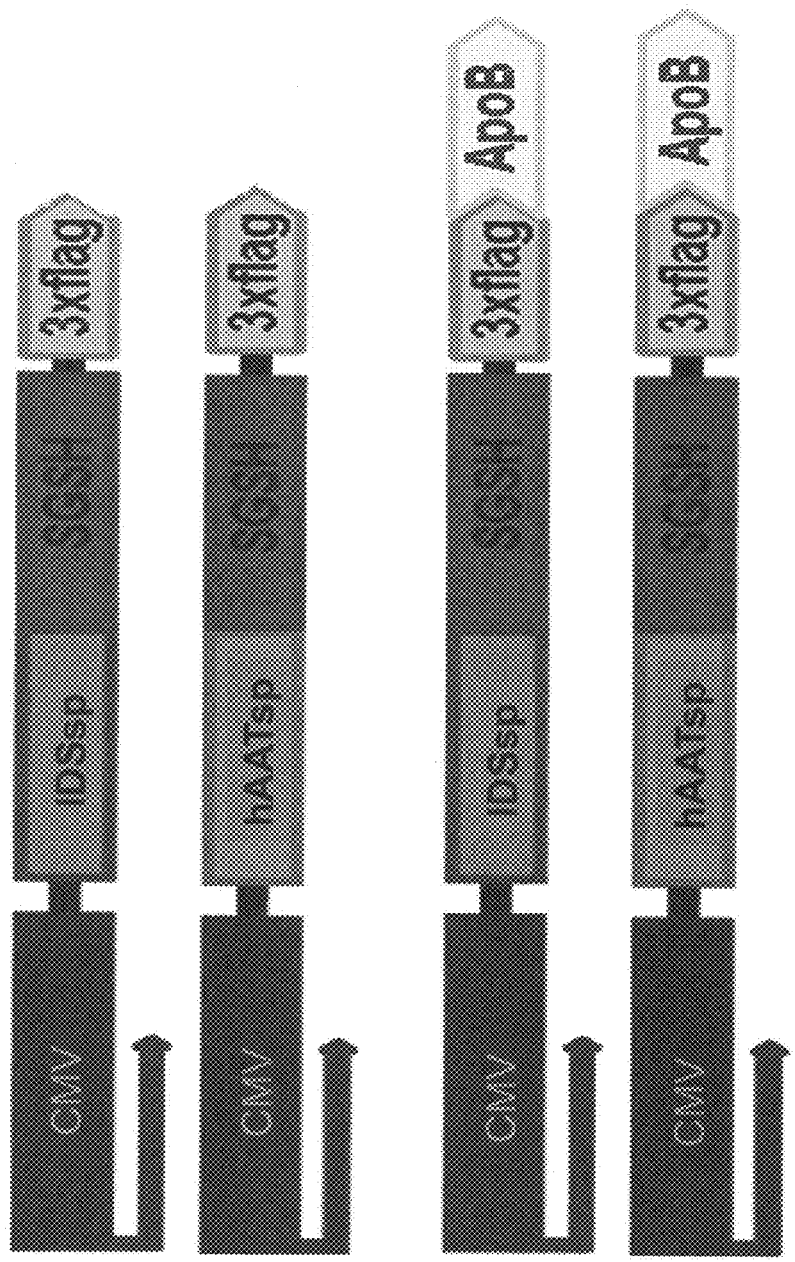

FIG. 5. Chimeric sulfamidase constructs. The signal peptide (SP) of sulfamidase was replaced with that of either human a-antitrypsin (hAAT) or Iduronate-2-sulfatase (IDS). The constructs were designed as "partially engineered sulfamidase proteins" (IDSsp-SGSHflag and hAATsp-SGSHflag). To build the final chimeric sulfamidase proteins, the ApoB LDLR-binding domain (ApoB-BD) was fused at the C-terminus of the Flag tag to obtain the resulting "finally engineered constructs" (IDSsp-SGSHflag-ApoB and hAATsp-SGSHflag-ApoB). The ApoB sequence (114 bp) was amplified by PCR from the human blood cDNA using forward and reverse oligonucleotides with 5' BglII sites. The backbone plasmid containing the SP-SGSH sequence was prepared inserting by mutagenesis the BglII site before the stop codon of Flag tag. All the resulting chimeric sulfamidase sequences (IDSsp-SGSHflag, hAATsp-SGSHflag, IDSsp-SGSHflag-ApoB and hAATsp-SGSHflag-ApoB) were inserted in mammalian expression plasmids under a CMV promoter.

Figure 6:
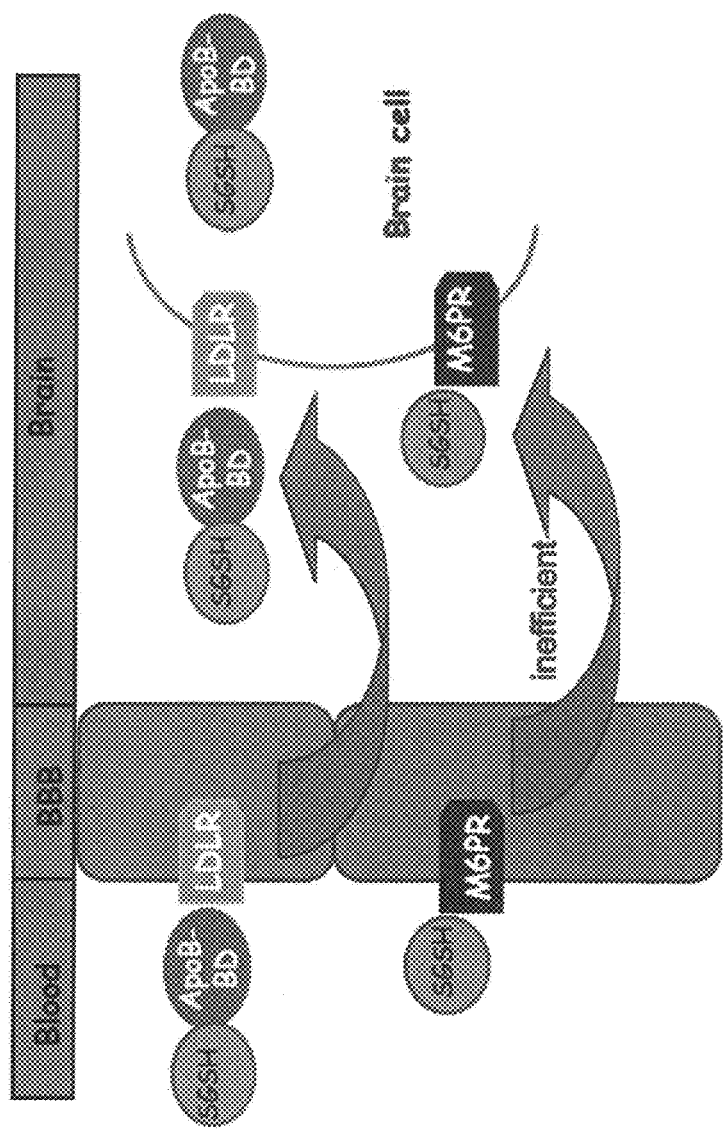

FIG. 6. Receptor-mediated transport. Crossing the BBB via receptor-mediated transcytosis. The Low Density Lipoprotein receptor (LDLR)-binding domain of the Apolipoprotein B (ApoB LDLR-BD) confers to the sulfamidase the capability to reach the brain cells by binding LDL receptors, which are abundant on the endothelial cells of BBB. This mechanism may substitute the mannose-6-phosphate receptor (M6PR)-mediated transport of the sulfamidase throughout the BBB, which is inefficient.

FIG. 7. In vitro study. SGSH activity in the pellet and in the medium of transfected MPS-IIIA MEF cells. MEF cells derived from MPS-IIIA mice were transfected with either partially or finally engineered constructs. (A) The activity of sulfamidase was measured in the medium (light grey) and in the pellet (dark grey) of transfected cells. (B) The corresponding efficiency of secretion (activity in medium/total activity) was also evaluated.

Figure 8:
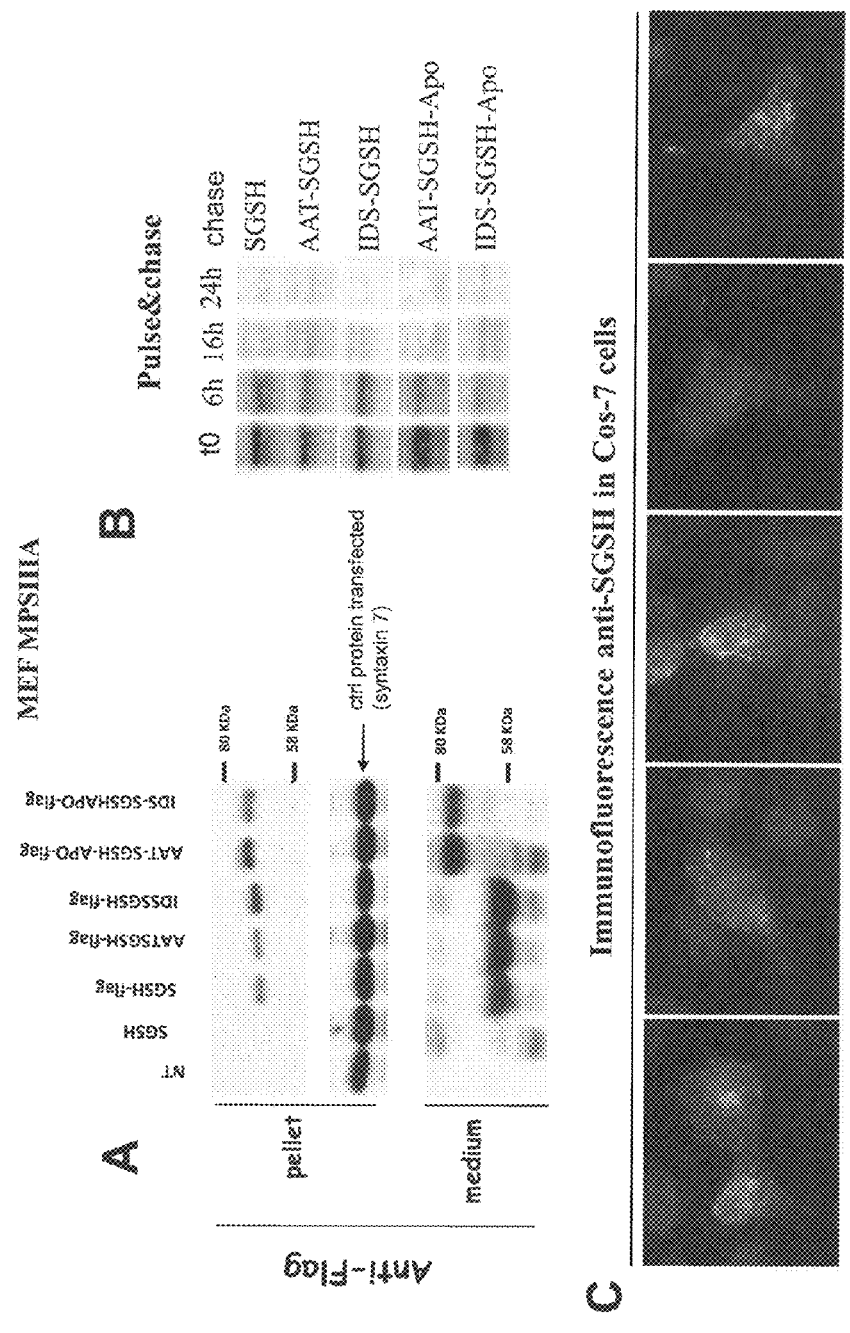

FIG. 8. In vitro study. Western blot analysis of all engineered sulfamidase proteins. MEF cells derived from MPS-IIIA mice were transfected with either partial or final engineered constructs or with control SGSH not modified construct. (A) blot analysis with anti-flag antibodies showing the correct expression of all the chimeric proteins. As a control of transfection efficiency the cells were co-transfected with the same concentration of a plasmid containing flag-tagged Syntaxin7, an unrelated protein. (B) Pulse and chase experiments were performed in the transfected cells to evaluate the turnover rate of the chimeric proteins (C) Cos-7 cells were transfected with either partially or finally engineered constructs or with control SGSH non modified construct. Lysosomal localization were observed in all transfected cells by immunostaining with anti-SGSH antibodies.

Figure 9:
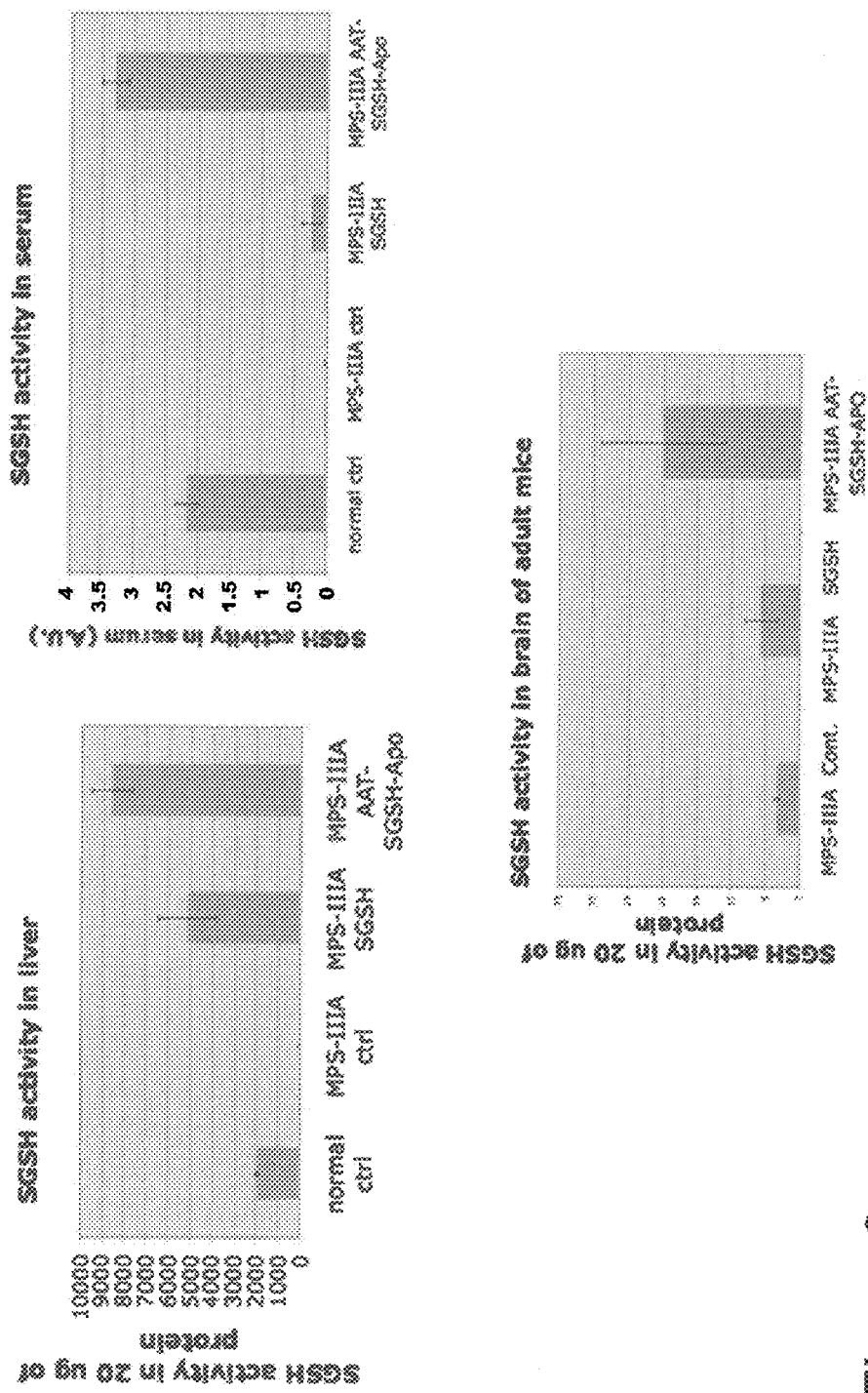

FIG. 9. In vivo study. Preliminary in vivo results in MPS IIIA mice injected with finally engineered sulfamidase. Authors obtained preliminary but extremely encouraging results in MPS-IIIA mice injected with one of the final sulfamidase constructs: hAATsp-SGSHflag-ApoB. Adult MPS-IIIA mice were systemically injected with AAV2/8-TBG-hAATsp-SGSHflag-ApoB. A group of MPS-IIIA were also injected with AAV2/8-TBG-SGSH (containing the non-modified sulfamidase) as control. The mice were sacrificed one month after injection. In the mice injected with the chimeric sulfamidase we observed higher liver sulfamidase activity and a very strong increase in the sulfamidase secretion with respect to control mice. Moreover, we detected a significant increase in SGSH activity into the brain of mice injected with the chimeric sulfamidase compared to SGSH activity measures in the brain of mice injected with not-modified sulfamidase.

Figure 10:
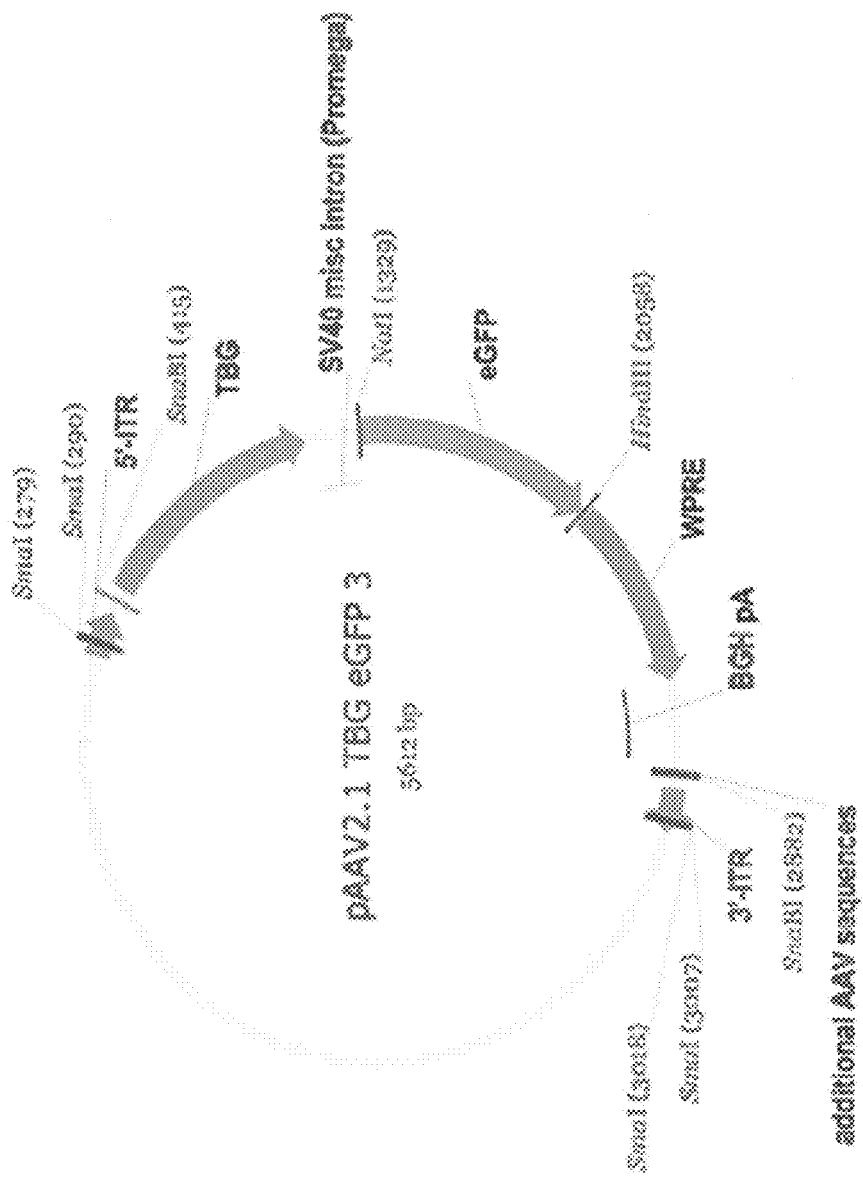

FIG. 10. Map of AAV2.1 plasmid. Map of pAAV2.1 plasmid used for AAV2.8 viral vectors production. The plasmid contains the GFP gene under the control of the liver specific promoter TBG. The GFP sequence was replaced with the cDNAs coding the chimeric sulfamidase cassettes by using NotI and HindIII restriction sites. The resulting plasmid was transfected along with pAd helper, pAAV rep-cap plasmid in 293 cells to produce AAV2.8 viral vectors (see Methods).

DETAILED DESCRIPTION OF THE INVENTION

Methods
Construction of Chimeric SGSH Cassettes, Recombinant Nucleic Acid Vectors and Viral Vectors The alternative signal peptides were produced by ligation of two fragments: a sequence from human SGSH cDNA (fragment I) and the signal peptide sequence (fragment II). Fragment I was amplified from a hSGSH expressing plasmid and started at the 3' terminus of hSGSH signal peptide sequence (corresponding to the nucleotide in position 61 on the SGSH sequence) and extended to a unique XbaI site and contained the entire SGSH cDNA (oligos used: SGSHFOR 5'-CGT CCC CGG AAC GCA CTG CTG CTC CT-3' (SEQ ID No. 28) and SGSHREV 5'-GCG GCC TCT AGA TGA CAG CTC ATT GTG GAG GGG CTG-3' (SEQ ID No. 29)). Fragment II was unique for each expression cassette. For hAATsp-SGSH-cFlag, fragment II was synthesized by annealing two specific oligonucleotide sequences (hAATsp-FOR 5'-GGC CGC ATG CCG TCT TCT GTC TCG TGG GGC ATC CTC CTG CTG GCA GGC CTG TGC TGC CTG GTC CCT GTC TCC CTG GCT 3' (SEQ ID No. 30) and hAATspREV 5'-AGC CAG GGA GAC AGG GAC CAG GCA GCA CAG GCC TGC CAG CAG GAG GAT GCC CCACGA GAC AGA AGA CGG CAT GC-3' (SEQ ID No. 31)) containing the human α1-antitrypsin signal peptide sequence [human a1-antitrypsin cDNA: 72 bp].

The fragment encoding for such signal peptide was:

(SEQ ID No. 1)
5'-ATGCCGTCTTCTGTCTCGTGGGGCATCCTCCTGCTGGCAGGCCTGTG

CTGCCTGGTCCCTGTCTCCCTGGCT-3'.

For IDSsp-SGSH-cFlag expression cassette, fragment II was synthesized by annealing two specific oligonucleotide sequences (IDSspFOR 5'-GGC CGC ATG CCC CCG CCC CGC ACC GGC CGC GGC CTG CTG TGG CTG GGC CTG GTG CTG AGC AGC GTG TGC GTG GCC CTG GGC-3' (SEQ ID No. 32) and IDSspREV 5'-GCC CAG GGC CAC GCA CAC GCT GCT CAG CAC CAG GCC CAG CCA CAG CAG GCC GCG GCC GGT GCG GGG CGG GGG CAT GC-3' (SEQ ID No. 33) containing the human Iduronate sulfatase signal peptide sequence [Homo sapiens iduronate 2-sulfatase (IDS) cDNA: 75 bp]. The fragment encoding for such signal peptide was: 5'-ATGCCGCCACCCCGGACCG-GCCGAGGCCTTCTCTGGCTGGGTCTGGTTCT GAGCTCCGTCTGCGTCGCCCTCGGA-3' (SEQ ID No. 3) or an optimized sequenze 5'-ATGCCCCCGCCCCGCAC-CGGCCGCGGCCTGCTGTGGCTGGGCCTGGTG CTGAGCAGCGTGTGCGTGGCCCTGGGC-3' (SEQ ID No. 5). The two above sequences differ only for the codon usage and encode for the same signal peptide aa. sequence (SEQ ID No. 4 or 6). The oligonucleotide sequences of fragment II have 5' NotI site and 3' blunt end site. The forward and reverse oligonucleotide sequences were incubated for three minutes at 100° C. After chilling at RT we added the PNK to oligos for 30 minutes at 37° C. The fragment I (5'NotI-3'blunt) and fragment II (5'blunt-3'Xba) were ligated with p3×Flag-CMV14 vector plasmid (5'Not-3'Xba). DH5α competent cells was transformed with the resulting ligation mix.

To obtain the complete SGSH chimeric constructs, the amino acid sequence 3371-3409 of human ApoB (114 bp: 5'TCTGTCATTGATGCACTGCAGTACAAATTAGAGGG CACCACAAGATTGACAAGAAAAAGGG-GATTGAAGTTAGCCACAGCTCTGTC TCTGAGCAA-CAAATTTGTGGAGGGTAGT-3' (SEQ ID No. 9) was amplified by a human cDNA library (oligos: ApoBDFOR 5'-AGA TCT CTG TCA TTG ATG CAC TGC AGT-3' (SEQ ID No. 34) and ApoBDREV 5'-AGA TCT ACT ACC CTC CAC AAA TTT GTT GC-3'(SEQ ID No. 35)) and cloned into the BglII sites at 5' terminus of 3×Flag tag of either hAATsp-SGSH-cFlag or IDSsp-SGSH-cFlag.

The different expression cassettes containing either the partial chimeric constructs (hAATsp-SGSH-cFlag and hIDSsp-SGSH-cFlag) or the complete chimeric constructs (hAATsp-SGSH-cFlag-ApoB and hIDSsp-SGSH-cFlag-ApoB) were subcloned in the pAAV2.1-TBG-GFP between NotI (5') and HindIII (3') (the GFP sequence was replaced with the expression cassettes). The resulting plasmids (FIG. 10) were used to produce recombinant AAV serotype 8 (AAV2/8) (19). The AAV vectors were produced using a transient transfection of three plasmids in 293 cells: pAd helper, pAAV rep-cap (packaging plasmid containing the AAV2 rep gene fused with cap genes of AAV serotype 8), pAAV Cis (this plasmid is pAAV2.1-TGB vector expressing the chimeric sulfamidase proteins). The recombinant AAV2/8 viral vectors were purified by two rounds of CsCl, as described previously (19). Vector titers, expressed as genome copies (GC/ml), were assessed by real-time PCR (GeneAmp 7000 Applied Biosystem). The AAV vectors were produced by the TIGEM AAV Vector Core Facility (http://www.tigem.it/core-facilities/adeno-associated-virus-aav-vector-core).

Trasfections and Secretions in Cells.

Hela and MPSIIIA MEF Cells were maintained in DMEM supplemented with 10% FBS and penicillin/streptomycin (normal culture medium). Sub-confluent cells were transfected using Lipofectamine™ 2000 (Invitrogen) according to manufacturer's protocols. One day after transfection the medium was replaced with DMEM 0.5% FBS. Two days after transfection we collected the conditioned medium and the pellet for the enzyme assays and western blot analysis.

WB Analysis

3×flag Lysis buffer 1× (50 mM Tris-HCl pH8, 200 mM NaCl, 1% Triton X100, 1 mM EDTA, 50 mM HEPES) was added to the cell pellets. The lysates were obtained by incubating the cell pellets with lysis buffer for 1 hour in ice. Protein concentration was determined using the Bio-Rad (Bio-Rad, Hercules, Calif., USA) colorimetric assay. The conditioned medium was concentrated in the vivaspin 500 (Sartorius) by centrifugation of the medium at 13.000 rpm for 7 min. Flagged sulfamidase proteins were revealed by Western Blot analysis using a anti-FLAG M2 monoclonal peroxidase-conjugate antibodies (A8592 Sigma-Aldrich) diluted 1:1000 in 5% milk.

Immunofluorescence

Cells were washed three times in cold PBS and then fixed in 4% paraformaldehyde (PFA) for 15 min. Fixed cells were washed four times in cold PBS, permeabilized with blocking solution (0.1% Saponin and 10% FBS in PBS) for 30 min and immunolabelled with appropriate primary antibody: Rabbit anti h-sulfamidase (1:300, Sigma). After four washes in PBS we incubated the cells with secondary antibody Anti-Rabbit Alexa fluor-488 conjugated (1:1000). Cells were then washed four times in cold PBS and mounted in Vectashield mounting medium.

Pulse and Chase

To determine degradation rates of sulfamidase enzyme, MPSIIIA MEFs transfected with different chimeric constructs were radiolabeled with 30 μCi/$10^6$ cells [35S]methionine:cysteine mixture (EasyTag™ EXPRE35S35S Protein Labeling Mix, [3S]; PerkinElmer) for 30 minutes in methionine:cysteine-free medium (Sigma) supplemented with 1% fetal calf serum. After extensive washing, cells were maintained in the presence of 5% fetal calf serum and supplemented with methionine and cysteine. Cells were recovered at different time points and lysed using 3×flag Lysis buffer. Lysates were cleared by centrifugation and supernatants were immunoprecipitated by using agarose-conjugated antibody against flag (anti-flag M2 affinity Gel, A2220Sigma-Aldrich). After extensive washing with lysis buffer, the immunoprecipitate was subjected to SDS-PAGE. Dried gels were exposed to a PhosphorImager screen and quantified with a PhosphorImager system.

Animals

Homozygous mutant (MPS-IIIA, −/−) and heterozygous (phenotypically normal +/−) C57BL/6 mice were utilized. Consequently, the term 'normal mice' is used to refer to the mouse phenotype. Experiments were conducted in accordance with the guidelines of the Animal Care and Use Committee of Cardarelli Hospital in Naples and authorized by the Italian Ministry of Health.

Systemic Injection and Tissues Collection

Newborn MPS-IIIA and normal mice at postnatal day 0-1 were cryo-anesthetized. The vectors were delivered in the systemic route via temporal vein ($2\times10^{11}$ particles in 100 μl). The adult MPSIIIA mice (1 month) were injected via caudal vein ($2\times10^{11}$ particles in 100 μl). The serum of animals were collected at at different time points after injection for the enzyme assays. To evaluate liver and brain transduction the animals were sacrificed at different time points. Some of them were perfused/fixed with 4% (w/v) paraformaldehyde in PBS, the liver was then removed for GFP staining. The remaining mice were sacrificed and liver and brain removed to measure SGSH activity.

SGSH Activity Assay

SGSH activity was measured following protocols described in Fraldi et al., *Hum Mol Gen* 2007).

GFP Analysis

Liver tissues were subjected to a saccharose gradient (from 10 to 30%) and incubated O/N in 30% saccharose at 4° C. Finally, tissues were embedded in OCT embedding matrix (Kaltek) and snap-frozen in a bath of dry ice and ethanol. Tissue cryosections were cut at 10 μm of thickness, washed with PBS for 10 min, mounted in Vectashield mounting medium and processed for GFP analysis.

Results

The aim of the project was to develop a low-invasive systemic gene therapy strategy based on the intravenous injection of AAV serotype 8. This serotype displays high tropism to the liver (18-20) and can be used to delivery of an engineered gene encoding a chimeric modified sulfamidase optimized (i) to be highly secreted from the liver thus reaching high levels of circulating enzyme in the blood stream. Sulfamidase is poor secreted respect to other sulfatase enzymes such as the iduronate-2-sulfatase (IDS). Sulfamidase signal peptide was replaced with that of either IDS or human α-antitrypsin (AAT), a highly secreted enzyme; (ii) to efficiently cross the BBB. The chimeric sulfamidase was further engineered with a specific brain-targeting protein domain, the (LDLR)-binding domain of the apolipoprotein B (ApoB LDLR-BD).

In Vivo Results in MPS IHA Mice

The efficacy of the new treatment is strictly dependent on the ability of the liver to be highly transduced by the transgene in order to efficiently secrete in the blood stream the sulfamidase that will then cross the BBB and transduce the brain by means of its brain-target sequence. Therefore, the serum levels of the therapeutic enzyme may represent critical factor in determining the efficacy of the therapy. No previous studies have been done to analyze liver transduction and the systemic levels of SGSH upon systemic gene delivery of exogenous SGSH in MPS-IIIA mice. Thus, we decided to investigate this issue in order to produce useful preliminary data for designing an effective therapeutic strategy.

The delivery of therapeutic enzyme to neonatal mice is a useful tool to prevent pathology in MPS-IIIA mice. We then decided to test whether the AAV2/8-mediated systemic injection in newborn MPSIIIA could be a feasible approach to develop our new therapeutic strategy. To this aim we injected MPS-IIIA newborn mice with AAV2/8 containing the sulfamidase coding sequence under the control of a liver specific promoter (Thyroid hormone-globulin, TBG) in order to specifically target the liver and make it like a factory organ of the therapeutic enzyme. Mice were injected via temporal vein with $1\times10^{11}$ particles of virus. Three experimental groups of mice were established: control mice (heterozygous mice; these mice display a normal phenotype) treated with AAV2/8-TBG-GFP, MPS-IIIA mice treated with AAV2/8-TBG-GFP and MPS-IIIA mice treated with AAV2/8-TBG-SGSH.

Figure 1:
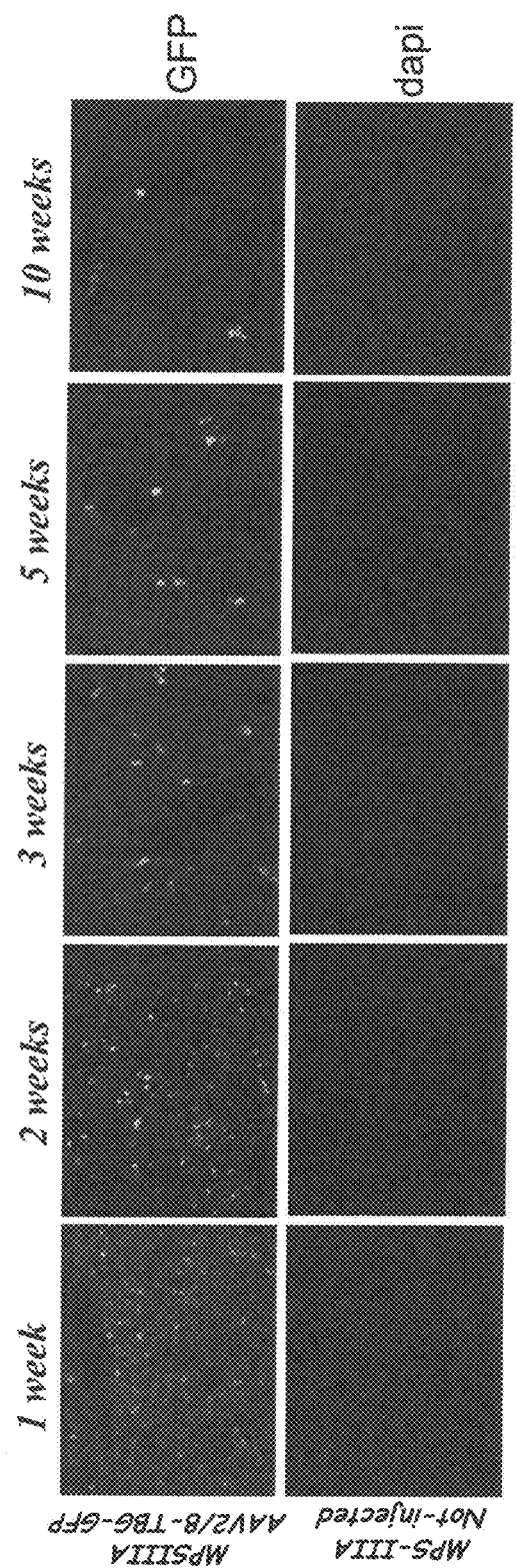
FIG. 1. Non-modified SGSH: Preliminary in vivo study 1 (newborn treatment). Analysis of GFP signal in liver of newborn MPSIIA mice injected with AAV2/8-TBG-GFP. Newborn MPSIIIA were injected with AAV2/8-TBG-SGSH vectors (expressing a not-modified sulfamidase). As control, newborn MPSIIIA and Heterozygous (phenotypically normal) mice were injected with AAV2/8-TBG-GFP vectors. Liver sections from MPS-IIIA injected mice were analyzed for GFP staining at different time after injection (1,2,3,5 and 10 weeks after injection). The GFP signal was very strong at early time points. However, a significant decrease of GFP signal was observed at later time point after injection FIG. 2. Non-modified SGSH: Preliminary in vivo study 1 (newborn treatment). SGSH activity in the liver and serum of newborn injected mice. The sulfamidase activity was measured in the serum (A) and liver (B) of MPSIIIA mice injected with AAV2/8-TBG-SGSH and control mice (MPS-IIIA and heterozygous mice injected with AAV2/8-TBG-GFP). (A) The SGSH activity in plasma of AAV2/8-TBG-SGSH-treated MPS-IIIA mice increased during the first two weeks period after neonatal treatment, and then decreased through the time to reach the levels measured in control GFP-injected MPS-IIIA mice. (B) The analysis of liver SGSH activity showed a trend similar to that observed in the plasma with higher levels of activity detected within the first week after injection.
Figure 2A:
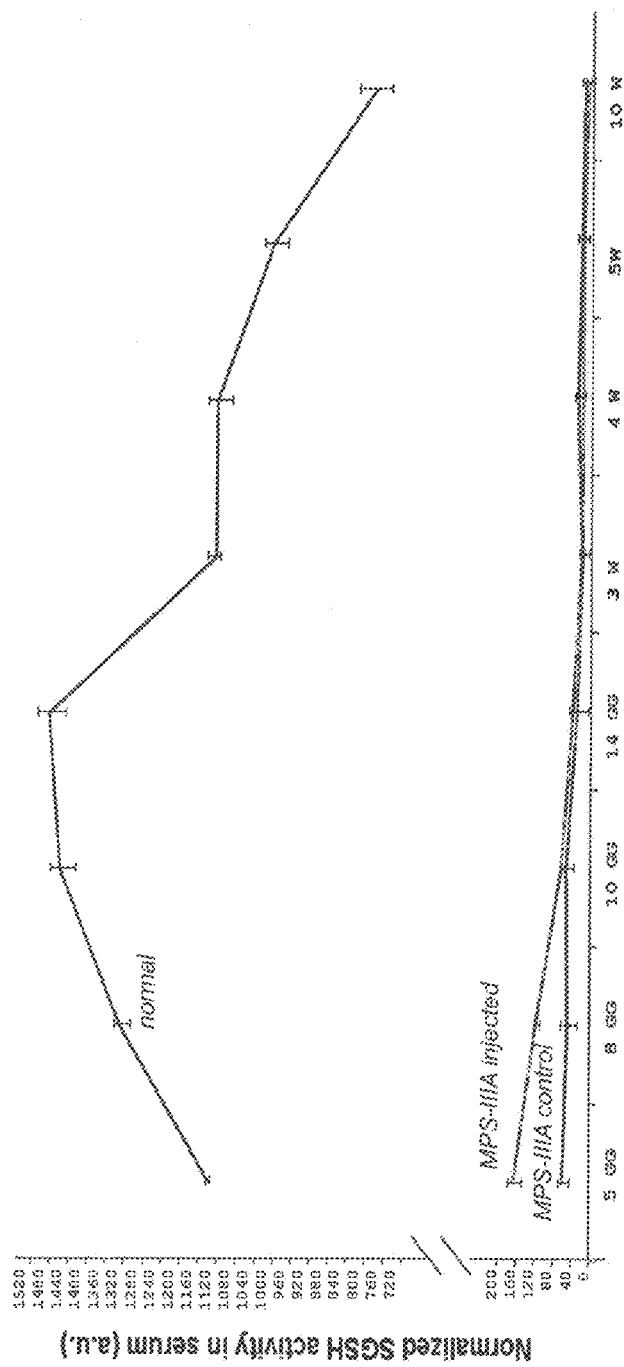
Figure 2B:
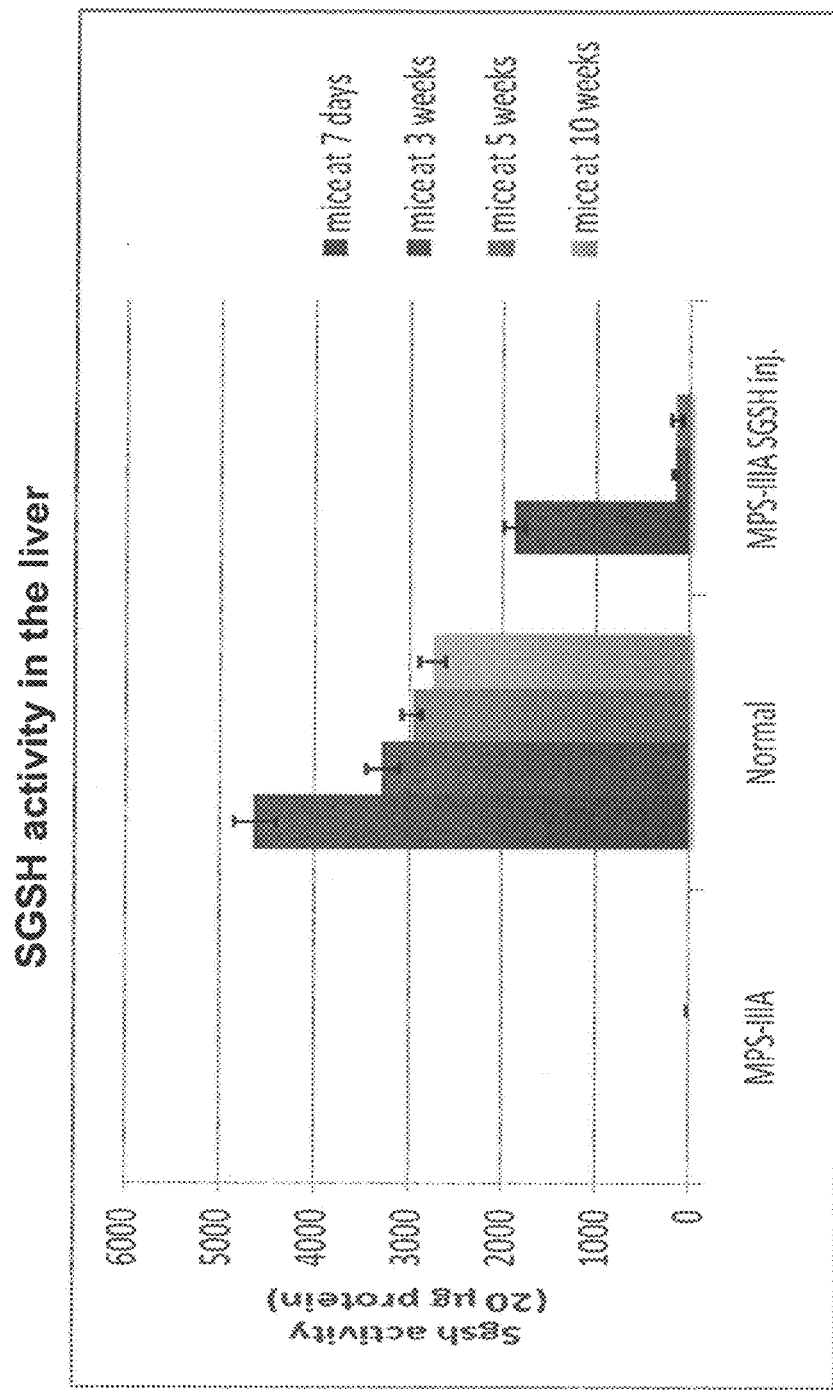

To test the efficiency of injection we analyzed the GFP fluorescence in the liver of GFP-injected mice (normal and MPS-IIIA mice). The GFP signal was present at either early or late time point after injection; however, a significant decrease of GFP signal was observed in the liver of mice analyzed at later time point after injection (FIG. 1). The MPS-IIIA mice injected with AAV2/8-TBG-SGSH were checked for SGSH activity in plasma and in the liver at different time points after injection (5, 8, 10, 14 days and at 3, 4, 5, and 10 weeks). The SGSH activity in plasma of AAV2/8-TBG-SGSH-treated MPS-IIIA mice increased during the first two weeks period after neonatal treatment, and then decreased through the time to reach the levels measured in control GFP-injected MPS-IIIA mice (FIG. 2A). The analysis of liver SGSH activity showed a trend similar to that observed in the plasma with higher levels of activity detected within the first week after injection (FIG. 2B).

This preliminary study in newborn mice demonstrated that although the liver is efficiently transduced by AAV2/8-mediated neonatal delivery of sulfamidase, the enzyme is present at low levels (comparable to control GFP-injected MPS-IIIA mice) into both the liver and serum after 1 week post-injection making this approach unfeasible to treat the brain.

To evaluate whether the proliferation of hepatocytes during the period after the treatment is responsible for the liver dilution of vector after neonatal injection we performed a new study based on the systemic (caudal vein injection) AAV2/8-mediated delivery of SGSH in adult mice (1.5 month of age), in which the liver has completed its growth.

Figure 3:
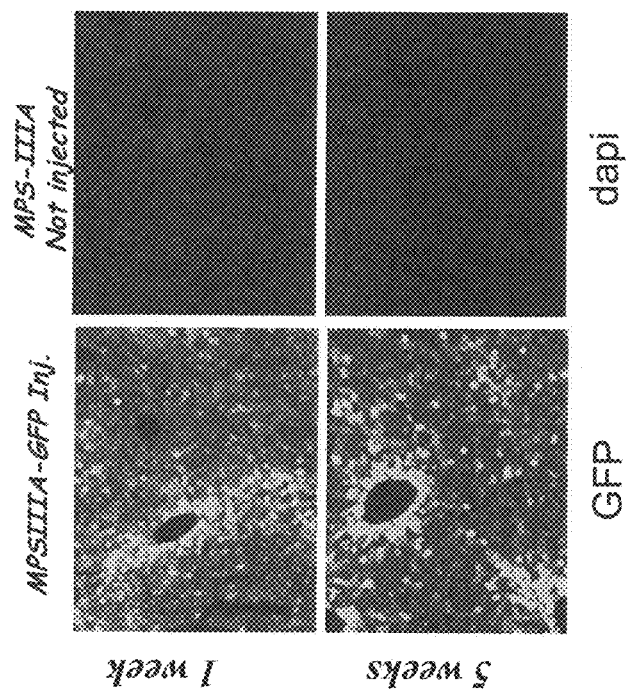
FIG. 3. Non-modified SGSH: Preliminary in vivo study 2 (adult treatment). Analysis of GFP signal in liver of adult MPSIIA mice injected with AAV2/8-TBG-GFP. 1.5 months old MPSIIIA were injected with AAV2/8-TBG-SGSH vectors (expressing a not-modified sulfamidase). As control, 1.5 months old MPSIIIA and Heterozygous (phenotypically normal) mice were injected with AAV2/8-TBG-GFP vectors. Liver sections from MPS-IIIA injected mice were analyzed for GFP staining at 1 and 5 weeks after injection. A high and stable expression of the GFP was observed.
Figure 4A:
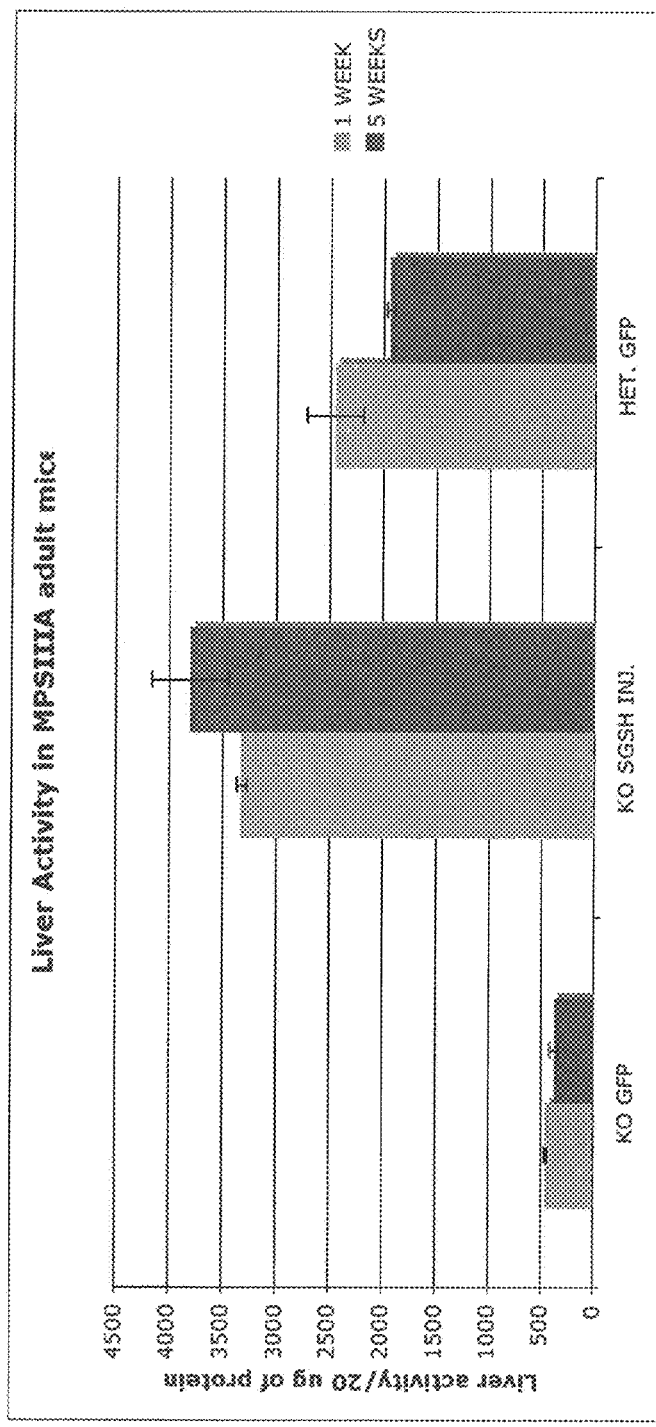
Figure 4B:
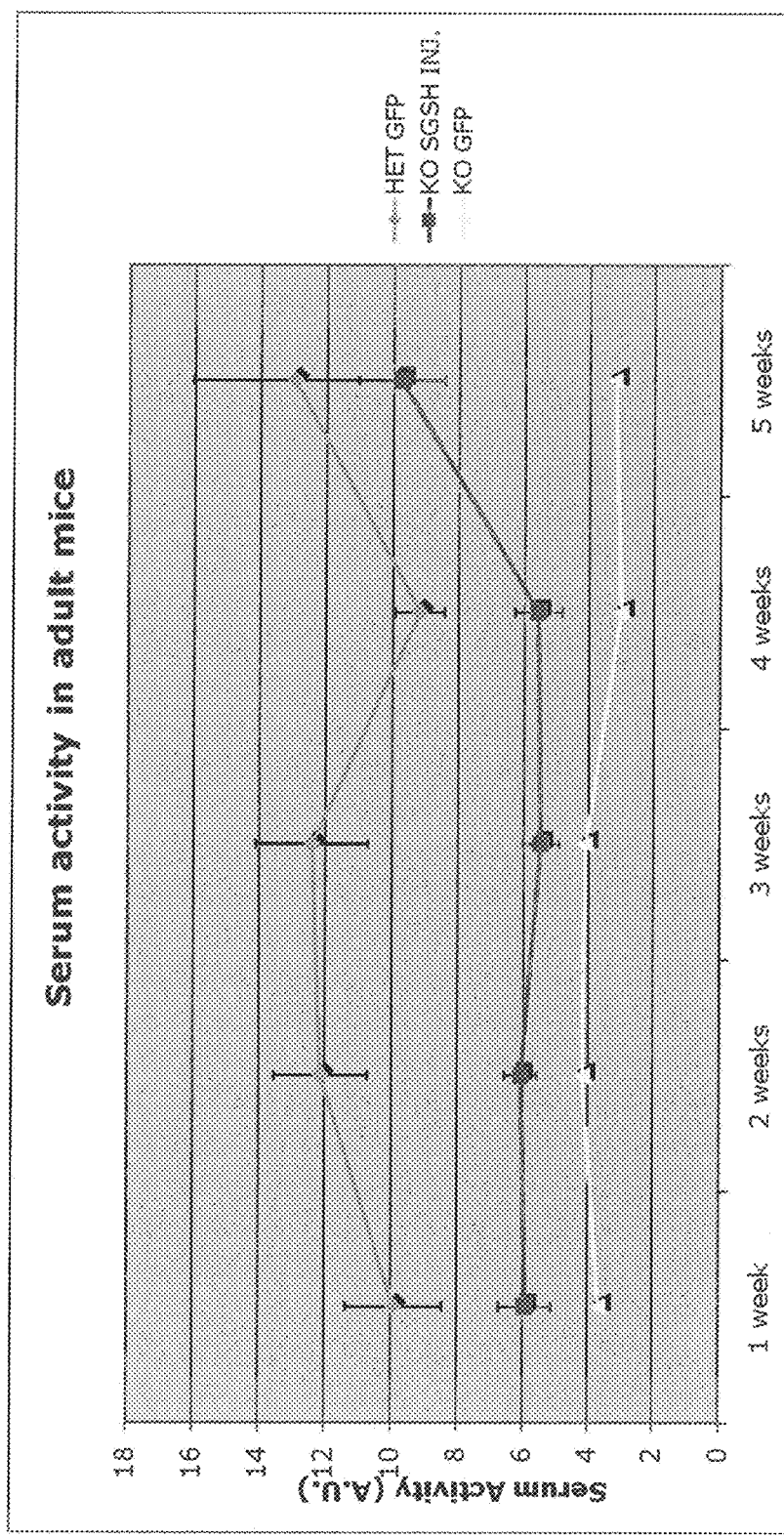

Also in this study we established three experimental groups of mice: normal mice treated with AAV2/8-TBG-GFP, MPS-IIIA mice treated with AAV2/8-TBG-GFP and MPS-IIIA mice treated with AAV2/8-TBG-SGSH. The analysis of GFP expression, at different time points after treatment (1 week and 5 weeks after injection) underlined a high and stable expression of the transgene in the liver of adult treated mice (FIG. 3). MPSIIIA treated mice were also checked for the SGSH activity in the liver and in the serum at different time points (1 week, 2-,3-,4-, 5-weeks) after the treatment. In the liver of MPSIIIA mice injected with AAV2/8-TBG-SGSH we observed a strong increase of SGSH activity compared with low enzyme activity in the animals injected with GFP vector, and this activity remained stable until 5 weeks after injection (the later time point analyzed) (FIG. 4A). Also the analysis of SGSH activity in the serum of treated mice was very high and stable until during the entire post-injection period analyzed (FIG. 4B). Importantly, this treatment did not result in any detectable sulfamidase activity into the brain of AAV2/8-injected MPS-IIIA mice (not shown).

In conclusion these preliminary studies show that: (i) liver is highly transduced by AAV2/8-mediated systemic injection (ii) the decrease of SGSH activity in the newborn treated mice was due to the dilution of vector in the liver and allow us to consider the adult mice a good model to test the systemic treatment with AAV2/8 containing the chimeric sulfamidase (iii) the secreted (non modified) sulfamidase did not result in a detectable enzymatic activity into the brain. The latter is an expected result and further justifies the rationale behind the aim of our project.

Construction and Validation of the Chimeric Sulfamidase Proteins

In order to increase sulfamidase secretion from the liver and thus the amount of the enzyme in the blood stream available to specifically target the brain, we engineered the sulfamidase by replacing its own signal peptide (SP) with an alternative one. Two signal peptides have been tested, the Iduronate-2-sulfatase (IDS) signal peptide and the human a-antitrypsin (AAT) signal peptide (FIG. 5). The rationale behind the use of these two signal peptides is that IDS is a lysosomal enzyme that was demonstrated to be secreted at high levels from the liver [21] while the AAT is a highly secreted enzyme. The final goal of our project is to produce a modified sulfamidase capable to cross the BBB and target the CNS via receptor-mediated transcytosis (FIG. 6). For this reason before starting the experiments aimed at evaluating the therapeutic efficacy of the substituting SP signal in SGSH, we further engineered the modified SGSH with a specific brain-targeting protein domain, the Low Density Lipoprotein receptor (LDLR)-binding domain of the Apolipoprotein B (ApoB LDLR-BD). The Binding Domain of ApoB will allow the sulfamidase to reach the brain cells by binding LDL receptors, which are abundant on the endothelial cells of BBB (FIG. 6). The two finally engineered sulfamidase constructs contain at C-terminal the ApoB LDLR-BD and at N-terminal either an IDS or an hAAT signal peptide (IDSsp-SGSHflag-ApoB and hAATsp-SGSHflag-ApoB) (FIG. 5).

Figure 7A:
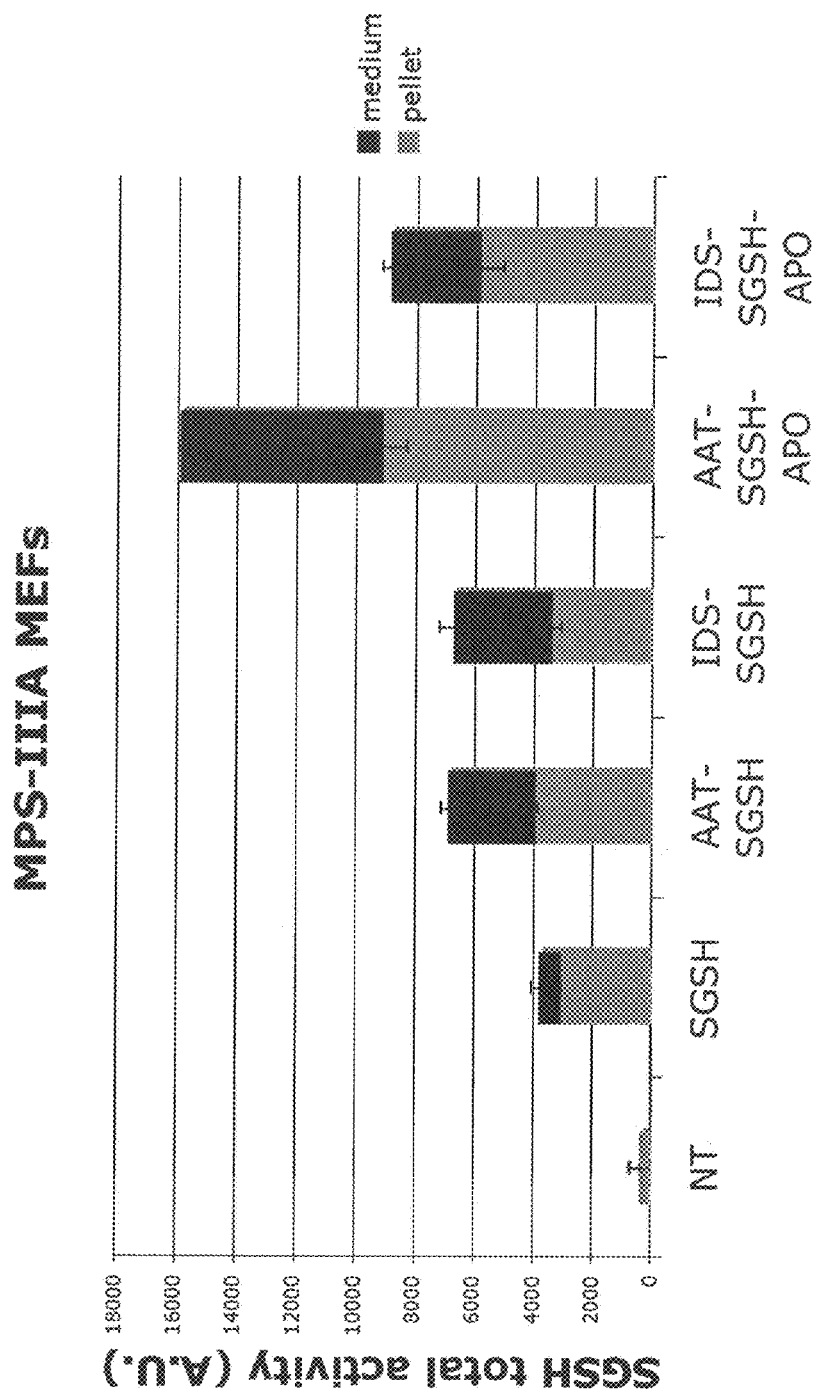
Figure 7B:
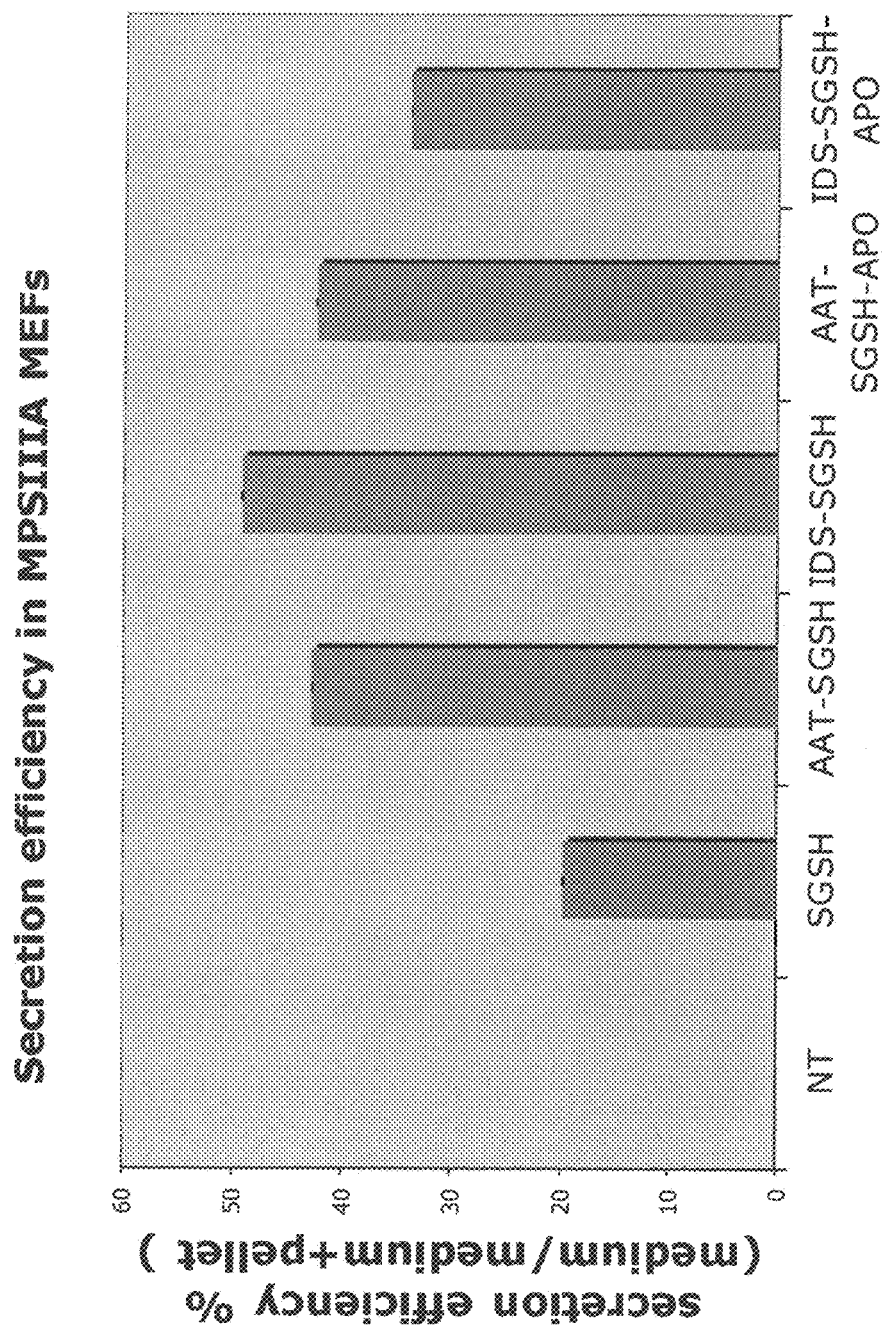

To evaluate the functionality of chimeric sulfamidase proteins we transfected MPSIIIA MEF cells with either partial or final engineered sulfamidase proteins and compared the outcomes with those resulting from the transfections with not-engineered sulfamidase. Surprisingly, we observed that SGSH activity in the pellet and in the conditioned medium was higher in the cells transfected with the final chimeric constructs compared with the activity measured in the cells transfected with the other constructs, indicating that finally engineered sulfamidase were efficiently secreted (FIG. 7A). Indeed, these results were associated with a higher secretion efficiency of the finally engineered sulfamidase enzymes with respect to non-engineered sulfamidase (FIG. 7B). However, this secretion efficiency was similar to that measured after transfection of partially chimeric sulfamidase (containing only the alternative signal peptide) (FIG. 7B). Remarkably, we observed that the modifications of the sulfamidase, in particular those present in the finally engineered sulfamidase, confer to the chimeric proteins a higher stability compared to the non-engineered sulfamidase (FIGS. 8A and B). Thus, we concluded that the increase in the sulfamidase protein levels in the medium of cells transfected with engineered sulfamidase proteins was due to both increased efficiency in secretion and increased stability of engineered sulfamidase.

Moreover, immunostaining with anti-SGSH antibodies showed a lysosomal-like localization for both partial and final engineered constructs (FIG. 8C).

In conclusion these results demonstrate that: (i) the chimeric sulfamidase enzymes containing the alternative signal peptide are functional and active; (ii) they are more stable with respect to non-modified sulfamidase; (iii) they are secreted with increased efficiency compared to non-engineered sulfamidase enzyme; (iv) the introduction of the ApoB LDLR-BD to produce the finally engineered sulfamidase did not affect either the functionality or the increased secretion efficiency observed in the cells transfected with the partially engineered sulfamidase. In addition, the finally engineered constructs appear to be more stable compared to partially engineered constructs.

In Vivo Results in MPS IIIA Mice Injected with Finally Engineered Sulfamidase

We produced AAV2/8 vectors containing one of the finally engineered sulfamidase (hAATsp-SGSHflag-ApoB) under the liver specific promoter TBG. We obtained very preliminary but extremely encouraging results in MPS-IIIA injected with this viral vector. Adult MPS-IIIA mice were systemically injected with AAV2/8-TBG- hAATsp-SGSHflag-ApoB. A group of MPS-IIIA were also injected with AAV2/8-TBG-SGSH (containing the not modified sulfamidase) as control. The mice were sacrificed one month after injection. In the mice injected with the chimeric sulfamidase we observed higher liver sulfamidase activity and a very strong increase in the sulfamidase secretion respect to control mice (FIG. 9). Moreover, we detected a significant increase in SGSH activity into the brain of mice injected with the chimeric sulfamidase (FIG. 9).

Use of Other Vectors

We completed the production of the AAV2/8 vectors containing all the engineered sulfamidase proteins (partial and final). Specifically, besides the AAV2/8-TBG-hAATsp-SGSHflag-ApoB, we now produced AAV2/8-TBG-hIDSsp-SG-SHflag-ApoB; AAV2/8-TBG- hAATsp-SGSHflag and AAV2/8-TBG-hIDSsp-SGSHflag.

These vectors may be used to perform a large in vivo study by the following procedure: MPS-IIIA mice (1 month of age) are injected (by a caudal vein route of administration) with AAV2/8 vectors containing the engineered constructs in order to test the clinical efficacy of the chimeric sulfamidase enzymes. Results are useful to evaluate (i) the efficiency of CNS transduction and (ii) the rescue of CNS pathology in the treated mice.

BIBLIOGRAPHY

1. Muenzer, J. (2004) The mucopolysaccharidoses: a heterogeneous group of disorders with variable pediatric presentations. *J Pediatr*, 144, S27-34.
2. Bhaumik, M., Muller, V. J., Rozaklis, T., Johnson, L., Dobrenis, K., Bhattacharyya, R., Wurzelmann, S., Finamore, P., Hopwood, J. J., Walkley, S. U. et al. (1999) A mouse model for mucopolysaccharidosis type III A (Sanfilippo syndrome). *Glycobiology*, 9, 1389-96.
3. Bhattacharyya, R., Gliddon, B., Beccari, T., Hopwood, J. J. and Stanley, P. (2001) A novel missense mutation in lysosomal sulfamidase is the basis of MPS III A in a spontaneous mouse mutant. *Glycobiology*, 11, 99-103.
4. Hemsley, K. M. and Hopwood, J. J. (2005) Development of motor deficits in a murine model of mucopolysaccharidosis type IIIA (MPS-IIIA). *Behav Brain Res*, 158, 191-9.
5. Savas, P. S., Hemsley, K. M. and Hopwood, J. J. (2004) Intracerebral injection of sulfamidase delays neuropathology in murine MPS-IIIA. *Mol Genet Metab*, 82, 273-85.
6. Hemsley, K. M., King, B. and Hopwood, J. J. (2007) Injection of recombinant human sulfamidase into the CSF via the cerebellomedullary cistern in MPS IIIA mice. *Mol Genet Metab*, 90, 313-28.
7. Fraldi, A., Hemsley, K., Crawley, A., Lombardi, A., Lau, A., Sutherland, L., Auricchio, A., Ballabio, A. and Hopwood, J. J. (2007) Functional correction of CNS lesions in an MPS-IIIA mouse model by intracerebral AAV-mediated delivery of sulfamidase and SUMF1 genes. *Hum Mol Genet*, 16, 2693-702.
8. Pardridge, W. M. (2002) Drug and gene delivery to the brain: the vascular route. *Neuron*, 36, 555-8.
9. Pardridge, W. M. (2005) Molecular biology of the blood-brain barrier. *Mol Biotechnol*, 30, 57-70.
10. Brady, R. O. and Schiffmann, R. (2004) Enzyme-replacement therapy for metabolic storage disorders. *Lancet Neurol*, 3, 752-6.
11. Gliddon, B. L. and Hopwood, J. J. (2004) Enzyme-replacement therapy from birth delays the development of behavior and learning problems in mucopolysaccharidosis type IIIA mice. *Pediatr Res*, 56, 65-72.
12. Urayama, A., Grubb, J. H., Sly, W. S. and Banks, W. A. (2008) Mannose 6-phosphate receptor-mediated transport of sulfamidase across the blood-brain barrier in the newborn mouse. *Mol Ther*, 16, 1261-6.
13. Pardridge, W. M. (2002) Targeting neurotherapeutic agents through the blood-brain barrier. *Arch Neurol*, 59, 35-40.
14. Brown, M. S. and Goldstein, J. L. (1986) A receptor-mediated pathway for cholesterol homeostasis. *Science*, 232, 34-47.
15. Stefansson, S., Chappell, D. A., Argraves, K. M., Strickland, D. K. and Argraves, W. S. (1995) Glycoprotein 330/low density lipoprotein receptor-related protein-2 mediates endocytosis of low density lipoproteins via interaction with apolipoprotein B100. *J Biol Chem*, 270, 19417-21.

16. Boren, J., Lee, I., Zhu, W., Arnold, K., Taylor, S. and Innerarity, T. L. (1998) Identification of the low density lipoprotein receptor-binding site in apolipoprotein B100 and the modulation of its binding activity by the carboxyl terminus in familial defective apo-B100. *J Clin Invest*, 101, 1084-93.
17. Spencer, B. J. and Verma, I. M. (2007) Targeted delivery of proteins across the blood-brain barrier. *Proc Natl Acad Sci USA*, 104, 7594-9.
18. Cheng, S. H. and Smith, A. E. (2003) Gene therapy progress and prospects: gene therapy of lysosomal storage disorders. *Gene Ther*, 10, 1275-81.
19. Gao, G. P., Alvira, M. R., Wang, L., Calcedo, R., Johnston, J. and Wilson, J. M. (2002) Novel adeno-associated viruses from rhesus monkeys as vectors for human gene therapy. *Proc Natl Acad Sci USA*, 99, 11854-9.
20. Wang, L., Takabe, K., Bidlingmaier, S. M., Ill, C. R. and Verma, I. M. (1999) Sustained correction of bleeding disorder in hemophilia B mice by gene therapy. *Proc Natl Acad Sci USA*, 96, 3906-10.
21. Cardone, M., et al., Correction of Hunter syndrome in the MPSII mouse model by AAV2/8-mediated gene delivery. Hum Mol Genet, 2006. 15(7): p. 1225-36.

The invention claimed is:

1. A method for treating a human subject diagnosed with a mucopolysaccharidoses (MPS) pathology, comprising administering to the subject a suitable amount of a pharmaceutical composition comprising a viral vector, via a systemic route of administration,
   wherein the MPS pathology is MPS type IIIA,
   wherein the viral vector comprises a recombinant plasmid suitable for gene therapy of MPS type IIIA,
   wherein the recombinant plasmid comprises a nucleotide sequence encoding for a chimeric sulfatase, said chimeric sulfatase consisting essentially of, in the N-terminal to C-terminal sequence order of:
   a) a signal peptide derived from either the human α-antitrypsin (hAAT) amino acid sequence or the human Iduronate-2-sulfatase (IDS) amino acid sequence;
   b) a human sulfatase derived amino acid sequence deprived of its signal peptide;

c) the ApoB LDLR-binding domain; and
wherein the human sulfatase is human sulfamidase.

2. A method for treating a human subject diagnosed with mucopolysaccharidoses (MPS) pathology comprising administering to the subject in need thereof a suitable amount of a pharmaceutical composition comprising a chimeric sulfatase;
wherein the MPS pathology is MPS type IIIA,
wherein the chimeric sulfatase consists essentially, in the N-terminal to C-terminal sequence order, of:
a) a signal peptide derived from either the human α-antitrypsin (hAAT) amino acid sequence or the human Iduronate-2-sulfatase (IDS) amino acid sequence;
b) a human sulfatase derived amino acid sequence deprived of its signal peptide; and
c) the ApoB LDLR-binding domain;
wherein the human sulfatase is human sulfamidase.

3. The method according to claim 1, wherein the signal peptide has the sequence of SEQ ID NO: 2 or SEQ ID NO: 4.

4. The method according to claim 1, wherein the encoded human sulfamidase derived amino acid sequence consists essentially of SEQ ID NO: 8.

5. The method according to claim 1, wherein the encoded ApoB LDLR-binding domain consists essentially of SEQ ID NO: 10.

6. The method according to claim 1, wherein the nucleotide sequence is selected from the group consisting of:
a) Assembly hAATsp-SGSH-3xflag-ApoB cassette (SEQ ID NO: 15),
b) Assembly hIDSsp-SGSH-3xflag-ApoB cassette (SEQ ID NO: 17),
c) Assembly hAATsp-SGSH-ApoB cassette (SEQ ID NO: 23) and
d) Assembly hIDSsp-SGSH-ApoB cassette (SEQ ID NO: 25).

7. The method according to claim 1, wherein the nucleotide sequence is under the control of a liver specific promoter.

8. The method according to claim 7 wherein the liver specific promoter is the human thyroid hormone-globulin (TBG) promoter.

9. The method according to claim 1 wherein the viral vector is selected from the group consisting of lentiviral vectors, helper-dependent adenoviral vectors or AAV vectors.

10. The method according to claim 1 wherein the recombinant plasmid is AAV2.1.

11. The method according to claim 1 wherein the viral vector is an AAV viral vector.

12. The method according to claim 11 wherein the viral vector is an AAV serotype 8 vector.

13. The method according to claim 2, wherein the signal peptide has the sequence of SEQ ID NO: 2 or SEQ ID NO: 4.

14. (Withdrawn/New) The method according to claim 2, wherein the encoded human sulfamidase derived amino acid sequence consists essentially of SEQ ID NO: 8.

15. The method according to claim 2, wherein the encoded ApoB LDLR-binding domain consists essentially of SEQ ID NO: 10.

16. The method according to claim 2, wherein the chimeric sulfatase comprises a sequence selected from the group consisting of:
a) hAATsp-SGSH-3xflag-ApoB aminoacid sequence (SEQ ID NO: 16),
b) hIDSsp-SGSH-3xflag-ApoB aminoacid sequence (SEQ ID NO: 18),
c) hAATsp-SGSH-ApoB aminoacid sequence (SEQ ID NO: 24) and
d) hIDSsp-SGSH-ApoB aminoacid sequence (SEQ ID NO: 26).

17. The method according to claim 8 wherein the human thyroid hormone-globulin (TBG) promoter comprises SEQ ID NO: 27.

18. The method according to claim 1 wherein the pharmaceutical composition consists of the viral vector.

19. The method according to claim 2 wherein the pharmaceutical composition consists of the chimeric sulfatase.

* * * * *

UNITED STATES PATENT AND TRADEMARK OFFICE
CERTIFICATE OF CORRECTION

| | | |
|---|---|---|
| PATENT NO. | : 9,206,401 B2 | Page 1 of 1 |
| APPLICATION NO. | : 13/996386 | |
| DATED | : December 8, 2015 | |
| INVENTOR(S) | : Ballabio | |

It is certified that error appears in the above-identified patent and that said Letters Patent is hereby corrected as shown below:

In the Claims:

Column 94, Line 11, Claim 12 should read as follows:

--12. The method according to claim 11 wherein the viral vector is an AAV serotype 8 vector.--

Column 94, Line 14, Claim 14 should read as follows:

--14. The method according to claim 2, wherein the encoded human sulfamidase derived amino acid sequence consists essentially of SEQ ID NO: 8.--

Signed and Sealed this
Twenty-ninth Day of March, 2016

Michelle K. Lee
*Director of the United States Patent and Trademark Office*